US012139543B2

(12) United States Patent
Lowman et al.

(10) Patent No.: US 12,139,543 B2
(45) Date of Patent: Nov. 12, 2024

(54) METHOD OF USING AN ANTI-EPIDERMAL GROWTH FACTOR RECEPTOR (EGFR) ACTIVATABLE ANTIBODY TO DETECT THE PRESENCE OR ABSENCE OF A CLEAVING AGENT AND EGFR

(71) Applicant: CytomX Therapeutics, Inc., South San Francisco, CA (US)

(72) Inventors: Henry Bernard Lowman, El Granada, CA (US); Luc Roland Desnoyers, San Francisco, CA (US); Shouchun Liu, Burlingame, CA (US)

(73) Assignee: CytomX Therapeutics, Inc.

( * ) Notice: Subject to any disclaimer, the term of this patent is extended or adjusted under 35 U.S.C. 154(b) by 0 days.

(21) Appl. No.: 17/532,193

(22) Filed: Nov. 22, 2021

(65) Prior Publication Data
US 2022/0289853 A1  Sep. 15, 2022

Related U.S. Application Data

(62) Division of application No. 16/712,422, filed on Dec. 12, 2019, now Pat. No. 11,180,562, which is a division of application No. 15/382,890, filed on Dec. 19, 2016, now Pat. No. 10,533,053, which is a division of application No. 14/528,180, filed on Oct. 30, 2014, now Pat. No. 9,540,440.

(60) Provisional application No. 61/897,465, filed on Oct. 30, 2013, provisional application No. 61/897,418, filed on Oct. 30, 2013, provisional application No. 61/897,442, filed on Oct. 30, 2013, provisional application No. 61/897,385, filed on Oct. 30, 2013, provisional application No. 61/897,391, filed on Oct. 30, 2013.

(51) Int. Cl.
C07K 16/28 (2006.01)
A61K 39/395 (2006.01)
A61K 47/68 (2017.01)
G01N 33/564 (2006.01)
G01N 33/574 (2006.01)

(52) U.S. Cl.
CPC .... *C07K 16/2863* (2013.01); *A61K 39/39533* (2013.01); *A61K 47/6817* (2017.08); *A61K 47/6849* (2017.08); *G01N 33/564* (2013.01); *G01N 33/57492* (2013.01); *C07K 2317/14* (2013.01); *C07K 2317/24* (2013.01); *C07K 2317/51* (2013.01); *C07K 2317/515* (2013.01); *C07K 2317/54* (2013.01); *C07K 2317/55* (2013.01); *C07K 2317/569* (2013.01); *C07K 2317/76* (2013.01); *C07K 2317/92* (2013.01); *C07K 2319/50* (2013.01); *G01N 2333/71* (2013.01); *G01N 2800/205* (2013.01)

(58) Field of Classification Search
CPC ............ C07K 16/2863; C07K 2317/51; C07K 2317/515; C07K 2317/54; C07K 2317/55; C07K 2317/569; C07K 2317/76; C07K 2317/92; C07K 2319/50; A61K 39/39533; A61K 47/6817; A61K 47/6849; G01N 2333/71

See application file for complete search history.

(56) References Cited

U.S. PATENT DOCUMENTS

| | | |
|---|---|---|
| 3,773,919 A | 11/1973 | Boswell et al. |
| 4,522,811 A | 6/1985 | Eppstein et al. |
| 5,030,719 A | 7/1991 | Umemoto et al. |
| 5,151,510 A | 9/1992 | Stec et al. |
| 5,525,491 A | 6/1996 | Huston et al. |
| 7,465,790 B2 | 12/2008 | Waldmann et al. |
| 7,666,817 B2 | 2/2010 | Daughtery et al. |
| 8,034,959 B2 | 10/2011 | Ng et al. |
| 8,226,945 B2 | 7/2012 | Ebens et al. |
| 8,513,390 B2 | 8/2013 | Stagliano et al. |
| 8,518,404 B2 | 8/2013 | Daughtery et al. |
| 8,529,898 B2 | 9/2013 | Daughtery et al. |
| 8,541,203 B2 | 9/2013 | Daughtery et al. |
| 8,563,269 B2 | 10/2013 | Stagliano et al. |
| 8,809,504 B2 | 8/2014 | Lauermann |
| 8,895,702 B2 | 11/2014 | Williams et al. |
| 9,120,853 B2 | 9/2015 | Lowman et al. |
| 9,169,321 B2 | 10/2015 | Daughtery et al. |
| 9,453,078 B2 | 9/2016 | Stagliano et al. |
| 9,540,440 B2 | 1/2017 | Lowman et al. |
| 9,545,442 B2 | 1/2017 | Lowman et al. |
| 9,737,623 B2 | 8/2017 | Desnoyers et al. |
| 9,889,211 B2 | 2/2018 | Lowman et al. |
| 10,059,762 B2 | 8/2018 | Stagliano et al. |

(Continued)

FOREIGN PATENT DOCUMENTS

| | | |
|---|---|---|
| EA | 2010/00704 | 12/2010 |
| EP | 1523503 | 1/2004 |

(Continued)

OTHER PUBLICATIONS

Irving, "Probodies Empower a New Generation of Antibody Immunotherapies", presented at Keystone Symposia on Molecular and Cellular Biology, Feb. 2015.
"Cetuximab" (Updated Aug. 17, 2016) DmgBank Accession No. DB00002 [online]. Retrieved from http://www.drugbank.ca/dmgs/DB00002, on Dec. 16, 2016, 10 pages.
Affara et al. "Delineating protease functions during cancer development." Methods Mol Biol., 2009, 539: 1-32.
Azzopardi et al. "Cetuximab Pharmokinetics Influences Progression-Free Survival of Metastatic Colorectal Cancer Patients," Clin Cancer Res., 2011, 17: 6329-37.

(Continued)

Primary Examiner — Robert S Landsman
(74) Attorney, Agent, or Firm — Fish & Richardson P.C.

(57) ABSTRACT

The invention relates generally to variant activatable antibodies that include a masking moiety (MM), a cleavable moiety (CM), and an antibody (AB) that specifically binds to epidermal growth factor receptor (EGFR), and to methods of making and using these variant anti-EGFR activatable antibodies in a variety of therapeutic, diagnostic and prophylactic indications.

25 Claims, 1 Drawing Sheet

Specification includes a Sequence Listing.

(56) References Cited

U.S. PATENT DOCUMENTS

| | | | |
|---|---|---|---|
| 10,077,300 B2 | 9/2018 | Daughtery et al. |
| 10,118,961 B2 | 11/2018 | Stagliano et al. |
| 10,261,083 B2 | 4/2019 | Vasiljeva et al. |
| 10,533,053 B2 | 1/2020 | Lowman et al. |
| 10,568,977 B2 | 2/2020 | Desnoyers et al. |
| 10,709,799 B2 | 7/2020 | Lowman et al. |
| 10,875,913 B2 | 12/2020 | Stagliano et al. |
| 11,028,162 B2 | 6/2021 | Daugherty et al. |
| 11,035,859 B2 | 6/2021 | Vasiljeva et al. |
| 11,180,562 B2 | 11/2021 | Lowman et al. |
| 11,867,695 B2 | 1/2024 | Vasiljeva et al. |
| 2002/0016481 A1 | 2/2002 | Saski et al. |
| 2002/0127564 A1 | 9/2002 | Nolan |
| 2004/0109855 A1 | 6/2004 | Waldmann et al. |
| 2007/0213511 A1 | 9/2007 | Kunz et al. |
| 2008/0114153 A1 | 5/2008 | Steeves et al. |
| 2008/0175847 A1 | 7/2008 | Yan et al. |
| 2009/0148905 A1 | 6/2009 | Ashman et al. |
| 2009/0304719 A1 | 12/2009 | Daughtery et al. |
| 2010/0150939 A1 | 6/2010 | Blanchetot et al. |
| 2010/0189651 A1 | 7/2010 | Stagliano et al. |
| 2010/0189727 A1 | 7/2010 | Rodeck et al. |
| 2011/0178279 A1 | 7/2011 | Williams et al. |
| 2012/0149061 A1 | 6/2012 | Stagliano et al. |
| 2012/0207756 A1 | 8/2012 | Stagliano et al. |
| 2012/0237512 A1 | 9/2012 | Daughtery et al. |
| 2012/0237977 A1 | 9/2012 | Daughtery et al. |
| 2012/0244154 A1 | 9/2012 | Daughtery et al. |
| 2013/0004481 A1 | 1/2013 | Solca et al. |
| 2013/0060010 A1 | 3/2013 | Williams et al. |
| 2013/0309230 A1 | 11/2013 | Stagliano et al. |
| 2013/0315906 A1 | 11/2013 | Lowman et al. |
| 2014/0024810 A1 | 1/2014 | Stagliano et al. |
| 2014/0045195 A1 | 2/2014 | Daughtery et al. |
| 2015/0118254 A1 | 4/2015 | Lowman et al. |
| 2015/0157748 A1 | 6/2015 | Desnoyers et al. |
| 2016/0122425 A1 | 5/2016 | Daughtery et al. |
| 2016/0193332 A1 | 7/2016 | Lowman et al. |
| 2016/0228546 A1 | 8/2016 | Stagliano et al. |
| 2017/0081397 A1 | 3/2017 | Stagliano et al. |
| 2017/0096489 A1 | 4/2017 | Lowman et al. |
| 2017/0196996 A1 | 7/2017 | Lowman et al. |
| 2017/0326260 A1 | 11/2017 | Desnoyers et al. |
| 2018/0333507 A1 | 11/2018 | Lowman et al. |
| 2019/0119370 A1 | 4/2019 | Stagliano et al. |
| 2019/0211089 A1 | 7/2019 | Daughtery et al. |
| 2020/0270350 A1 | 8/2020 | Lowman et al. |
| 2021/0023243 A1 | 1/2021 | Lowman et al. |
| 2021/0284721 A1 | 9/2021 | Stagliano et al. |
| 2022/0098294 A1 | 3/2022 | Daugherty et al. |

FOREIGN PATENT DOCUMENTS

| | | |
|---|---|---|
| EP | 1324771 | 6/2011 |
| JP | 2003-530852 | 10/2003 |
| WO | WO 1994/11026 | 5/1994 |
| WO | WO 1997/31024 | 8/1997 |
| WO | WO 1998/11126 | 3/1998 |
| WO | WO 2001/79271 | 10/2001 |
| WO | WO 2001/79480 | 10/2001 |
| WO | WO 2001/91798 | 12/2001 |
| WO | WO 2002/30460 | 4/2002 |
| WO | WO 2004/009638 | 1/2004 |
| WO | WO 2007/008712 | 1/2007 |
| WO | WO 2007/105027 | 9/2007 |
| WO | WO 2008/101177 | 8/2008 |
| WO | WO 2009/011572 | 1/2009 |
| WO | WO 2009/025846 | 2/2009 |
| WO | WO 2009/068649 | 6/2009 |
| WO | WO 2009/140242 | 11/2009 |
| WO | WO 2010/077643 | 7/2010 |
| WO | WO 2010/081173 | 7/2010 |
| WO | WO 2010/129609 | 11/2010 |
| WO | WO 2011/109789 | 9/2011 |
| WO | WO 2013/043071 | 3/2013 |
| WO | WO 2013/163631 | 10/2013 |
| WO | WO 2014/107599 | 7/2014 |
| WO | WO 2014/197612 | 12/2014 |
| WO | WO 2015/013671 | 1/2015 |
| WO | WO 2015/066279 | 5/2015 |

OTHER PUBLICATIONS

Bagshawe, "Antibody-directed enzyme prodmg therapy (ADEPT) for cancer," Expert Rev Anticancer Ther, 2006, 6(10): 1421-1431.

Baselga et al. "Phase I Studies of Anti-Epidermal Growth Factor Receptor Chimeric Antibody C225 Alone and in Combination with Cisplatin," J. Clin. Oncol., 2000, 18(4): 904-914.

Benjamin RJ, Cobbold SP, Clark MR, Waldmann H. Tolerance to rat monoclonal antibodies. Implications for serotherapy. J Exp Med. 163(6): 1539-52. (1986).

Boulware et al. "Evolutionary optimization of peptide substrates for proteases that exhibit rapid hydrolysis kinetics" Biotec ṁ ol Bioeng. 106(3):339-346 (2010).

Brinks et al. Preclinical models Used for Immunogenicity Prediction of Therapeutic Proteins. Phann. Res 30 1719-1728 (2013).

Chiller et al., "Cellular events during induction of immunologic umesponsiveness in adult mice," J. immunnol.106(6):1647-53 (1971).

Chirinos-Rojas CL, Steward MW, Partidos CD. Use of a solid-phase random peptide library to identify inhibitors of TNF-alpha me/\ated cytotoxicity in vitro. Cyt灼ne. 9(4): 226-32. (1997).

Cwirla et al., "Peptides on phage: a vast library of peptides for identifying ligands," Proc Natl Acad Sci USA., 1990, 87:16::6378-82.

Darragh et al., "Tumor detection by imaging proteolytic activity," Cancer Res., 2010, 70: 1505-1512.

Desnoyers et al. (Oct. 16, 2013) "Tumor-specific activation of an EGFR-targeting pro body enhances therapeutic index" [online]. Retrieved from the Internet: www.sciencetranslationalmedicine.org, vol. 5, issue 207, 207ral44, 10 pages.

Desnoyers. et al. (Apr. 15, 2013) "Abstract 4570: Development of a proteolytically activatable EGFR Pro body for cancer therapy" [o汕ne]. Retrieved from the Internet http://cancerres.aacrjournals.org/content/73/8 Supplement/4570, on Oct. 15, 2015, 2 pages.

Donaldson et al. "Design and Development of Masked Therapeutic Antibodies to Limit Off-Target Effects" Cancer Biol Ther., 2009, 8:22:2147-2152.

Edwards et al., "The Remarkable Flexibility of the human Antibody Repertoire; Isolation of Over One Thousand Different Antibodies to a Single Protein, BLyS" J Mol Biol, 2003, 334(1): 103-118.

Francisco. et al., "cACIO-vcMMAE, an anti-CD30-monomethyl auristatin E conjugate with potent and selected antitumor activity" Blood, 2003, 102: 1458-1465.

Geysen et al, "Strategies for epitope analysis using peptide synthesis," J Innnunol Methods., 1987, 102(2):259-274.

Gilliland et al. "Elimination of the immunogenicity of therapeutic antibodies" J Immunol., 1999, 162(6):3663-3671.

Goldstein et al. Biological Efficacy of a Chimeric Antibody to the Epidermal Growth Factor Receptor in a Human Tumor Xenograft Model. Clin. Cancer Res., 1995, 1: 1311-18.

Gravanis et al., "The European Medicines Agency review of ofatumumab (Arzerra)for the treatment of chronic lymphocytic leukemia in patients refractory to fludarabine and alemtuzurnab: summary of the scientific assessment of the European medicines agency committee for medicinal products for human use," Oncologist., 2010, 15(12): 1335-43.

Hale, "Synthetic peptide mimotope of the CAMPATH-1 (CD52) antigen, a small glycosy lphosphatidy linositol-anchored glycoprotein," Immunotechnology, 1995, 1(3-4): 175-187.

Holliger et al., Diabodies: small bivalent and bispecific antibody fragments. Proc Natl Acad Sci USA., 1993, 90(14):6444-8.

Huston et al., "Protein engineering of antibody binding sites: recovery of specific activity in an anti-digoxin single-chain Fv analogue produced in *Escherichia coli*," Proc Natl Acad Sci U SA., 1988, 85(16):5879-83.

Hutchinson, "Developing patterns," Nature Rev Cancer, 2005, 5: 341.

(56) References Cited

OTHER PUBLICATIONS

Hynes et al., "ERBB receptors and cancer: the complexity of targeted inhibitrs," Nature Rev Cancer 5, 2005, 341-354.

Hynes et al., ErbB receptors and signaling pathways in cancer. Curr Opin Cell Biol, 2009, 21:177-184.

James et al., "1.9 A structure of the therapeutic antibody CAMPATH-1H fab in complex with a synthetic peptide antigen" J Mol Biol., Jun. 1999, 289(2):293-301.

Jansen et al., "Inununotoxins: Hybrid Molecules Combining High specificity and Potent Cytotoxicity" Immunological Reviews, 1982, 62:185-216.

Jensen-Jarolim et al. "Peptide mimotopes displayed by phage inhibit antibody binding to Bet v 1, the major birch pollen allergen, and induce specific IgG response in mice," Dec. 1998, FASEB J. 12(15): 1635-1642.

Kabat et al. Sequences of Proteins of Immunological Interest. 5th Edition, vol. 1., NIB Publication 91-3242, 1991, 310-662.

Katz, "Structural and mechanistic detennrinants of affinity and specficity of ligands discovered or engineered by phage display," Annu Rev Biophys Biomol Struct., 1997, 26:27-45.

Krieckaert et al. "Methotrexate reduces immunogenicity in adalimumab treated rheumatoid arthritis patients in a dose dependent manner," Ann Rheum. Dis., 2012, 71(11): 1914.

Krieckaert et al., "Therapy: Immunogenicity of biologic therapies—we need tolerance," Nat Rev Rheumatol., 2010, 6(10):558-9.

Leibiger et al. (1999) "Variable domain-linked oligosaccharides of a human monoclonal IgG: structure and influence on antigen binding" Biochem J, 338:529-538.

Leitner et al., "A mimotope defined by phage display inhibits IgE binding to the plant panallergen profilin," Eur J Immunol., 1998, 28(9):2921-7.

Li et al., "Structural Basis For Inhibition of the Epidermal Growth Factor Receptor by Cetuximab," Apr. 2005, Cancer Cell 7:4: 301-311.

Lichtenstein, "Comprehensive review: antitumor necrosis factor agents in inflammatory bowel disease and factors implicated in treatment response," Ther Adv Gastroenterol., 2013, 6(4): 269-293.

Lloyd et al. (2009) "Modelling the human immune response: performance of a 10¹¹ human antibody repertoire against a broad panel of therapeutically relevant antigens" Prot En担n n Des Sel, 22:159-168.

Mitchison, "The dosage requirements for immunological paralysis by soluble proteins," 1968, Immunol. 15:4:509-30.

Mook et al., "In Situ Localization of Gelatinolytic Activity in the Extracellular Matrix of Metastases of Colon Cancer in Rat Liver Using Quenched Fluorogenic DQ-gelatin," J Histochem Cytochem., 2003, 51:821-829.

Moore et al., Antibodies to discontinuous or conformationally sensitive epitopes on the gp120 glycoprotein of human immunodeficiency vims type 1 are highly prevalent in sera of infected humans. J Virol., 1993, 67(2):863-75.

Morgan et al (Oct. 2, 2009) "Designing Biobetter Monoclonal Antibody Therapeutics by Glycoen担 neneering" [offline]. Retrieved from the Internet: http://www.ludger.com/Illicles/ludger-m-00308-intpharmind-2009-biobetter-mAbs.pdf, 5 pages.

Murthy RV, et al. "Legumain expression in relation to clinicopathologic and biological variables in colorectal cancer." Clin Cancer Res. ,2005 11:2293-2299.

NCI Cancer Drug Information, Cetuximab, 2006, http:www.cancer.gov/cancertopics/druginfo/cetuximab downloaded Jul. 18, 2014, 3 pages.

NEB website http://www.neb.com/neb/products/ohd/phd.html, downloaded Jan. 11, 2012.

Nelson et al., "Development trends for human monoclonal antibody therapeutics," Nat Revs., 2010, 9:767:774.

Nielsen et al., "Urokinase plasminogen activator is localized in stromal cells in ductal breast cancer," Lab. Invest., 2001, 81:1485-1501.

Paul, "Fundamental Immunology," Third Edition, New York: Raven Press, 1993, 292-295.

Pirker et al. "Cetuximab plus chemotherapy in patients with advanced non-small-cell lung cancer (FLEX): an open-label randomized phase III trial<" Lancet, 2009, 373: 1525-31.

Roitt et al., "Immunochemical Techniques," Roitt's Essential Immunology, 2001, 6:118-120.

Rudikoff et al., "Single amino acid substitution altering antigen-binding specificity" Proc Natl Acad Sci USA, Mar. 1982, 79:1979-1983.

Schwarz et al., "Mechanisms and principles of N-linked protein glycosylation" Current Opinion In Structural Biology, 2011, 21(5):576-582.

Scott et al. "Searching for peptide ligands with an epitope library," Science, Jul. 1990, 249(4967):386-90.

Segaert et al. "Clinical signs, pathophysiology and management of skin toxicity during therapy withepidermal growth factor receptor inhibitors", Ann Oncol., 2005, 16(9):1425-33.

Sethu et al., "Immunogenicity to Biologies :Mechanisms, prediction and reduction," Arch. Immunol. Ther. Exp., 2012, 60:331-344.

Smith et al., "Phage Display", Chem. Rev., 1997, 97:391-410.

Tabanero et al., "Pharmacogenomic and Pharmacoproteomic Studies of Cetuximab in Metastatic Colorectal Cancer Biomarker Analysis of a Phase I Dose-Escalation," Study. J. Clin. Oncol., 2010, 28(7): 1181-89.

Weigle, "Recent observations and concepts in immunological unresponsiveness and autoimmunity," Clin Exp Immunol., 1971, 9(4):437-47.

Wolbink et al., "Dealing with immunogenicity of biologicals: assessment and clinical relevance," Curr Opin Rheumatol., 2009, 21(3):211-5.

Wright et al., "Antibody variable region glycosylation: position effects on antigen binding and carbohydrate structure" The EMBO Journal, 1991,10(10):2717-2723.

Yan et al. "Antibody Based Therapy for Solid Tumors," The Cancer Journal, 2008, 14 (3): 178-183.

Yang et al., "Generation and characterization of a target-selectively activated antibody against epidermal growth factor receptor with enhanced anti-tumor potency" mAbs, 2015, 7(2):440-450.

Yu et al., "Interaction between Bevacizumab and Murine VEGF-A: A Reassessment" Investigative Ophthalmology & Visual Science, Feb. 2008, 49(2):522-527.

Zeitlin et al. "Enhanced potency of a fucose-free monoclonal antibody being developed as an Ebola vims immunoprotectant" PNAS, Dec. 2011, 108(51):20690-20694.

Zhong et al., "Recent Advances in Glycosylation Modifications in the Context of Therapeutic Glycoproteins" Chapter 10 in Integrative Proteomics. Dr. Hon-Chiu Leung (Ed.), Feb. 2012, InTech; pp. 184-196.

Zon et al., "Phosphorothioate oligonucleotides: chemistry, purification, analysis, scaleup and future directions" Anti-Cancer Drug Design, 1991,6:539-568.

Erster et al., "Site-specific targeting of antibody activity in vivo mediated by disease-associated proteases," J Control Release, Aug. 2012, 161(3):804-812.

Frederiks et al., "Metabolic Mapping of Proteinase Activity with Emphasis on In Situ Zymography of Gelatinases: Review and Protocols," Journal of Histochemistry & Cytochemistry, Jun. 2004, 52(6):711-722.

Snoek-van Beurden et al., "Zymographic techniques for the analysis of matrix metalloproteinases and their inhibitors," BioTechniques, Jan. 2005, 38(1):73-83.

Tsai et al., "Matriptase and survivin expression associated with tumor progression and malignant potential in breast cancer of Chinese women: Tissue microarray analysis of immunostaining scores with clinicopathological parameters," Disease Markers, Jan. 2008, 24(2),89-99.

Yan et al., "In Situ Zymography: A Molecular Pathology Technique to Localize Endogenous Protease Activity in Tissue Sections," Vet Pathol, May 2003, 40(3):227-236.

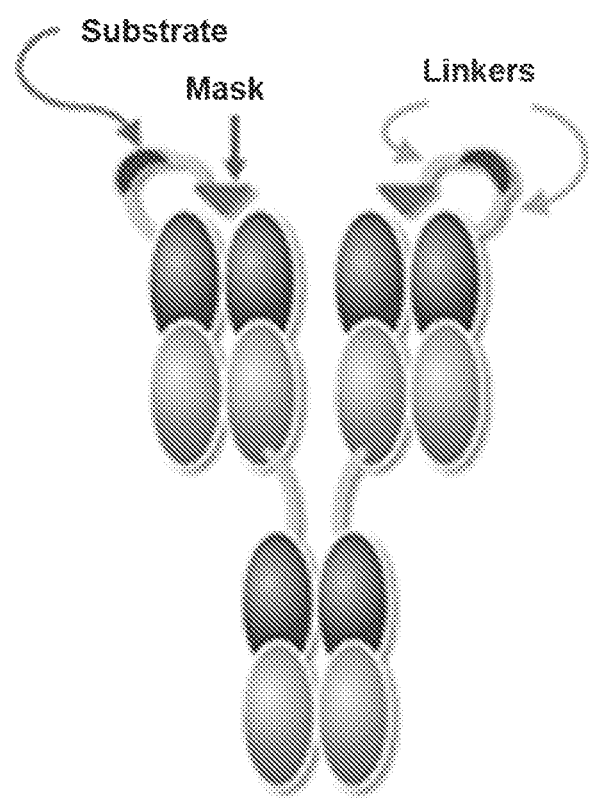

METHOD OF USING AN ANTI-EPIDERMAL GROWTH FACTOR RECEPTOR (EGFR) ACTIVATABLE ANTIBODY TO DETECT THE PRESENCE OR ABSENCE OF A CLEAVING AGENT AND EGFR

RELATED APPLICATIONS

This application is a divisional of U.S. patent application Ser. No. 16/712,422, filed Dec. 12, 2019, which is a divisional of U.S. patent application Ser. No. 15/382,890, now U.S. Pat. No. 10,553,053, filed Dec. 19, 2016, which is a divisional of U.S. patent application Ser. No. 14/528,180, now U.S. Pat. No. 9,540,440, filed Oct. 30, 2014, now issued U.S. Pat. No. 9,540,440, granted Jan. 10, 2017, which claims the benefit of U.S. Provisional Application No. 61/897,385, filed Oct. 30, 2013; U.S. Provisional Application No. 61/897,391, filed Oct. 30, 2013; U.S. Provisional Application No. 61/897,418, filed Oct. 30, 2013; U.S. Provisional Application No. 61/897,442, filed Oct. 30, 2013; and U.S. Provisional Application No. 61/897,465, filed Oct. 30, 2013 the contents of each of which are incorporated herein by reference in their entireties.

INCORPORATION OF SEQUENCE LISTING

The contents of the text file named "45325-0033004_SequenceListing.txt", which was created on Nov. 18, 2021 and is 68.1 KB in size, are hereby incorporated by reference in their entirety.

FIELD OF THE INVENTION

The invention relates generally to activatable antibodies that specifically bind to epidermal growth factor receptor (EGFR), to conjugated activatable antibodies that specifically bind to EGFR, and to methods of making and using these anti-EGFR activatable antibodies and/or conjugated anti-EGFR activatable antibodies in a variety of therapeutic, diagnostic and prophylactic indications.

BACKGROUND OF THE INVENTION

Antibody-based therapies have proven effective treatments for some diseases but in some cases, toxicities due to broad target expression have limited their therapeutic effectiveness. In addition, antibody-based therapeutics have exhibited other limitations such as rapid clearance from the circulation following administration.

In the realm of small molecule therapeutics, strategies have been developed to provide prodrugs of an active chemical entity. Such prodrugs are administered in a relatively inactive (or significantly less active) form. Once administered, the prodrug is metabolized in vivo into the active compound. Such prodrug strategies can provide for increased selectivity of the drug for its intended target and for a reduction of adverse effects.

Accordingly, there is a continued need in the field of antibody-based therapeutics for antibodies that mimic the desirable characteristics of the small molecule prodrug.

SUMMARY OF THE INVENTION

The activatable antibodies provided herein, in an uncleaved state, include a masked light chain that includes at least an antibody or antigen-binding fragment thereof (AB) that specifically binds Epidermal Growth Factor Receptor (EGFR) coupled to a masking moiety (MM) via a cleavable moiety (CM) that includes a substrate for a protease, such that coupling of the MM to the AB reduces the ability of the AB to bind EGFR. In an activated state, e.g., a cleaved state, the activatable antibodies bind EGFR. In an uncleaved state, e.g., non-activated state, the activatable antibodies provided herein include an antibody or an antigen binding fragment thereof (AB) that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22). In some embodiments, the two linking peptides need not be identical to each other. In some embodiments, the activatable antibodies provided herein, in an uncleaved state, include a masked light chain that includes or is derived from an amino acid sequence selected from the group consisting of SEQ ID NO: 4, SEQ ID NO: 6, SEQ ID NO: 8, SEQ ID NO: 10, and SEQ ID NO: 12.

In some embodiments, the activatable antibodies provided herein include an AB that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQSGQ (SEQ ID NO: 14). In some embodiments, the two linking peptides need not be identical to each other. In some embodiments, the activatable antibodies provided herein, in an uncleaved state, include a masked light chain that includes or is derived from the amino acid sequence of SEQ ID NO: 4. In some embodiments, the activatable antibodies provided herein, in an uncleaved state, include a heavy chain that includes or is derived from the amino acid sequence of SEQ ID NO: 2 and a masked light chain that includes or is derived from the amino acid sequence of SEQ ID NO: 4. In some embodiments, the activatable antibodies provided herein, in an uncleaved state, include a heavy chain that includes or is derived from the amino acid sequence of SEQ ID NO: 34 and a masked light chain that includes or is derived from the amino acid sequence of SEQ ID NO: 4. In some embodiments, the activatable antibodies provided herein, in an uncleaved state, include a heavy chain that includes or is derived from the amino acid sequence of SEQ ID NO: 36 and a masked light chain that includes or is derived from the amino acid sequence of SEQ ID NO: 4.

In some embodiments, the activatable antibodies provided herein include an AB that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence QSGQ (SEQ ID NO: 16). In some embodiments, the two linking peptides need not be identical to each other. In some embodiments, the activatable antibodies provided herein, in an uncleaved state, include a masked light chain that includes or is derived from the amino acid sequence of SEQ ID NO: 6. In some embodiments, the activatable antibodies provided herein, in an uncleaved state, include a heavy chain that includes or is derived from the amino acid sequence of SEQ ID NO: 2 and a masked light chain that includes or is derived from the amino acid sequence of SEQ ID NO: 6. In some embodiments, the activatable antibodies provided herein, in an uncleaved state, include a heavy chain that includes or is derived from the amino acid sequence of SEQ ID NO: 34 and a masked light chain that includes or is derived from the amino acid sequence of SEQ ID NO: 6. In some embodiments, the activatable antibodies provided herein, in an uncleaved state, include a heavy chain that includes or is derived from the amino acid sequence of SEQ ID NO: 36 and a masked light chain that includes or is derived from the amino acid sequence of SEQ ID NO: 6.

In some embodiments, the activatable antibodies provided herein include an AB that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence SGQ (SEQ ID NO: 18). In some embodiments, the two linking peptides need not be identical to each other. In some embodiments, the activatable antibodies provided herein, in an uncleaved state, include a masked light chain that includes or is derived from the amino acid sequence of SEQ ID NO: 8. In some embodiments, the activatable antibodies provided herein, in an uncleaved state, include a heavy chain that includes or is derived from the amino acid sequence of SEQ ID NO: 2 and a masked light chain that includes or is derived from the amino acid sequence of SEQ ID NO: 8. In some embodiments, the activatable antibodies provided herein, in an uncleaved state, include a heavy chain that includes or is derived from the amino acid sequence of SEQ ID NO: 34 and a masked light chain that includes or is derived from the amino acid sequence of SEQ ID NO: 8. In some embodiments, the activatable antibodies provided herein, in an uncleaved state, include a heavy chain that includes or is derived from the amino acid sequence of SEQ ID NO: 36 and a masked light chain that includes or is derived from the amino acid sequence of SEQ ID NO: 8.

In some embodiments, the activatable antibodies provided herein include an AB that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQ (SEQ ID NO: 20). In some embodiments, the two linking peptides need not be identical to each other. In some embodiments, the activatable antibodies provided herein, in an uncleaved state, include a masked light chain that includes or is derived from the amino acid sequence of SEQ ID NO: 10. In some embodiments, the activatable antibodies provided herein, in an uncleaved state, include a heavy chain that includes or is derived from the amino acid sequence of SEQ ID NO: 2 and a masked light chain that includes or is derived from the amino acid sequence of SEQ ID NO: 10. In some embodiments, the activatable antibodies provided herein, in an uncleaved state, include a heavy chain that includes or is derived from the amino acid sequence of SEQ ID NO: 34 and a masked light chain that includes or is derived from the amino acid sequence of SEQ ID NO: 10. In some embodiments, the activatable antibodies provided herein, in an uncleaved state, include a heavy chain that includes or is derived from the amino acid sequence of SEQ ID NO: 36 and a masked light chain that includes or is derived from the amino acid sequence of SEQ ID NO: 10.

In some embodiments, the activatable antibodies provided herein include an AB that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence Q (SEQ ID NO: 22). In some embodiments, the two linking peptides need not be identical to each other. In some embodiments, the activatable antibodies provided herein, in an uncleaved state, include a masked light chain that includes or is derived from the amino acid sequence of SEQ ID NO: 12. In some embodiments, the activatable antibodies provided herein, in an uncleaved state, include a heavy chain that includes or is derived from the amino acid sequence of SEQ ID NO: 2 and a masked light chain that includes or is derived from the amino acid sequence of SEQ ID NO: 12. In some embodiments, the activatable antibodies provided herein, in an uncleaved state, include a heavy chain that includes or is derived from the amino acid sequence of SEQ ID NO: 34 and a masked light chain that includes or is derived from the amino acid sequence of SEQ ID NO: 12. In some embodiments, the activatable antibodies provided herein, in an uncleaved state, include a heavy chain that includes or is derived from the amino acid sequence of SEQ ID NO: 36 and a masked light chain that includes or is derived from the amino acid sequence of SEQ ID NO: 12.

The invention also provides conjugated activatable antibodies in which an anti-EGFR activatable antibody provided herein is conjugated to one or more additional agents. In an activated state, e.g., a cleaved state, the conjugated activatable antibodies bind EGFR. In some embodiments, the conjugated activatable antibody in an uncleaved state includes a masked light chain that includes or is derived from an amino acid sequence selected from the group consisting of SEQ ID NO: 4, SEQ ID NO: 6, SEQ ID NO: 8, SEQ ID NO: 10, and SEQ ID NO: 12.

In some embodiments, the conjugated activatable antibody in an uncleaved state includes a masked light chain that includes or is derived from an amino acid sequence selected from the group consisting of SEQ ID NO: 4.

In some embodiments, the conjugated activatable antibody in an uncleaved state includes a masked light chain that includes or is derived from an amino acid sequence selected from the group consisting of SEQ ID NO: 6.

In some embodiments, the conjugated activatable antibody in an uncleaved state includes a masked light chain that includes or is derived from an amino acid sequence selected from the group consisting of SEQ ID NO: 8.

In some embodiments, the conjugated activatable antibody in an uncleaved state includes a masked light chain that includes or is derived from an amino acid sequence selected from the group consisting of SEQ ID NO: 10.

In some embodiments, the conjugated activatable antibody in an uncleaved state includes a masked light chain that includes or is derived from an amino acid sequence selected from the group consisting of SEQ ID NO: 12.

The activatable anti-EGFR antibodies and the conjugated activatable anti-EGFR antibodies provided herein are stable in circulation, activated at intended sites of therapy and/or diagnosis but not in other tissue(s), e.g., normal tissue, healthy tissue, and/or diseased tissue at a site not intended for therapy, and, when activated, exhibit binding to EGFR that is at least comparable to the corresponding, unmodified antibody.

In some embodiments of the activatable antibody and/or conjugated activatable antibody, at least one of LP1 or LP2 includes an amino acid sequence selected from the group consisting of $(GS)_n$, $(GGS)_n$, $(GSGGS)_n$ (SEQ ID NO: 66) and $(GGGS)_n$ (SEQ ID NO: 67), where n is an integer of at least one. In some embodiments of the activatable antibody and/or conjugated activatable antibody, at least one of LP1 or LP2 includes an amino acid sequence selected from the group consisting of GGSG (SEQ ID NO: 68), GGSGG (SEQ ID NO: 69), GSGSG (SEQ ID NO: 70), GSGGG (SEQ ID NO: 71), GGGSG (SEQ ID NO: 72), and GSSSG (SEQ ID NO: 73).

In some embodiments of the activatable antibody and/or conjugated activatable antibody, LP1 includes the amino acid sequence GSSGGSGGSGGSG (SEQ ID NO: 26).

In some embodiments of the activatable antibody and/or conjugated activatable antibody, LP2 includes the amino acid sequence GSSGT (SEQ ID NO: 30) or GSSG (SEQ ID NO: 65).

In some embodiments of the activatable antibody and/or conjugated activatable antibody, the AB is a monoclonal antibody, domain antibody, single chain, Fab fragment, a F(ab')2 fragment, a scFv, a scab, a dAb, a single domain heavy chain antibody, or a single domain light chain antibody. In some embodiments, such an antibody or immunologically active fragment thereof that binds EGFR is a mouse, chimeric, humanized or fully human monoclonal antibody.

In some embodiments of the activatable antibody and/or conjugated activatable antibody, the AB has an equilibrium dissociation constant of about 100 nM or less for binding to EGFR.

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22).

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQSGQ (SEQ ID NO: 14).

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence QSGQ (SEQ ID NO: 16).

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence SGQ (SEQ ID NO: 18).

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQ (SEQ ID NO: 20).

In some embodiments, the activatable antibody and/or conjugated activatable antibody includes an AB that specifically binds to EGFR that includes a heavy chain amino acid sequence that includes SEQ ID NO: 2, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence Q (SEQ ID NO: 22).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQSGQ (SEQ ID NO: 14).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence QSGQ (SEQ ID NO: 16).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence SGQ (SEQ ID NO: 18).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQ (SEQ ID NO: 20).

In some embodiments, the activatable antibody and/or conjugated activatable antibody includes an AB that specifically binds to EGFR that includes a heavy chain amino acid sequence that includes SEQ ID NO: 34, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence Q (SEQ ID NO: 22).

In some embodiments, the activatable antibody and/or conjugated activatable antibody includes an AB that specifically binds to EGFR that includes a heavy chain amino acid sequence that includes SEQ ID NO: 36, and a light chain amino acid sequence that includes SEQ ID NO: 32, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22).

In some embodiments, the activatable antibody and/or conjugated activatable antibody includes an AB that specifically binds to EGFR that includes a heavy chain amino acid sequence that includes SEQ ID NO: 10, and a light chain amino acid sequence that includes SEQ ID NO: 36, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQSGQ (SEQ ID NO: 14).

In some embodiments, the activatable antibody and/or conjugated activatable antibody includes an AB that specifically binds to EGFR that includes a heavy chain amino acid sequence that includes SEQ ID NO: 10, and a light chain amino acid sequence that includes SEQ ID NO: 36, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence QSGQ (SEQ ID NO: 16).

In some embodiments, the activatable antibody and/or conjugated activatable antibody includes an AB that specifically binds to EGFR that includes a heavy chain amino acid sequence that includes SEQ ID NO: 10, and a light chain amino acid sequence that includes SEQ ID NO: 36, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence SGQ (SEQ ID NO: 18).

In some embodiments, the activatable antibody and/or conjugated activatable antibody includes an AB that specifically binds to EGFR that includes a heavy chain amino acid sequence that includes SEQ ID NO: 10, and a light chain amino acid sequence that includes SEQ ID NO: 36, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence GQ (SEQ ID NO: 20).

In some embodiments, the activatable antibody and/or conjugated activatable antibody includes an AB that specifically binds to EGFR that includes a heavy chain amino acid sequence that includes SEQ ID NO: 10, and a light chain amino acid sequence that includes SEQ ID NO: 36, wherein the activatable antibody and/or conjugated activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence includes the amino acid sequence Q (SEQ ID NO: 22).

In some embodiments, the activatable antibody and/or conjugated activatable antibody in an uncleaved state includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12. In some embodiments, the activatable antibody and/or conjugated activatable antibody in an uncleaved state includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 34, and SEQ ID NO: 36, and a masked light chain amino acid sequence that is at least 90%, 91%, 92%, 93%, 94%, 95%, 96%, 97%, 98% or 99% identical to an amino acid sequence selected from the group consisting of SEQ ID NO: 4, SEQ ID NO: 6, SEQ ID NO: 8, SEQ ID NO: 10, and SEQ ID NO: 12.

In some embodiments, the activatable antibody and/or conjugated activatable antibody in an uncleaved state includes a heavy chain that includes the amino acid sequence of SEQ ID NO: 2, and a masked light chain that includes the amino acid sequence of SEQ ID NO: 4, SEQ ID NO: 6, SEQ ID NO: 8, SEQ ID NO: 10, and SEQ ID NO: 12. In some embodiments, the activatable antibody and/or conjugated activatable antibody in an uncleaved state includes a heavy chain amino acid sequence that is at least 90%, 91%, 92%, 93%, 94%, 95%, 96%, 97%, 98% or 99% identical to the amino acid of SEQ ID NO: 2, and a masked light chain amino acid sequence that is at least 90%, 91%, 92%, 93%, 94%, 95%, 96%, 97%, 98% or 99% identical to the amino acid sequence of SEQ ID NO: 4, SEQ ID NO: 6, SEQ ID NO: 8, SEQ ID NO: 10, and SEQ ID NO: 12.

In some embodiments, the activatable antibody and/or conjugated activatable antibody in an uncleaved state includes a heavy chain that includes the amino acid sequence of SEQ ID NO: 34, and a masked light chain that includes the amino acid sequence of SEQ ID NO: 4, SEQ ID NO: 6, SEQ ID NO: 8, SEQ ID NO: 10, and SEQ ID NO: 12. In some embodiments, the activatable antibody and/or conjugated activatable antibody in an uncleaved state includes a heavy chain amino acid sequence that is at least 90%, 91%, 92%, 93%, 94%, 95%, 96%, 97%, 98% or 99% identical to the amino acid of SEQ ID NO: 6, and a masked light chain amino acid sequence that is at least 90%, 91%, 92%, 93%, 94%, 95%, 96%, 97%, 98% or 99% identical to the amino acid sequence of SEQ ID NO: 4, SEQ ID NO: 6, SEQ ID NO: 8, SEQ ID NO: 10, and SEQ ID NO: 12.

In some embodiments, the activatable antibody and/or conjugated activatable antibody in an uncleaved state includes a heavy chain that includes the amino acid sequence of SEQ ID NO: 36, and a masked light chain that includes the amino acid sequence of SEQ ID NO: 4, SEQ ID NO: 6, SEQ ID NO: 8, SEQ ID NO: 10, and SEQ ID NO: 12. In some embodiments, the activatable antibody and/or conjugated activatable antibody in an uncleaved state includes a heavy chain amino acid sequence that is at least 90%, 91%, 92%, 93%, 94%, 95%, 96%, 97%, 98% or 99% identical to the amino acid of SEQ ID NO: 36, and a masked light chain amino acid sequence that is at least 90%, 91%, 92%, 93%, 94%, 95%, 96%, 97%, 98% or 99% identical to the amino acid sequence of SEQ ID NO: 4, SEQ ID NO: 6, SEQ ID NO: 8, SEQ ID NO: 10, and SEQ ID NO: 12.

In some embodiments, the activatable antibody and/or conjugated activatable antibody in an uncleaved state includes a combination of a heavy chain amino acid sequence and a masked light chain amino acid sequence selected from the group consisting of (i) a heavy chain sequence of SEQ ID NO: 2 and a masked light chain amino acid sequence of SEQ ID NO: 4, (ii) a heavy chain sequence of SEQ ID NO: 2 and a masked light chain amino acid sequence of SEQ ID NO: 6, (iii) a heavy chain sequence of SEQ ID NO: 2 and a masked light chain amino acid sequence of SEQ ID NO: 8, (iv) a heavy chain sequence of SEQ ID NO: 2 and a masked light chain amino acid sequence of SEQ ID NO: 10, (v) a heavy chain sequence of SEQ ID NO: 2 and a masked light chain amino acid sequence of SEQ ID NO: 12, (vi) a heavy chain sequence of SEQ ID NO: 34 and a masked light chain amino acid sequence of SEQ ID NO: 4, (vii) a heavy chain sequence of SEQ ID NO: 34 and a masked light chain amino acid sequence of SEQ ID NO: 6, (viii) a heavy chain sequence of SEQ ID NO: 34 and a masked light chain amino acid sequence of SEQ ID NO: 8, (ix) a heavy chain sequence of SEQ ID NO: 34 and a masked light chain amino acid sequence of SEQ ID NO: 10, (x) a heavy chain sequence of SEQ ID NO: 34 and a masked light chain amino acid sequence of SEQ ID NO: 12, (xi) a heavy chain sequence of SEQ ID NO: 36 and a masked light chain amino acid sequence of SEQ ID NO: 4, (xii) a heavy chain sequence of SEQ ID NO: 36 and a masked light chain amino acid sequence of SEQ ID NO: 6, (xiii) a heavy chain sequence of SEQ ID NO: 36 and a masked light chain amino acid sequence of SEQ ID NO: 8, (xiv) a heavy chain sequence of SEQ ID NO: 36 and a masked light chain amino acid sequence of SEQ ID NO: 10, and (xv) a heavy chain sequence of SEQ ID NO: 36 and a masked light chain amino acid sequence of SEQ ID NO: 12.

In some embodiments, the activatable antibody and/or conjugated activatable antibody in an uncleaved state includes a combination of a heavy chain amino acid sequence and a masked light chain amino acid sequence selected from the group consisting of (i) a heavy chain sequence of SEQ ID NO: 2 and a masked light chain amino acid sequence of SEQ ID NO: 4, (ii) a heavy chain sequence of SEQ ID NO: 2 and a masked light chain amino acid sequence of SEQ ID NO: 6, (iii) a heavy chain sequence of SEQ ID NO: 2 and a masked light chain amino acid sequence of SEQ ID NO: 8, (iv) a heavy chain sequence of SEQ ID NO: 2 and a masked light chain amino acid sequence of SEQ ID NO: 10, (v) a heavy chain sequence of SEQ ID NO: 2 and a masked light chain amino acid sequence of SEQ ID NO: 12, (vi) a heavy chain sequence of SEQ ID NO: 34 and a masked light chain amino acid sequence of SEQ ID NO: 4, (vii) a heavy chain sequence of SEQ ID NO: 34 and a masked light chain amino acid sequence of SEQ ID NO: 6, (viii) a heavy chain sequence of SEQ ID NO: 34 and a masked light chain amino acid sequence of SEQ ID NO: 8, (ix) a heavy chain sequence of SEQ ID NO: 34 and a masked light chain amino acid sequence of SEQ ID NO: 10, (x) a heavy chain sequence of SEQ ID NO: 34 and a masked light chain amino acid sequence of SEQ ID NO: 12, (xi) a heavy chain sequence of SEQ ID NO: 36 and a masked light chain amino acid sequence of SEQ ID NO: 4, (xii) a heavy chain sequence of SEQ ID NO: 36 and a masked light chain amino acid sequence of SEQ ID NO: 6, (xiii) a heavy chain sequence of SEQ ID NO: 36 and a masked light chain amino acid sequence of SEQ ID NO: 8, (xiv) a heavy chain sequence of SEQ ID NO: 36 and a masked light chain amino acid sequence of SEQ ID NO: 10, and (xv) a heavy chain sequence of SEQ ID NO: 36 and a masked light chain amino acid sequence of SEQ ID NO: 12.

In some embodiments of the activatable antibody and/or conjugated activatable antibody, the MM includes the amino acid sequence CISPRGCPDGPYVMY (SEQ ID NO: 24) and is a polypeptide of no more than 40 amino acids long.

In some embodiments of the activatable antibody and/or conjugated activatable antibody, the MM has an equilibrium dissociation constant for binding to the AB that is greater than the equilibrium dissociation constant of the AB to EGFR.

In some embodiments of the activatable antibody and/or conjugated activatable antibody, the MM has an equilibrium dissociation constant for binding to the AB that is no more than the equilibrium dissociation constant of the AB to EGFR.

In some embodiments of the activatable antibody and/or conjugated activatable antibody, the MM does not interfere or compete with the AB of the activatable antibody in a cleaved state for binding to EGFR.

In some embodiments of the activatable antibody and/or conjugated activatable antibody, the coupling of the MM to the AB reduces the ability of the AB to bind EGFR such that the dissociation constant ($K_d$) of the AB when coupled to the MM towards EGFR is at least 20 times greater than the $K_d$ of the AB when not coupled to the MM towards EGFR. In some embodiments of the activatable antibody and/or conjugated activatable antibody, the coupling of the MM to the AB reduces the ability of the AB to bind EGFR such that the dissociation constant ($K_d$) of the AB when coupled to the MM towards EGFR is at least 40 times greater than the $K_d$ of the AB when not coupled to the MM towards EGFR. In some embodiments of the activatable antibody and/or conjugated activatable antibody, the coupling of the MM to the AB reduces the ability of the AB to bind EGFR such that the dissociation constant ($K_d$) of the AB when coupled to the MM towards EGFR is at least 50 times greater than the $K_d$ of the AB when not coupled to the MM towards EGFR. In some embodiments of the activatable antibody and/or conjugated activatable antibody, the coupling of the MM to the AB reduces the ability of the AB to bind EGFR such that the $K_d$ of the AB when coupled to the MM towards EGFR is at least 100 times greater than the $K_d$ of the AB when not coupled to the MM towards EGFR. In some embodiments of the activatable antibody and/or conjugated activatable antibody, the coupling of the MM to the AB reduces the ability of the AB to bind EGFR such that the $K_d$ of the AB when coupled to the MM towards EGFR is at least 1000 times greater than the $K_d$ of the AB when not coupled to the MM towards EGFR. In some embodiments of the activatable antibody and/or conjugated activatable antibody, the coupling of the MM to the AB reduces the ability of the AB to bind EGFR such that the $K_d$ of the AB when coupled to the MM towards EGFR is at least 10,000 times greater than the $K_d$ of the AB when not coupled to the MM towards EGFR.

In some embodiments of the activatable antibody and/or conjugated activatable antibody, in the presence of EGFR, the MM reduces the ability of the AB to bind EGFR by at least 90% when the CM is uncleaved, as compared to when the CM is cleaved when assayed in vitro using a target displacement assay such as, for example, the assay described in PCT Publication Nos. WO 2009/025846 and WO 2010/081173.

In some embodiments of the activatable antibody and/or conjugated activatable antibody, the CM is a substrate for a protease. In some embodiments of the activatable antibody and/or conjugated activatable antibody, the protease is co-localized with EGFR in a tissue, and the protease cleaves the CM when the activatable antibody and/or conjugated activatable antibody is exposed to the protease. In some embodiments, the protease is not active or is significantly less active in tissues that do not significantly express EGFR. In some embodiments, the protease is not active or is significantly less active in healthy, e.g., non-diseased tissues. In some embodiments, the protease is not active or is significantly less active in diseased tissues not intended for therapy.

In some embodiments, the CM is positioned in the activatable antibody and/or conjugated activatable antibody such that in the uncleaved state, binding to EGFR by the activatable antibody is reduced to occur with an equilibrium dissociation constant that is at least 20-fold greater than the equilibrium dissociation constant of an unmodified AB binding to EGFR, and whereas the AB of the activatable antibody and/or the conjugated activatable antibody in the cleaved state binds EGFR.

In some embodiments, the CM is positioned in the activatable antibody and/or the conjugated activatable antibody such that in the uncleaved state, binding to EGFR by the activatable antibody is reduced to occur with an equilibrium dissociation constant that is at least 40-fold greater than the equilibrium dissociation constant of an unmodified AB binding to EGFR, and whereas the AB of the activatable antibody and/or the conjugated activatable antibody in the cleaved state binds EGFR.

In some embodiments, the CM is positioned in the activatable antibody and/or the conjugated activatable antibody such that in the uncleaved state, binding to EGFR by the activatable antibody is reduced to occur with an equilibrium dissociation constant that is at least 50-fold greater than the equilibrium dissociation constant of an unmodified AB binding to EGFR, and whereas the AB of the activatable antibody and/or the conjugated activatable antibody in the cleaved state binds EGFR.

In some embodiments, the CM is positioned in the activatable antibody and/or the conjugated activatable antibody such that in the uncleaved state, binding to EGFR by the activatable antibody is reduced to occur with an equilibrium dissociation constant that is at least 100-fold greater than the equilibrium dissociation constant of an unmodified AB binding to EGFR, and whereas the AB of the activatable antibody and/or the conjugated activatable antibody in the cleaved state binds EGFR.

In some embodiments, the CM is positioned in the activatable antibody and/or the conjugated activatable antibody such that in the uncleaved state, binding to EGFR by the activatable antibody is reduced to occur with an equilibrium dissociation constant that is at least 200-fold greater than the equilibrium dissociation constant of an unmodified AB binding to EGFR, and whereas the AB of the activatable antibody and/or the conjugated activatable antibody in the cleaved state binds EGFR.

In some embodiments, the CM includes the amino acid sequence LSGRSDNH (SEQ ID NO: 28) and is a polypeptide of up to 15 amino acids in length.

In some embodiments, the CM is a substrate for an enzyme selected from the group consisting of uPA, legumain and MT-SP1. In some embodiments, the enzyme comprises uPA. In some embodiments, the enzyme comprises legumain. In some embodiments, the enzyme comprises MT-SP1.

In some embodiments, the activatable antibody also includes an agent conjugated to the AB. In some embodiments, the agent is a therapeutic agent. In some embodiments, the agent is an antineoplastic agent. In some embodiments, the agent is a toxin or fragment thereof. As used herein, a fragment of a toxin is a fragment that retains toxic activity. In some embodiments, the agent is conjugated to the AB via a cleavable linker. In some embodiments, the agent is conjugated to the AB via a linker that includes at least one MMP-cleavable substrate sequence. In some embodiments, the agent is conjugated to the AB via a noncleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the agent is an agent selected from the group listed in Table 1. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the agent is conjugated to the AB via a linker. In some embodiments, the linker is a cleavable linker. In some embodiments, the linker is selected from the group consisting of the linkers shown in Tables 2 and 3.

In some embodiments, the activatable antibody also includes a detectable moiety. In some embodiments, the detectable moiety is a diagnostic agent. In some embodiments, the detectable moiety is a conjugatable detection reagent. In some embodiments, the detectable moiety is, for example, a fluorescent label or radioisotope. In some embodiments, the detectable moiety is an imaging agent, a contrasting agent, an enzyme, a fluorescent label, a chromophore, a dye, one or more metal ions, and/or a ligand-based label.

In some embodiments, the serum half-life of the activatable antibody and/or conjugated activatable antibody is longer than that of the corresponding antibody; e.g., the pK of the activatable antibody and/or conjugated activatable antibody is longer than that of the corresponding antibody. In some embodiments, the serum half-life of the activatable antibody and/or conjugated activatable antibody is similar to that of the corresponding antibody. In some embodiments, the serum half-life of the activatable antibody and/or conjugated activatable antibody is at least 15 days when administered to an organism. In some embodiments, the serum half-life of the activatable antibody and/or conjugated activatable antibody is at least 12 days when administered to an organism. In some embodiments, the serum half-life of the activatable antibody and/or conjugated activatable antibody is at least 11 days when administered to an organism. In some embodiments, the serum half-life of the activatable antibody and/or conjugated activatable antibody is at least 10 days when administered to an organism. In some embodiments, the serum half-life of the activatable antibody and/or conjugated activatable antibody is at least 9 days when administered to an organism. In some embodiments, the serum half-life of the activatable antibody and/or conjugated activatable antibody is at least 8 days when administered to an organism. In some embodiments, the serum half-life of the activatable antibody and/or conjugated activatable antibody is at least 7 days when administered to an organism. In some embodiments, the serum half-life of the activatable antibody and/or conjugated activatable antibody is at least 6 days when administered to an organism. In some examples of any of these activatable antibody and/or conjugated activatable antibody embodiments, the serum half-life of the activatable antibody and/or conjugated activatable antibody is at least 5 days when administered to an organism. In some embodiments, the serum half-life of the activatable antibody and/or conjugated activatable antibody is at least 4 days when administered to an organism. In some embodiments, the serum half-life of the activatable antibody and/or conjugated activatable antibody is at least 3 days when administered to an organism. In some embodiments, the serum half-life of the activatable antibody and/or conjugated activatable antibody is at least 2 days when administered to an organism. In some embodiments, the serum half-life of the activatable antibody and/or conjugated activatable antibody is at least 24 hours when administered to an organism. In some embodiments, the serum half-life of the activatable antibody and/or conjugated activatable antibody is at least 20 hours when administered to an organism. In some embodiments, the serum half-life of the activatable antibody and/or conjugated activatable antibody is at least 18 hours when administered to an organism. In some embodiments, the serum half-life of the activatable antibody and/or conjugated activatable antibody is at least 16 hours when administered to an organism. In some embodiments, the serum half-life of the activatable antibody and/or conjugated activatable antibody is at least 14 hours when administered to an organism. In some embodiments, the serum half-life of the activatable antibody and/or conjugated activatable antibody is at least 12 hours when administered to an organism. In some embodiments, the serum half-life of the activatable antibody and/or conjugated activatable antibody is at least 10 hours when administered to an organism. In some embodiments, the serum half-life of the activatable antibody and/or conjugated activatable antibody is at least 8 hours when administered to an organism. In some embodiments, the serum half-life of the activatable antibody and/or conjugated activatable antibody is at least 6 hours when administered to an organism. In some embodiments, the serum half-life of the activatable antibody and/or conjugated activatable antibody is at least 4 hours when administered to an organism. In some embodiments, the serum half-life of the activatable antibody and/or conjugated activatable antibody is at least 3 hours when administered to an organism.

In some embodiments, the activatable anti-EGFR antibody is monospecific. In some embodiments, the activatable anti-EGFR antibody is multispecific, e.g., by way of non-limiting example, bispecific or trifunctional. In some embodiments, the activatable anti-EGFR antibody is formulated as part of a activatable antibody and/or conjugated activatable antibody, such as a T-cell engaging activatable antibody and/or conjugated activatable antibody. In some embodiments, the activatable anti-EGFR antibody is formulated as part of a pro-Bispecific T Cell Engager (BITE) molecule. In some embodiments, the activatable anti-EGFR antibody is formulated as part of a pro-Chimeric Antigen Receptor (CAR) modified T cell or other engineered receptor.

The invention also provides an isolated nucleic acid molecule encoding an activatable anti-EGFR antibody described herein, as well as vectors that include these isolated nucleic acid sequences. The invention provides methods of producing an activatable antibody by culturing a cell under conditions that lead to expression of the activatable antibody, wherein the cell includes such a vector.

The invention also provides a method of manufacturing an activatable antibody that in an activated state binds Epidermal Growth Factor Receptor (EGFR) by (a) culturing a cell comprising a nucleic acid construct that encodes the activatable antibody under conditions that lead to expression of the activatable antibody, wherein the activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12; and (b) recovering the activatable antibody.

The invention also provides a method of manufacturing a conjugated activatable antibody that in an activated state binds Epidermal Growth Factor Receptor (EGFR) by (a) culturing a cell comprising a nucleic acid construct that encodes the activatable antibody under conditions that lead to expression of the activatable antibody, wherein the activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12; (b) recovering the activatable antibody; and (c) conjugating the activatable antibody to one or more additional agents.

The invention provides methods of treating, preventing and/or delaying the onset or progression of, or alleviating a symptom of an indication, e.g., disease or disorder, associated with aberrant expression and/or activity of EGFR, e.g., an EGFR-related disorder or EGFR-related disease, in a subject using a therapeutic molecule, e.g., activatable antibodies that bind EGFR and/or conjugated activatable antibodies that bind EGFR, particularly activatable antibodies and/or conjugated activatable antibodies that bind and neutralize or otherwise inhibit at least one biological activity of EGFR and/or EGFR-mediated signaling.

In some embodiments, the indication, e.g., disease or disorder, associated with aberrant expression and/or activity of EGFR is a cancer. In some embodiments, the cancer is a breast cancer, e.g., by way of non-limiting example, the breast cancer is a triple-negative breast cancer. In some embodiments, the cancer is a triple-negative breast cancer. In some embodiments, the cancer is colorectal cancer. In some embodiments, the cancer is gastric cancer. In some embodiments, the cancer is glioblastoma. In some embodiments, the cancer is a head and neck cancer, e.g., by way of non-limiting example, esophageal cancer. In some embodiments, the cancer is an esophageal cancer. In some embodiments, the cancer is a lung cancer, e.g., by way of non-limiting example, non-small cell lung cancer. In some embodiments, the cancer is a non-small cell lung cancer. In some embodiments, the cancer is ovarian/endometrial cancer. In some embodiments, the cancer is ovarian cancer. In some embodiments, the cancer is endometrial cancer. In some embodiments, the cancer is pancreatic cancer. In some embodiments, the cancer is prostate cancer. In some embodiments, the cancer is a renal cancer. In some embodiments, the cancer is a sarcoma, e.g., by way of non-limiting example, osteosarcoma. In some embodiments, the cancer is an osteosarcoma. In some embodiments, the cancer is a skin cancer, e.g., by way of non-limiting example, squamous cell cancer, basal cell carcinoma, and/or melanoma. In some embodiments, the cancer is a squamous cell cancer. In some embodiments, the cancer is a basal cell carcinoma. In some embodiments, the cancer is a melanoma.

In some embodiments, the indication, e.g., disease or disorder, associated with aberrant expression and/or activity of EGFR is an inflammatory disorder and/or an autoimmune disease. In some embodiments, the inflammatory and/or autoimmune disease is psoriasis.

The therapeutic molecule, e.g., activatable anti-EGFR antibody and/or conjugated anti-EGFR activatable antibody, can be administered at any stage of the disease. For example, a therapeutic molecule can be administered to a patient suffering cancer of any stage, from early to metastatic. For example, a therapeutic molecule can be administered to a patient suffering from an inflammatory disorder and/or autoimmune disease of any stage, from early onset to an advanced stage. It is to be understood that the terms subject and patient are used interchangeably herein.

The therapeutic molecules, e.g. activatable anti-EGFR antibodies and/or conjugated activatable anti-EGFR antibodies, are also useful in other therapeutic indications and treatment regimens. For example, the therapeutic molecules of the embodiments provided herein can be used in a treatment regimen that includes neoadjuvant therapy.

In some embodiments, the therapeutic molecules, e.g. activatable anti-EGFR antibodies and/or conjugated activatable anti-EGFR antibodies, are administered during and/or after treatment in combination with one or more additional agents such as, by way of non-limiting example, a chemotherapeutic agent. In some embodiments, the therapeutic molecule and the additional agent(s) are administered simultaneously. For example, the therapeutic molecule and the additional agent(s) can be formulated in a single composition or administered as two or more separate compositions. In some embodiments, the therapeutic molecule and the additional agent(s) are administered sequentially.

The invention also provides methods of preventing, delaying the progression of, treating, alleviating a symptom of, or otherwise ameliorating an EGFR-related disorder, for example, cancer, in a subject by administering a therapeutically effective amount of an activatable anti-EGFR antibody described herein to a subject in need thereof.

The invention also provides methods of inhibiting angiogenesis in a subject by administering a therapeutically effective amount of an activatable anti-EGFR antibody described herein to a subject in need thereof.

In some embodiments, the subject is a mammal. In some embodiments, the subject is a human. In some embodiments, the subject is a non-human mammal, such as a rodent, a non-human primate, companion animal (e.g., cat, dog, horse), farm animal, work animal, or zoo animal.

The activatable anti-EGFR antibody and therapeutic formulations thereof are administered to a subject suffering from or susceptible to a disease or disorder associated with aberrant EGFR expression and/or activity. A subject suffering from or susceptible to a disease or disorder associated with aberrant EGFR expression and/or activity is identified using any of a variety of methods known in the art. For example, subjects suffering from cancer or other neoplastic condition are identified using any of a variety of clinical and/or laboratory tests such as, physical examination and blood, urine and stool analysis to evaluate health status.

The invention also provides methods of using activatable antibodies that bind EGFR (i.e., activatable anti-EGFR antibodies, also referred to herein as anti-EGFR activatable antibodies) in a variety of diagnostic and/or prophylactic indications, as well as kits for use in these methods. For example, the invention provides methods of detecting presence or absence of a cleaving agent and EGFR in a subject or a sample by (i) contacting a subject or sample with an anti-EGFR activatable antibody, and (ii) measuring a level of activated anti-EGFR activatable antibody in the subject or sample, wherein a detectable level of activated anti-EGFR activatable antibody in the subject or sample indicates that the cleaving agent and EGFR are present in the subject or sample and wherein no detectable level of activated anti-EGFR activatable antibody in the subject or sample indicates that the cleaving agent, EGFR or both the cleaving agent and EGFR are absent in the subject or sample. As used herein, "absent" can refer to the state of being not present at all in a subject or sample, as well as the state of being not present at a significant level in a subject or sample. Such an anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides kits for use in methods of detecting presence or absence of a cleaving agent and a target of interest (EGFR) in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of activated anti-EGFR activatable antibody in the subject or sample indicates that the cleaving agent and EGFR are present in the subject or sample and wherein no detectable level of activated anti-EGFR activatable antibody in the subject or sample indicates that the cleaving agent, EGFR or both the cleaving agent and EGFR are absent in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides methods of detecting presence or absence of a cleaving agent in a subject or a sample by (i) contacting a subject or sample with an anti-EGFR activatable antibody in the presence of EGFR, and (ii) measuring a level of activated anti-EGFR activatable antibody in the subject or sample, wherein a detectable level of activated anti-EGFR activatable antibody in the subject or sample indicates that the cleaving agent is present in the subject or sample and wherein no detectable level of activated anti-EGFR activatable antibody in the subject or sample indicates that the cleaving agent is absent in the subject or sample. Such an anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides kits for use in methods of detecting presence or absence of a cleaving agent in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of activated anti-EGFR activatable antibody in the subject or sample indicates that the cleaving agent is present in the subject or sample and wherein no detectable level of activated anti-EGFR activatable antibody in the subject or sample indicates that the cleaving agent is absent in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention provides methods of detecting presence or absence of a cleaving agent and EGFR in a subject or a sample by (i) contacting a subject or sample with an anti-EGFR activatable antibody, wherein the anti-EGFR activatable antibody includes a detectable label that is positioned on a portion of the anti-EGFR activatable antibody that is released following cleavage of the CM and (ii) measuring a level of activated anti-EGFR activatable antibody in the subject or sample, wherein a detectable level of activated anti-EGFR activatable antibody in the subject or sample indicates that the cleaving agent, EGFR or both the cleaving agent and EGFR are absent in the subject or sample, and wherein no detectable level of activated anti-EGFR activatable antibody in the subject or sample indicates that the cleaving agent and EGFR are present in the subject or sample. Such an anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides methods of detecting presence or absence of a cleaving agent in a subject or a sample by (i) contacting a subject or sample with an anti-EGFR activatable antibody, wherein the anti-EGFR activatable antibody includes a detectable label that is positioned on a portion of the anti-EGFR activatable antibody that is released following cleavage of the CM; and (ii) measuring a level of detectable label in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample. Such an anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides kits for use in methods of detecting presence or absence of a cleaving agent and a target of interest (EGFR) in a subject or a sample, where the kits include at least an anti-EGFR activatable antibody and/or conjugated anti-EGFR activatable antibody described herein for use in contacting a subject or sample and means for detecting the level of activated anti-EGFR activatable antibody and/or conjugated anti-EGFR activatable antibody in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

In some embodiments of these methods and/or kits, the anti-EGFR activatable antibody includes a detectable label. In some embodiments, the detectable label is positioned on the AB. In some embodiments, measuring the level of activatable anti-EGFR antibody in the subject or sample is accomplished using a secondary reagent that specifically binds to the activated antibody, wherein the reagent comprises a detectable label. In some embodiments, the secondary reagent is an antibody comprising a detectable label. In some embodiments of these methods and/or kits, the detectable label includes an imaging agent, a radioisotope, a contrasting agent, an enzyme, a fluorescent label, a chromophore, a dye, one or more metal ions, or a ligand-based label. In some embodiments of these methods and/or kits, the imaging agent comprises a radioisotope. In some embodiments of these methods, the radioisotope is indium or technetium. In some embodiments of these methods, the radioisotope is or is derived from iodine. In some embodiments of these methods, the radioisotope is $^{125}$I or $^{133}$I. In some embodiments of these methods and/or kits, the contrasting agent comprises iodine, gadolinium or iron oxide. In some embodiments of these methods and/or kits, the enzyme comprises horseradish peroxidase, alkaline phosphatase, or β-galactosidase. In some embodiments of these methods and/or kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and/or kits, the luminescent label comprises an N-methylacrydium derivative. In some embodiments of these methods and/or kits, the label comprises an Alexa Fluor® label, such as Alex Fluor® 680 or Alexa Fluor® 750.

In some embodiments of these methods and/or kits, the ligand-based label comprises biotin, avidin, streptavidin or one or more haptens.

In some embodiments of these methods and/or kits, the subject is a mammal. In some embodiments of these methods and/or kits, the subject is a human. In some embodiments, the subject is a non-human mammal, such as a rodent, a non-human primate, companion animal (e.g., cat, dog, horse), farm animal, work animal, or zoo animal.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and/or kits, the method and/or kit is used to identify or otherwise refine, e.g., stratify, a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested in these methods are identified as suitable candidates for treatment with such an anti-EGFR activatable antibody comprising such a CM. Likewise, patients that test negative for either or both of the target (e.g., EGFR) and the protease that cleaves the substrate in the CM in the activatable antibody being tested using these methods might be identified as suitable candidates for another form of therapy (i.e., not suitable for treatment with the anti-EGFR activatable antibody being tested). In some embodiments, such patients can be tested with other anti-EGFR activatable antibodies until a suitable anti-EGFR activatable antibody for treatment is identified (e.g., an anti-EGFR activatable antibody comprising a CM that is cleaved by the patient at the site of disease). Such an anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides kits for use in methods of identifying or otherwise refining a patient population, where the kits include at least (i) an anti-EGFR activatable antibody and/or conjugated anti-EGFR activatable antibody described herein for use in contacting a subject or sample, (ii) means for detecting the level of activated anti-EGFR activatable antibody and/or conjugated anti-EGFR activatable antibody in the subject or sample, wherein a detectable level of activated anti-EGFR activatable antibody in the sample indicates that the sample is positive for the presence of EGFR and a cleaving agent that cleaves the substrate in the cleavable moiety (CM) of the anti-EGFR activatable antibody and/or conjugated anti-EGFR activatable antibody and (iii) means for identifying and selecting one or more subjects that test positive for the presence of EGFR and the cleaving agent thereby identifying or refining a patient population. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12. In some embodiments, the kit also includes instructions for administering a therapeutically effective amount of an anti-EGFR activatable antibody and/or conjugated anti-EGFR activatable antibody described herein to the one or more subjects in the patient population that test positive for the presence of EGFR and the cleaving agent. In some embodiments, the kit also includes instructions for administering a therapeutically effective amount of another anti-EGFR therapeutic agent described herein to the one or more subjects in the patient population that did not test positive for the presence of both EGFR and the cleaving agent. In some embodiments, the anti-EGFR activatable antibody comprises a detectable label. In some embodiments, the detectable label is positioned on the AB. In some embodiments, measuring the level of activatable anti-EGFR antibody in the subject or sample is accomplished using a secondary reagent that specifically binds to the activated antibody, wherein the reagent comprises a detectable label. In some embodiments, the secondary reagent is an antibody comprising a detectable label. In some embodiments, the detectable label comprises an imaging agent, a radioisotope, a contrasting agent, an enzyme, a fluorescent label, a chromophore, a dye, one or more metal ions, or a ligand-based label. In some embodiments, the EGFR-related disorder is cancer. In some embodiments, the cancer is breast cancer, colorectal cancer, gastric cancer, glioblastoma, head and neck cancer, lung cancer, ovarian cancer, endometrial cancer, pancreatic cancer, prostate cancer, renal cancer, sarcoma, or skin cancer. In some embodiments, the EGFR-related disorder is psoriasis.

The invention also provides methods of using the anti-EGFR antibodies and/or conjugated activatable anti-EGFR antibodies (i.e., activatable anti-EGFR antibody conjugates, also referred to herein as conjugated activatable anti-EGFR antibodies and/or conjugated anti-EGFR activatable antibodies) in a variety of diagnostic and/or prophylactic indications. For example, the invention provides methods of detecting presence or absence of a cleaving agent and a target of interest (EGFR) in a subject or a sample by (i) contacting a subject or sample with an anti-EGFR antibody and/or conjugated activatable anti-EGFR antibody and (ii) measuring a level of anti-EGFR antibody and/or conjugated activatable anti-EGFR antibody in the subject or sample, wherein a detectable level of activated anti-EGFR antibody and/or conjugated activatable anti-EGFR antibody in the subject or sample indicates that the cleaving agent and EGFR are present in the subject or sample and wherein no detectable level of activated anti-EGFR antibody and/or conjugated activatable anti-EGFR antibody in the subject or sample indicates that the cleaving agent, EGFR or both the cleaving agent and EGFR are absent in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides methods of detecting presence or absence of a cleaving agent in a subject or a sample by (i) contacting a subject or sample with an anti-EGFR antibody and/or conjugated activatable anti-EGFR antibody in the presence of EGFR, and (ii) measuring a level of activated anti-EGFR antibody and/or conjugated activatable anti-EGFR antibody in the subject or sample, wherein a detectable level of activated anti-EGFR antibody and/or conjugated activatable anti-EGFR antibody in the subject or sample indicates that the cleaving agent is present in the subject or sample and wherein no detectable level of anti-EGFR antibody and/or conjugated activatable anti-EGFR antibody in the subject or sample indicates that the cleaving agent is absent in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

The invention also provides methods of detecting presence or absence of a cleaving agent in a subject or a sample by (i) contacting a subject or sample with an anti-EGFR antibody and/or conjugated activatable anti-EGFR antibody; and (ii) measuring a level of detectable label in the subject or sample, wherein a detectable level of the detectable label in the subject or sample indicates that the cleaving agent is absent in the subject or sample and wherein no detectable level of the detectable label in the subject or sample indicates that the cleaving agent is present in the subject or sample. Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

In some embodiments of these methods, the anti-EGFR antibody and/or conjugated activatable anti-EGFR antibody includes a detectable label selected from the group consisting of an imaging agent, a radioisotope, a contrasting agent, an enzyme, a fluorescent label, a chromophore, a dye, one or more metal ions, and a ligand-based label. In some embodiments of these methods, the imaging agent comprises a radioisotope. In some embodiments of these methods, the radioisotope is indium or technetium. In some embodiments of these methods, the contrasting agent comprises iodine, gadolinium or iron oxide. In some embodiments of these methods, the enzyme comprises horseradish peroxidase, alkaline phosphatase, or β-galactosidase. In some embodiments of these methods, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods, the luminescent label comprises an N-methylacrydium derivative. In some embodiments of these methods, the label comprises an Alexa Fluor® label, such as Alex Fluor® 680 or Alexa Fluor® 750. In some embodiments of these methods, the ligand-based label comprises biotin, avidin, streptavidin or one or more haptens. In some embodiments, the detectable label is positioned on the AB. In some embodiments, measuring the level of activatable anti-EGFR antibody in the subject or sample is accomplished using a secondary reagent that specifically binds to the activated antibody, wherein the reagent comprises a detectable label. In some embodiments, the secondary reagent is an antibody comprising a detectable label.

In some embodiments of these methods, the subject is a mammal. In some embodiments of these methods, the subject is a human. In some embodiments, the subject is a non-human mammal, such as a rodent, a non-human primate, companion animal (e.g., cat, dog, horse), farm animal, work animal, or zoo animal.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods, the method is used to identify or otherwise refine a patient population suitable for treatment with an anti-EGFR antibody and/or conjugated activatable anti-EGFR antibody of the disclosure. For example, patients that test positive for both the target (e.g., EGFR) and a protease that cleaves the substrate in the cleavable moiety (CM) of the anti-EGFR antibody and/or conjugated activatable anti-EGFR antibody being tested in these methods are identified as suitable candidates for treatment with such anti-EGFR antibody and/or such a conjugated activatable anti-EGFR antibody comprising such a CM. Likewise, patients that test negative for either or both of the target (e.g., EGFR) and the protease that cleaves the substrate in the CM in the activatable antibody being tested using these methods might be identified as suitable candidates for another form of therapy (i.e., not suitable for treatment with the anti-EGFR antibody and/or conjugated activatable anti-EGFR antibody being tested). In some embodiments, such patients can be tested with other anti-EGFR antibody and/or conjugated activatable anti-EGFR antibody until a suitable anti-EGFR antibody and/or conjugated activatable anti-EGFR antibody for treatment is identified (e.g., an anti-EGFR antibody and/or conjugated activatable anti-EGFR antibody comprising a CM that is cleaved by the patient at the site of disease). Such an anti-EGFR activatable antibody and/or conjugated anti-EGFR activatable antibody includes a heavy chain amino acid sequence selected from the group consisting of SEQ ID NO: 2, SEQ ID NO: 34, and SEQ ID NO: 36, and a masked light chain amino acid sequence selected from the group consisting of SEQ ID NO: 4, SEQ ID NO: 6, SEQ ID NO: 8, SEQ ID NO: 10, and SEQ ID NO: 12.

Pharmaceutical compositions according to the invention can include an antibody and/or conjugated antibody of the invention and a carrier. These pharmaceutical compositions can be included in kits, such as, for example, diagnostic kits.

BRIEF DESCRIPTION OF THE DRAWINGS

FIG. 1 is a schematic representation of an activatable antibody.

DETAILED DESCRIPTION OF THE INVENTION

The present invention provides activatable monoclonal antibodies (mAbs) that specifically bind human epidermal growth factor receptor (EGFR), also known as EGF receptor, human EGF receptor-1 (HER1), erbB, erbB1, and species antigen 7 (SA-7). The activatable antibodies in an uncleaved state include a masked light chain that includes or is derived from an amino acid sequence selected from the group consisting of SEQ ID NO: 4, SEQ ID NO: 6, SEQ ID NO: 8, SEQ ID NO: 10, and SEQ ID NO: 12. The activatable antibodies include a heavy chain that includes or is derived from an amino acid sequence selected from the group consisting of SEQ ID NO: 2, SEQ ID NO: 34 and SEQ ID NO: 36.

In some embodiments, the activatable antibody and/or conjugated activatable antibody in an uncleaved state includes a combination of a heavy chain amino acid sequence and a masked light chain amino acid sequence selected from the group consisting of (i) a heavy chain sequence of SEQ ID NO: 2 and a masked light chain amino acid sequence of SEQ ID NO: 4, (ii) a heavy chain sequence of SEQ ID NO: 2 and a masked light chain amino acid sequence of SEQ ID NO: 6, (iii) a heavy chain sequence of SEQ ID NO: 2 and a masked light chain amino acid sequence of SEQ ID NO: 8, (iv) a heavy chain sequence of SEQ ID NO: 2 and a masked light chain amino acid sequence of SEQ ID NO: 10, (v) a heavy chain sequence of SEQ ID NO: 2 and a masked light chain amino acid sequence of SEQ ID NO: 12, (vi) a heavy chain sequence of SEQ ID NO: 34 and a masked light chain amino acid sequence of SEQ ID NO: 4, (vii) a heavy chain sequence of SEQ ID NO: 34 and a masked light chain amino acid sequence of SEQ ID NO: 6, (viii) a heavy chain sequence of SEQ ID NO: 34 and a masked light chain amino acid sequence of SEQ ID NO: 8, (ix) a heavy chain sequence of SEQ ID NO: 34 and a masked light chain amino acid sequence of SEQ ID NO: 10, (x) a heavy chain sequence of SEQ ID NO: 34 and a masked light chain amino acid sequence of SEQ ID NO: 12, (xi) a heavy chain sequence of SEQ ID NO: 36 and a masked light chain amino acid sequence of SEQ ID NO: 4, (xii) a heavy chain sequence of SEQ ID NO: 36 and a masked light chain amino acid sequence of SEQ ID NO: 6, (xiii) a heavy chain sequence of SEQ ID NO: 36 and a masked light chain amino acid sequence of SEQ ID NO: 8, (xiv) a heavy chain sequence of SEQ ID NO: 36 and a masked light chain amino acid sequence of SEQ ID NO: 10, and (xv) a heavy chain sequence of SEQ ID NO: 36 and a masked light chain amino acid sequence of SEQ ID NO: 12.

The activatable anti-EGFR antibodies, also referred to herein as anti-EGFR activatable antibodies or EGFR activatable antibodies, are used in methods of treating, preventing, delaying the progression of, ameliorating and/or alleviating a symptom of a disease or disorder associated with aberrant EGFR expression and/or activity. For example, the activatable anti-EGFR antibodies are used in methods of treating, preventing, delaying the progression of, ameliorating and/or alleviating a symptom of a cancer or other neoplastic condition.

In an activated state, e.g., a cleaved state, the activatable antibodies bind EGFR. In an uncleaved state, e.g., non-activated state, the activatable antibodies provided herein include an antibody or an antigen binding fragment thereof (AB) that specifically binds to EGFR that includes a heavy chain amino acid sequence selected from the group consisting of SEQ ID NO: 2, SEQ ID NO: 34 and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22).

The MM is coupled to the AB via a CM sequence that includes a substrate for a protease, for example, a protease that is co-localized with EGFR at a treatment site in a subject. Numerous studies have demonstrated the correlation of aberrant protease levels, e.g., uPA, legumain, MT-SP1, matrix metalloproteases (MMPs), in solid tumors. (See e.g., Murthy R V, et al. "Legumain expression in relation to clinicopathologic and biological variables in colorectal cancer." Clin Cancer Res. 11 (2005): 2293-2299; Nielsen B S, et al. "Urokinase plasminogen activator is localized in stromal cells in ductal breast cancer." Lab Invest 81 (2001): 1485-1501; Mook O R, et al. "In situ localization of gelatinolytic activity in the extracellular matrix of metastases of colon cancer in rat liver using quenched fluorogenic DQ-gelatin." J Histochem Cytochem. 51 (2003): 821-829).

The activatable anti-EGFR antibodies provided herein include a substrate for a protease, which is useful in leveraging the protease activity in tumor cells for targeted antibody activation at the site of treatment and/or diagnosis. The substrate selection process is used to identify substrates that have a number of desirable characteristics. For example, the selected substrates are systemically stable (i.e., stable in the systemic circulation of a subject), are generally not susceptible to cleavage by circulating proteases such as plasmin, thrombin, tissue plasminogen activator (tPA) or a kallikrein (KLK) such as KLK-5 and/or KLK-7, are non-toxic, are generally not susceptible to cleavage at potential sites of toxicity such as the skin by proteases such as ADAM 9, ADAM 10, ADAM 17 and/or kallikreins, such as KLK-5 and KLK-7, and are active at an intended site of treatment and/or diagnosis. In some embodiments, the identified substrates are selected for proteases that are overexpressed at an intended site of therapy and/or diagnosis but are not typically expressed at or in normal, healthy or otherwise non-diseased or damaged tissue or in diseased or damaged tissue at a site not intended for therapy and/or diagnosis, and then the selected substrates are subsequently counter-screened against proteases expressed in normal, e.g., non-diseased, tissue or in diseased or damaged tissue at a site not intended for therapy and/or diagnosis.

The activatable anti-EGFR antibodies and/or conjugated activatable anti-EGFR antibodies described herein overcome a limitation of antibody therapeutics, particularly antibody therapeutics that are known to be toxic to at least some degree in vivo. Target-mediated toxicity constitutes a major limitation for the development of therapeutic antibodies. This is best exemplified by the skin rash that afflicts 88% of patients treated with cetuximab, an antibody that specifically binds epidermal growth factor receptor (EGFR) and has been approved for the treatment of colorectal and head and neck cancer. The activatable anti-EGFR antibodies and/or conjugated activatable anti-EGFR antibodies provided herein are designed to address the toxicity associated with the inhibition of the target in normal tissues by traditional therapeutic antibodies. These activatable anti-EGFR antibodies and/or conjugated activatable anti-EGFR antibodies remain masked until proteolytically activated at the site of disease. Starting with cetuximab as a parental therapeutic antibody, the activatable anti-EGFR antibodies and/or conjugated activatable anti-EGFR antibodies provided herein were engineered by coupling the antibody to an inhibitory mask through a linker that incorporates a protease substrate. In studies performed in vitro, the binding to EGFR and the cell-based activity of the activatable anti-EGFR antibody is diminished compared to cetuximab. In studies performed in vivo, the activatable anti-EGFR antibody remains masked in normal tissues, but is activated and accumulates in the tumor environment. The tumor activation of the activatable anti-EGFR antibody translates into an in vivo efficacy that is equivalent to the efficacy of cetuximab.

The activatable anti-EGFR antibodies and/or conjugated activatable anti-EGFR antibodies provided herein satisfy a significant clinical need. EGFR is a clinically validated target that has been shown to promote proliferation, angiogenesis and invasion/metastasis, as well as to inhibit apoptosis of tumor cells. Antibodies and small molecule tyrosine kinase inhibitors targeting EGFR have been approved for cancer treatment (Nature Rev Cancer 5 (2005) 341; Curr Opin Cell Biol 21, (2009) 177). However, current anti-EGFR therapies, also referred to as EGFR inhibitors (EGFRi), have been shown to exhibit a number of adverse events post-treatment, including for example, papulopustular rash, particularly in the face and upper trunk of human subjects; dry and itchy skin; inflammation around the nails, loss of hair on the scalp; and increased growth of eyelashes and facial hair. Cutaneous toxicities that results from treatment with EGFRi have been shown to affect 45-100% of patients. (See e.g., Segaert and Van Cutsem. Ann Oncol. 16(9) (2005):1425-33).

Exemplary activatable anti-EGFR antibodies and/or conjugated activatable anti-EGFR antibodies provided herein include, for example, the activatable antibodies referred to herein as the Des-1-3954-1204-C225v5 activatable antibody, the Des-2-3954-1204-C225v5 activatable antibody, the Des-3-3954-1204-C225v5 activatable antibody, the Des-4-3954-1204-C225v5 activatable antibody, and the Des-5-3954-1204-C225v5 activatable antibody, each of which binds epidermal growth factor receptor (EGFR) and includes the heavy chain sequence shown below as "C225v5 Activatable Antibody Heavy Chain." For example, the Des-1-3954-1204-C225v5 activatable antibody includes the Des-1-3954-1204-C225v5 light chain sequence shown below, and the C225v5 heavy chain sequence shown below; the Des-2-3954-1204-C225v5 activatable antibody includes the Des-2-3954-1204-C225v5 light chain sequence shown below, and the C225v5 heavy chain sequence shown below; the Des-3-3954-1204-C225v5 activatable antibody includes the Des-3-3954-1204-C225v5 light chain sequence shown below, and the C225v5 heavy chain sequence shown below; the Des-4-3954-1204-C225v5 activatable antibody includes the Des-4-3954-1204-C225v5 light chain sequence shown below, and the C225v5 heavy chain sequence shown below; and the Des-5-3954-1204-C225v5 activatable antibody includes the Des-5-3954-1204-C225v5 light chain sequence shown below, and the C225v5 heavy chain sequence shown below.

The following annotations are used throughout the activatable antibody sequences shown below:

```
Bold: Spacer sequence
Underline: Mask sequence
Italics and Underline: Linker 1 sequence
Bold and Underline: 1204 Substrate sequence
Bold, Italics and Underline: Linker 2 sequence
Normal text: anti-EGFR antibody derived sequence
C225v5 Activatable Antibody Heavy Chain Nucleotide Sequence:
[C225v5 (SEQ ID NO: 1)]
```
(SEQ ID NO: 1)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt ccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagcctcccagccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

C225v5 Activatable Antibody Heavy Chain Amino Acid Sequence:
[C225v5 (SEQ ID NO: 2)]

(SEQ ID NO: 2)

[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

Des-1-3954-1204-C225v5 Activatable Antibody Light Chain Nucleotide Sequence:
[Spacer (SEQ ID NO: 13)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 3)

[ggccagtctggccag][tgcatctcacctcgtggttgtccggacggcccatacgtcatgtac*g*

*gctcgagcggtggcagcggtggctctggtggatccggt*][ctgagcggccgttccgataatcat]

[*ggcagtagcggtacc*][cagatcttgctgacccagagcccggtgattctgagcgtgagcccg ggcgaacgtgtgagctttagctgccgcgcgagccagagcattggcaccaacattcattggtatc agcagcgcaccaacggcagcccgcgcctgctgattaaatatgcgagcgaaagcattagcggcat tccgagccgctttagcggcagcggcagcggcaccgatttttaccctgagcattaacagcgtggaa agcgaagatattgcggattattattgccagcagaacaacaactggccgaccacctttggcgcgg gcaccaaactggaactgaaacgtacggtggctgcaccatctgtcttcatcttcccgccatctga tgagcagttgaaatctggaactgcctctgttgtgtgcctgctgaataacttctatcccagagag gccaaagtacagtggaaggtggataacgcccctccaatcgggtaactcccaggagagtgtcacag agcaggacagcaaggacagcacctacagcctcagcagcaccctgacgctgagcaaagcagacta cgagaaacacaaagtctacgcctgcgaagtcacccatcagggcctgagctcgcccgtcacaaag agcttcaacaggggagagtgttag]

Des-1-3954-1204-C225v5 Activatable Antibody Light Chain Amino Acid Sequence:
[Spacer (SEQ ID NO: 14)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 4)

[GQSGQ][CISPRGCPDGPYVMY][*GSSGGSGGSGGSG*][LSGRSDNH][*GSSGT*][QILLTQS

PVILSVSPGERVSFSCRASQSIGTNIHWYQQRTNGSPRLLIKYASESISGIPSRFSGSGSGTDF

TLSINSVESEDIADYYCQQNNNWPTTFGAGTKLELKRTVAAPSVFIFPPSDEQLKSGTASVVCL

LNNFYPREAKVQWKVDNALQSGNSQESVTEQDSKDSTYSLSSTLTLSKADYEKHKVYACEVTHQ

GLSSPVTKSFNRGEC*]

Des-2-3954-1204-C225v5 Activatable Antibody Light Chain Nucleotide Sequence:
[Spacer (SEQ ID NO: 15)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 5)

[cagtctggccag][tgcatctcacctcgtggttgtccggacggcccatacgtcatgtac*ggct*

*cgagcggtggcagcggtggctctggtggatccggt*][ctgagcggccgttccgataatcat][*g*

*gcagtagcggtacc*][cagatcttgctgacccagagcccggtgattctgagcgtgagcccgggc gaacgtgtgagctttagctgccgcgcgagccagagcattggcaccaacattcattggtatcagc agcgcaccaacggcagcccgcgcctgctgattaaatatgcgagcgaaagcattagcggcattcc -continued gagccgctttagcggcagcggcagcggcaccgattttaccctgagcattaacagcgtggaaagc gaagatattgcggattattattgccagcagaacaacaactggccgaccacctttggcgcgggca ccaaactggaactgaaacgtacggtggctgcaccatctgtcttcatcttcccgccatctgatga gcagttgaaatctggaactgcctctgttgtgtgcctgctgaataacttctatcccagagaggcc aaagtacagtggaaggtggataacgccctccaatcgggtaactcccaggagagtgtcacagagc aggacagcaaggacagcacctacagcctcagcagcaccctgacgctgagcaaagcagactacga gaaacacaaagtctacgcctgcgaagtcacccatcagggcctgagctcgcccgtcacaaagagc ttcaacagggagagtgttag]

Des-2-3954-1204-C225v5 Activatable Antibody Light Chain Amino Acid Sequence:
[Spacer (SEQ ID NO: 16)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 6)

[QSGQ][CISPRGCPDGPYVMY][*GSSGGSGGSGGSG*][LSGRSDNH][*GSSGT*][QILLTQSP

VILSVSPGERVSFSCRASQSIGTNIHWYQQRTNGSPRLLIKYASESISGIPSRESGSGSGTDFT

LSINSVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYACEVTHQG

LSSPVTKSFNRGEC*]

Des-3-3954-1204-C225v5 Activatable Antibody Light Chain Nucleotide Sequence:
[Spacer (SEQ ID NO: 17)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 7)

[tctggccag][tgcatctcacctcgtggttgtccggacggcccatacgtcatgtac*ggctcga*

*gcggtggcagcggtggctctggtggatccggt*][ctgagcggccgttccgataatcat][*ggca*

*gtagcggtacc*][cagatcttgctgacccagagccggtgattctgagcgtgagcccgggcgaa cgtgtgagctttagctgccgcgcgagccagagcattggcaccaacattcattggtatcagcagc gcaccaacggcagcccgcgcctgctgattaaatatgcgagcgaaagcattagcggcattccgag ccgctttagcggcagcggcagcggcaccgattttaccctgagcattaacagcgtggaaagcgaa gatattgcggattattattgccagcagaacaacaactggccgaccacctttggcgcgggcacca aactggaactgaaacgtacggtggctgcaccatctgtcttcatcttcccgccatctgatgagca gttgaaatctggaactgcctctgttgtgtgcctgctgaataacttctatcccagagaggccaaa gtacagtggaaggtggataacgccctccaatcgggtaactcccaggagagtgtcacagagcagg acagcaaggacagcacctacagcctcagcagcaccctgacgctgagcaaagcagactacgagaa acacaaagtctacgcctgcgaagtcacccatcagggcctgagctcgcccgtcacaaagagcttc aacagggagagtgttag]

Des-3-3954-1204-C225v5 Activatable Antibody Light Chain Amino Acid Sequence:
[Spacer (SEQ ID NO: 18)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 8)

[SGQ][CISPRGCPDGPYVMY][*GSSGGSGGSGGSG*][LSGRSDNH][*GSSGT*][QILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC*]

Des-4-3954-1204-C225v5 Activatable Antibody Light Chain Nucleotide Sequence:
[Spacer (SEQ ID NO: 19)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 9)

[ggccag][tgcatctcacctcgtggttgtccggacggcccatacgtcatgtac*ggctcgagcg*

*gtggcagcggtggctctggtggatccggt*][ctgagcggccgttccgataatcat][*ggcagta*

*gcggtacc*][cagatcttgctgacccagagcccggtgattctgagcgtgagcccgggcgaacgt gtgagctttagctgccgcgcgagccagagcattggcaccaacattcattggtatcagcagcgca ccaacggcagcccgcgcctgctgattaaatatgcgagcgaaagcattagcggcattccgagccg ctttagcggcagcggcagcggcaccgattttaccctgagcattaacagcgtggaaagcgaagat attgcggattattattgccagcagaacaacaactggccgaccacctttggcgcgggcaccaaac tggaactgaaacgtacggtggctgcaccatctgtcttcatcttcccgccatctgatgagcagtt gaaatctggaactgcctctgttgtgtgcctgctgaataacttctatcccagagaggccaaagta cagtggaaggtggataacgcccctccaatcgggtaactcccaggagagtgtcacagagcaggaca gcaaggacagcacctacagcctcagcagcaccctgacgctgagcaaagcagactacgagaaaca caaagtctacgcctgcgaagtcacccatcagggcctgagctcgcccgtcacaaagagcttcaac aggggagagtgttag]

Des-4-3954-1204-C225v5 Activatable Antibody Light Chain Amino Acid Sequence:
[Spacer (SEQ ID NO: 20)][Mask (SEQ ID NO: 24)][ Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 10)

[GQ][CISPRGCPDGPYVMY][*GSSGGSGGSGGSG*][LSGRSDNH][*GSSGT*][QILLTQSPVI

LSVSPGERVSFSCRASQSIGTNIHWYQQRTNGSPRLLIKYASESISGIPSRFSGSGSGTDFTLS

INSVESEDIADYYCQQNNNWPTTFGAGTKLELKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC*]

Des-5-3954-1204-C225v5 Activatable Antibody Light Chain Nucleotide Sequence:
[Spacer (SEQ ID NO: 21)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 11)

[cag][tgcatctcacctcgtggttgtccggacggcccatacgtcatgtac*ggctcgagcggtg*
*gcagcggtggctctggtggatccggt*][ctgagcggccgttccgataatcat][*ggcagtagcg*
*gtacc*][cagatcttgctgacccagagcccggtgattctgagcgtgagcccgggcgaacgtgtg
agctttagctgccgcgcgagccagagcattggcaccaacattcattggtatcagcagcgcacca
acggcagcccgcgcctgctgattaaatatgcgagcgaaagcattagcggcattccgagccgctt
tagcggcagcggcagcggcaccgattttaccctgagcattaacagcgtggaaagcgaagatatt
gcggattattattgccagcagaacaacaactggccgaccacctttggcgcgggcaccaaactgg
aactgaaacgtacggtggctgcaccatctgtcttcatcttcccgccatctgatgagcagttgaa
atctggaactgcctctgttgtgtgcctgctgaataacttctatcccagagaggccaaagtacag
tggaaggtggataacgccctccaatcgggtaactcccaggagagtgtcacagagcaggacagca
aggacagcacctacagcctcagcagcaccctgacgctgagcaaagcagactacgagaaacacaa
agtctacgcctgcgaagtcacccatcagggcctgagctcgcccgtcacaaagagcttcaacagg
ggagagtgttag]

Des-5-3954-1204-C225v5 Activatable Antibody Light Chain Amino Acid Sequence:
[Spacer (SEQ ID NO: 22)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 12)

[Q][CISPRGCPDGPYVMY][*GSSGGSGGSGGSG*][LSGRSDNH][*GSSGT*][QILLTQSPVIL

SVSPGERVSFSCRASQSIGTNIHWYQQRTNGSPRLLIKYASESISGIPSRFSGSGSGTDFTLSI

NSVESEDIADYYCQQNNNWPTTFGAGTKLELKRTVAAPSVFIFPPSDEQLKSGTASVVCLLNNF

YPREAKVQWKVDNALQSGNSQESVTEQDSKDSTYSLSSTLTLSKADYEKHKVYACEVTHQGLSS

PVTKSFNRGEC*]

Exemplary activatable anti-EGFR antibodies and/or conjugated activatable anti-EGFR antibodies provided herein include, for example, the activatable antibodies referred to herein as the Des-1-3954-1204-C225v4 activatable antibody, the Des-2-3954-1204-C225v4 activatable antibody, the Des-3-3954-1204-C225v4 activatable antibody, the Des-4-3954-1204-C225v4 activatable antibody, and the Des-5-3954-1204-C225v4 activatable antibody, each of which binds epidermal growth factor receptor (EGFR) and includes the heavy chain sequence shown below as "C225v4 Activatable Antibody Heavy Chain." For example, the Des-1-3954-1204-C225v4 activatable antibody includes the Des-1-3954-1204-C225v4 light chain sequence shown below, and the C225v4 heavy chain sequence shown below; the Des-2-3954-1204-C225v4 activatable antibody includes the Des-2-3954-1204-C225v4 light chain sequence shown below, and the C225v4 heavy chain sequence shown below; the Des-3-3954-1204-C225v4 activatable antibody includes the Des-3-3954-1204-C225v4 light chain sequence shown below, and the C225v4 heavy chain sequence shown below; the Des-4-3954-1204-C225v4 activatable antibody includes the Des-4-3954-1204-C225v4 light chain sequence shown below, and the C225v4 heavy chain sequence shown below; and the Des-5-3954-1204-C225v4 activatable antibody includes the Des-5-3954-1204-C225v4 light chain sequence shown below, and the C225v4 heavy chain sequence shown below.

C225v4 Activatable Antibody Heavy Chain Nucleotide Sequence:
[C225v4 (SEQ ID NO: 33)]

(SEQ ID NO: 33)

[caggtgcagctgaaacagagcggcccgggcctggtgcagccgagccagagcctgagcattacc tgcaccgtgagcggctttagcctgaccaactatggcgtgcattgggtgcgccagagcccgggca aaggcctggaatggctgggcgtgatttggagcggcggcaacaccgattataacacccccgtttac cagccgcctgagcattaacaaagataacagcaaaagccaggtgttttttaaaatgaacagcctg caaagcaacgataccgcgatttattattgcgcgcgcgcgctgacctattatgattatgaatttg cgtattggggccagggcacccctggtgaccgtgagcgcggctagcaccaagggcccatcggtctt cccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtaca acagcacgtaccgtgtggtcagcgtcctcaccgtcctgcaccaggactggctgaatggcaagga gtacaagtgcaaggtctccaacaaagccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]

C225v4 Activatable Antibody Heavy Chain Amino Acid Sequence:
[C225v4 (SEQ ID NO: 34)]

(SEQ ID NO: 34)
[QVQLKQSGPGLVQPSQSLSITCTVSGFSLTNYGVHWVRQSPGKGLEWLGVIWSGGNTDYNTPF

TSRLSINKDNSKSQVFFKMNSLQSNDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

Des-1-3954-1204-C225v4 Activatable Antibody Light Chain Nucleotide Sequence:
[Spacer (SEQ ID NO: 13)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 3)
[ggccagtctggccag][tgcatctcacctcgtggttgtccggacggcccatacgtcatgtac]

[*ggctcgagcggtggcagcggtggctctggtggatccggt*][ctgagcggccgttccgataatc at][*ggcagtagcggtacc*][cagatcttgctgacccagagcccggtgattctgagcgtgagcc cgggcgaacgtgtgagctttagctgccgcgcgagccagagcattggcaccaacattcattggta tcagcagcgcaccaacggcagcccgcgcctgctgattaaatatgcgagcgaaagcattagcggc attccgagccgctttagcggcagcggcagcggcaccgatttta ccctgagcattaacagcgtgg aaagcgaagatattgcggattattattgccagcagaacaacaactggccgaccacctttggcgc gggcaccaaactggaactgaaacgtacggtggctgcaccatctgtcttcatcttcccgccatct gatgagcagttgaaatctggaactgcctctgttgtgtgcctgctgaataacttctatcccagag aggccaaagtacagtggaaggtggataacgcccctccaatcgggtaactcccaggagagtgtcac agagcaggacagcaaggacagcacctacagcctcagcagcaccctgacgctgagcaaagcagac tacgagaaacacaaagtctacgcctgcgaagtcacccatcagggcctgagctcgcccgtcacaa agagcttcaacaggggagagtgttag]

Des-1-3954-1204-C225v4 Activatable Antibody Light Chain Amino Acid Sequence:
[Spacer (SEQ ID NO: 14)][Mask (SEQ ID NO: 24)][Linker 1 (SEQ ID
NO: 26)][1204 Substrate (SEQ ID NO: 28)][ Linker 2 (SEQ ID
NO: 30)][C225 (SEQ ID NO: 32)]

(SEQ ID NO: 4)
[GQSGQ][CISPRGCPDGPYVMY][*GSSGGSGGSGGSG*][LSGRSDNH][*GSSGT*][QILLTQS

PVILSVSPGERVSFSCRASQSIGTNIHWYQQRTNGSPRLLIKYASESISGIPSRFSGSGSGTDF

TLSINSVESEDIADYYCQQNNNWPTTFGAGTKLELKRTVAAPSVFIFPPSDEQLKSGTASVVCL

LNNFYPREAKVQWKVDNALQSGNSQESVTEQDSKDSTYSLSSTLTLSKADYEKHKVYACEVTHQ

GLSSPVTKSFNRGEC*]

Des-2-3954-1204-C225v4 Activatable Antibody Light Chain Nucleotide Sequence:
[Spacer (SEQ ID NO: 15)][Mask (SEQ ID NO: 23)][Linker 1 (SEQ ID
NO: 25)][1204 Substrate (SEQ ID NO: 27)][ Linker 2 (SEQ ID
NO: 29)][C225 (SEQ ID NO: 31)]

(SEQ ID NO: 5)
[cagtctggccag][tgcatctcacctcgtggttgtccggacggcccatacgtcatgtac][*gg ctcgagcggtggcagcggtggctctggtggatccggt*][ctgagcggccgttccgataatcat]

-continued

[*ggcagtagcggtacc*][cagatcttgctgacccagagcccggtgattctgagcgtgagcccgg gcgaacgtgtgagctttagctgccgcgcgagccagagcattggcaccaacattcattggtatca gcagcgcaccaacggcagcccgcgcctgctgattaaatatgcgagcgaaagcattagcggcatt ccgagccgctttagcggcagcggcagcggcaccgattttaccctgagcattaacagcgtggaaa gcgaagatattgcggattattattgccagcagaacaacaactggccgaccacctttggcgcggg caccaaactggaactgaaacgtacggtggctgcaccatctgtcttcatcttcccgccatctgat gagcagttgaaatctggaactgcctctgttgtgtgcctgctgaataacttctatcccagagagg ccaaagtacagtggaaggtggataacgccctccaatcgggtaactcccaggagagtgtcacaga gcaggacagcaaggacagcacctacagcctcagcagcaccctgacgctgagcaaagcagactac gagaaacacaaagtctacgcctgcgaagtcacccatcagggcctgagctcgcccgtcacaaaga gcttcaacaggggagagtgttag]

Des-2-3954-1204-C225v4 Activatable Antibody Light Chain Amino Acid Sequence:
[Spacer (SEQ ID NO: 16)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 6)

[QSGQ][CISPRGCPDGPYVMY][*GSSGGSGGSGGSG*][LSGRSDNH][*GSSGT*][QILLTQSP

VILSVSPGERVSFSCRASQSIGTNIHWYQQRTNGSPRLLIKYASESISGIPSRFSGSGSGTDFT

LSINSVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYACEVTHQG

LSSPVTKSFNRGEC*]

Des-3-3954-1204-C225v4 Activatable Antibody Light Chain Nucleotide Sequence:
[Spacer (SEQ ID NO: 17)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 7)

[tctggccag][tgcatctcacctcgtggttgtccggacggcccatacgtcatgtac][*ggctc gagcggtggcagcggtggctctggtggatccggt*][ctgagcggccgttccgataatcat][*gg cagtagcggtacc*][cagatcttgctgacccagagcccggtgattctgagcgtgagcccgggcg aacgtgtgagctttagctgccgcgcgagccagagcattggcaccaacattcattggtatcagca gcgcaccaacggcagcccgcgcctgctgattaaatatgcgagcgaaagcattagcggcattccg agccgctttagcggcagcggcagcggcaccgattttaccctgagcattaacagcgtggaaagcg aagatattgcggattattattgccagcagaacaacaactggccgaccacctttggcgcgggcac caaactggaactgaaacgtacggtggctgcaccatctgtcttcatcttcccgccatctgatgag cagttgaaatctggaactgcctctgttgtgtgcctgctgaataacttctatcccagagaggcca aagtacagtggaaggtggataacgccctccaatcgggtaactcccaggagagtgtcacagagca ggacagcaaggacagcacctacagcctcagcagcaccctgacgctgagcaaagcagactacgag aaacacaaagtctacgcctgcgaagtcacccatcagggcctgagctcgcccgtcacaaagagct tcaacaggggagagtgttag]

Des-3-3954-1204-C225v4 Activatable Antibody Light Chain Amino Acid Sequence:
[Spacer (SEQ ID NO: 18)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 8)

[SGQ][CISPRGCPDGPYVMY][*GSSGGSGGSGGSG*][LSGRSDNH][*GSSGT*][QILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC*]

Des-4-3954-1204-C225v4 Activatable Antibody Light Chain Nucleotide Sequence:
[Spacer (SEQ ID NO: 19)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 9)

[ggccag][tgcatctcacctcgtggttgtccggacggcccatacgtcatgtac][*ggctcgag*

*cggtggcagcggtggctctggtggatccggt*][ctgagcggccgttccgataatcat][*ggcag*

*tagcggtacc*][cagatcttgctgacccagagcccggtgattctgagcgtgagcccgggcgaac gtgtgagctttagctgccgcgcgagccagagcattggcaccaacattcattggtatcagcagcg caccaacggcagcccgcgcctgctgattaaatatgcgagcgaaagcattagcggcattccgagc cgctttagcggcagcggcagcggcaccgattttaccctgagcattaacagcgtggaaagcgaag atattgcggattattattgccagcagaacaacaactggccgaccacctttggcgcgggcaccaa actggaactgaaacgtacggtggctgcaccatctgtcttcatcttcccgccatctgatgagcag ttgaaatctggaactgcctctgttgtgtgcctgctgaataacttctatcccagagaggccaaag tacagtggaaggtggataacgccctccaatcgggtaactcccaggagagtgtcacagagcagga cagcaaggacagcacctacagcctcagcagcaccctgacgctgagcaaagcagactacgagaaa cacaaagtctacgcctgcgaagtcacccatcagggcctgagctcgcccgtcacaaagagcttca acaggggagagtgttag]

Des-4-3954-1204-C225v4 Activatable Antibody Light Chain Amino Acid Sequence:
[Spacer (SEQ ID NO: 20)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 10)

[GQ][CISPRGCPDGPYVMY][*GSSGGSGGSGGSG*][LSGRSDNH][*GSSGT*][QILLTQSPVI

LSVSPGERVSFSCRASQSIGTNIHWYQQRTNGSPRLLIKYASESISGIPSRFSGSGSGTDFTLS

INSVESEDIADYYCQQNNNWPTTFGAGTKLELKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC*]

Des-5-3954-1204-C225v4 Activatable Antibody Light Chain Nucleotide Sequence:
[Spacer (SEQ ID NO: 21)][Mask (SEQ ID NO: 23)][Linker 1 (SEQ ID
NO: 25)][1204 Substrate (SEQ ID NO: 27)][Linker 2 (SEQ ID
NO: 29)][C225 (SEQ ID NO: 31)]

(SEQ ID NO: 11)

[cag][tgcatctcacctcgtggttgtccggacggcccatacgtcatgtac][*ggctcgagcgg*

*tggcagcggtggctctggtggatccggt*][ctgagcggccgttccgataatcat][*ggcagtag*

*cggtacc*][cagatcttgctgacccagagcccggtgattctgagcgtgagcccgggcgaacgtg tgagctttagctgccgcgcgagccagagcattggcaccaacattcattggtatcagcagcgcac caacggcagcccgcgcctgctgattaaatatgcgagcgaaagcattagcggcattccgagccgc tttagcggcagcggcagcggcaccgattttaccctgagcattaacagcgtggaaagcgaagata ttgcggattattattgccagcagaacaacaactggccgaccacctttggcgcgggcaccaaact ggaactgaaacgtacggtggctgcaccatctgtcttcatcttcccgccatctgatgagcagttg aaatctggaactgcctctgttgtgtgcctgctgaataacttctatcccagagaggccaaagtac agtggaaggtggataacgccctccaatcgggtaactcccaggagagtgtcacagagcaggacag Des-5-3954-1204-C225v4 Activatable Antibody Light Chain Amino Acid Sequence:
[Spacer (SEQ ID NO: 22)][Mask (SEQ ID NO: 24)][Linker 1 (SEQ ID
NO: 26)][1204 Substrate (SEQ ID NO: 28)][Linker 2 (SEQ ID
NO: 30)][C225 (SEQ ID NO: 32)]

(SEQ ID NO: 12)

[Q][CISPRGCPDGPYVMY][*GSSGGSGGSGGSG*][LSGRSDNH][*GSSGT*][QILLTQSPVIL

SVSPGERVSFSCRASQSIGTNIHWYQQRTNGSPRLLIKYASESISGIPSRFSGSGSGTDFTLSI

NSVESEDIADYYCQQNNNWPTTFGAGTKLELKRTVAAPSVFIFPPSDEQLKSGTASVVCLLNNF

YPREAKVQWKVDNALQSGNSQESVTEQDSKDSTYSLSSTLTLSKADYEKHKVYACEVTHQGLSS

PVTKSFNRGEC*]

Exemplary activatable anti-EGFR antibodies and/or conjugated activatable anti-EGFR antibodies provided herein include, for example, the activatable antibody referred to herein as the Des-1-3954-1204-C225v6 activatable antibody, the Des-2-3954-1204-C225v6 activatable antibody, the Des-3-3954-1204-C225v6 activatable antibody, the Des-4-3954-1204-C225v6 activatable antibody, and the Des-5-3954-1204-C225v6 activatable antibody, each of which binds epidermal growth factor receptor (EGFR) and includes the heavy chain sequence shown below as "C225v4 Activatable Antibody Heavy Chain." For example, the Des-1-3954-1204-C225v6 activatable antibody includes the Des-1-3954-1204-C225v6 light chain sequence shown below, and the C225v6 heavy chain sequence shown below; the Des-2-3954-1204-C225v6 activatable antibody includes the Des-2-3954-1204-C225v6 light chain sequence shown below, and the C225v6 heavy chain sequence shown below; the Des-3-3954-1204-C225v6 activatable antibody includes the Des-3-3954-1204-C225v6 light chain sequence shown below, and the C225v6 heavy chain sequence shown below; the Des-4-3954-1204-C225v6 activatable antibody includes the Des-4-3954-1204-C225v6 light chain sequence shown below, and the C225v6 heavy chain sequence shown below; and the Des-5-3954-1204-C225v6 activatable antibody includes the Des-5-3954-1204-C225v6 light chain sequence shown below, and the C225v6 heavy chain sequence shown below.

C225v6 Activatable Antibody Heavy Chain Nucleotide Sequence:
[C225v6 (SEQ ID NO: 35)]

(SEQ ID NO: 35)

[caggtgcagctgaaacagagcggcccgggcctggtgcagccgagccagagcctgagcattacc tgcaccgtgagcggctttagcctgaccaactatggcgtgcattgggtgcgccagagcccggca aaggcctggaatggctgggcgtgatttggagcggcggcaacaccgattataacaccccgtttac cagccgcctgagcattaacaaagataacagcaaaagccaggtgttttttaaaatgaacagcctg caaagccaggataccgcgatttattattgcgcgcgcgcgctgacctattatgattatgaatttg cgtattggggccagggcaccctggtgaccgtgagcgcggctagcaccaagggcccatcggtctt ccccctggcaccctcctccaagagcacctctgggggcacagcggccctgggctgcctggtcaag gactacttccccgaaccggtgacggtgtcgtggaactcaggcgccctgaccagcggcgtgcaca ccttcccggctgtcctacagtcctcaggactctactccctcagcagcgtggtgaccgtgccctc cagcagcttgggcacccagacctacatctgcaacgtgaatcacaagcccagcaacaccaaggtg gacaagaaagttgagcccaaatcttgtgacaaaactcacacatgcccaccgtgcccagcacctg aactcctggggggaccgtcagtcttcctcttccccccaaaacccaaggacaccctcatgatctc ccggacccctgaggtcacatgcgtggtggtggacgtgagccacgaagaccctgaggtcaagttc aactggtacgtggacggcgtggaggtgcataatgccaagacaaagccgcgggaggagcagtacg ccagcacgtaccgtgtggtcagcgtcctcaccgtcctgcaccaggactggctgaatggcaagga gtacaagtgcaaggtctccaacaaagccctcccagcccccatcgagaaaaccatctccaaagcc aaagggcagccccgagaaccacaggtgtacaccctgcccccatcccgggatgaactgaccaaga accaggtcagcctgacctgcctggtcaaaggcttctatcccagcgacatcgccgtggagtggga -continued

```
gagcaatgggcagccggagaacaactacaagaccacgcctcccgtgctggactccgacggctcc ttcttcctctacagcaagctcaccgtggacaagagcaggtggcagcaggggaacgtcttctcat gctccgtgatgcatgaggctctgcacaaccactacacgcagaagagcctctccctgtctccggg taaatga]
```

C225v6 Activatable Antibody Heavy Chain Amino Acid Sequence:
[C225v6 (SEQ ID NO: 36)]

(SEQ ID NO: 36)

[QVQLKQSGPGLVQPSQSLSITCTVSGFSLTNYGVHWVRQSPGKGLEWLGVIWSGGNTDYNTPF

TSRLSINKDNSKSQVFFKMNSLQSQDTAIYYCARALTYYDYEFAYWGQGTLVTVSAASTKGPSV

FPLAPSSKSTSGGTAALGCLVKDYFPEPVTVSWNSGALTSGVHTFPAVLQSSGLYSLSSVVTVP

SSSLGTQTYICNVNHKPSNTKVDKKVEPKSCDKTHTCPPCPAPELLGGPSVFLFPPKPKDTLMI

SRTPEVTCVVVDVSHEDPEVKFNWYVDGVEVHNAKTKPREEQYASTYRVVSVLTVLHQDWLNGK

EYKCKVSNKALPAPIEKTISKAKGQPREPQVYTLPPSRDELTKNQVSLTCLVKGFYPSDIAVEW

ESNGQPENNYKTTPPVLDSDGSFFLYSKLTVDKSRWQQGNVFSCSVMHEALHNHYTQKSLSLSP

GK*]

Des-1-3954-1204-C225v6 Activatable Antibody Light Chain Nucleotide Sequence:
[Spacer (SEQ ID NO: 13)][Mask (SEQ ID NO: 23)][Linker 1 (SEQ ID
NO: 25)][1204 Substrate (SEQ ID NO: 27)][Linker 2 (SEQ ID NO:
29)][C225 (SEQ ID NO: 31)]

(SEQ ID NO: 3)

[ggccagtctggccag][tgcatctcacctcgtggttgtccggacggcccatacgtcatgtac]

[*ggctcgagcggtggcagcggtggctctggtggatccggt*][ctgagcggccgttccgataatc at][*ggcagtagcggtacc*][cagatcttgctgacccagagcccggtgattctgagcgtgagcc cgggcgaacgtgtgagctttagctgccgcgcgagccagagcattggcaccaacattcattggta tcagcagcgcaccaacggcagcccgcgcctgctgattaaatatgcgagcgaaagcattagcggc attccgagccgctttagcggcagcggcagcggcaccgatttacccctgagcattaacagcgtgg aaagcgaagatattgcggattattattgccagcagaacaacaactggccgaccacctttggcgc gggcaccaaactggaactgaaacgtacggtggctgcaccatctgtcttcatcttcccgccatct gatgagcagttgaaatctggaactgcctctgttgtgtgcctgctgaataacttctatcccagag aggccaaagtacagtggaaggtggataacgcccttccaatcgggtaactcccaggagagtgtcac agagcaggacagcaaggacagcacctacagcctcagcagcaccctgacgctgagcaaagcagac tacgagaaacacaaagtctacgcctgcgaagtcacccatcagggcctgagctcgcccgtcacaa agagcttcaacaggggagagtgttag]

Des-1-3954-1204-C225v6 Activatable Antibody Light Chain Amino Acid Sequence:
[Spacer (SEQ ID NO: 14)][Mask (SEQ ID NO: 24)][Linker 1 (SEQ ID
NO: 26)][1204 Substrate (SEQ ID NO: 28)][Linker 2 (SEQ ID NO:
30)][C225 (SEQ ID NO: 32)]

(SEQ ID NO: 4)

[GQSGQ][CISPRGCPDGPYVMY][*GSSGGSGGSGGSG*][LSGRSDNH][*GSSGT*][QILLTQS

PVILSVSPGERVSFSCRASQSIGTNIHWYQQRTNGSPRLLIKYASESISGIPSRFSGSGSGTDF

TLSINSVESEDIADYYCQQNNNWPTTFGAGTKLELKRTVAAPSVFIFPPSDEQLKSGTASVVCL

LNNFYPREAKVQWKVDNALQSGNSQESVTEQDSKDSTYSLSSTLTLSKADYEKHKVYACEVTHQ

GLSSPVTKSFNRGEC*]

Des-2-3954-1204-C225v6 Activatable Antibody Light Chain Nucleotide Sequence:
[Spacer (SEQ ID NO: 15)][Mask (SEQ ID NO: 23)][Linker 1 (SEQ ID
NO: 25)][1204 Substrate (SEQ ID NO: 27)][Linker 2 (SEQ ID NO:
29)][C225 (SEQ ID NO: 31)]

(SEQ ID NO: 5)

[cagtctggccag][tgcatctcacctcgtggttgtccggacggcccatacgtcatgtac][*gg ctcgagcggtggcagcggtggctctggtggatccggt*][ctgagcggccgttccgataatcat]

[ggcagtagcggtacc][cagatcttgctgacccagagcccggtgattctgagcgtgagcccgg gcgaacgtgtgagctttagctgccgcgcgagccagagcattggcaccaacattcattggtatca gcagcgcaccaacggcagcccgcgcctgctgattaaatatgcgagcgaaagcattagcggcatt ccgagccgctttagcggcagcggcagcggcaccgattttaccctgagcattaacagcgtggaaa gcgaagatattgcggattattattgccagcagaacaacaactggccgaccacctttggcgcggg caccaaactggaactgaaacgtacggtggctgcaccatctgtcttcatcttcccgccatctgat gagcagttgaaatctggaactgcctctgttgtgtgcctgctgaataacttctatcccagagagg ccaaagtacagtggaaggtggataacgcccrccaatcgggtaactcccaggagagtgtcacaga gcaggacagcaaggacagcacctacagcctcagcagcaccctgacgctgagcaaagcagactac gagaaacacaaagtctacgcctgcgaagtcacccatcagggcctgagctcgcccgtcacaaaga gcttcaacaggggagagtgttag]

Des-2-3954-1204-C225v6 Activatable Antibody Light Chain Amino Acid Sequence:
[Spacer (SEQ ID NO: 16)][Mask (SEQ ID NO: 24)][Linker 1 (SEQ ID
NO: 26)][1204 Substrate (SEQ ID NO: 28)][Linker 2 (SEQ ID NO:
30)][C225 (SEQ ID NO: 32)]

(SEQ ID NO: 6)
[QSGQ][CISPRGCPDGPYVMY][*GSSGGSGGSGGSG*][LSGRSDNH][*GSSGT*][QILLTQSP

VILSVSPGERVSFSCRASQSIGTNIHWYQQRTNGSPRLLIKYASESISGIPSRFSGSGSGTDFT

LSINSVESEDIADYYCQQNNNWPTTFGAGTKLELKRTVAAPSVFIFPPSDEQLKSGTASVVCLL

NNFYPREAKVQWKVDNALQSGNSQESVTEQDSKDSTYSLSSTLTLSKADYEKHKVYACEVTHQG

LSSPVTKSFNRGEC*]

Des-3-3954-1204-C225v6 Activatable Antibody Light Chain Nucleotide Sequence:
[Spacer (SEQ ID NO: 17)][Mask (SEQ ID NO: 23)][Linker 1 (SEQ ID
NO: 25)][1204 Substrate (SEQ ID NO: 27)][Linker 2 (SEQ ID NO:
29)][C225 (SEQ ID NO: 31)]

(SEQ ID NO: 7)
[tctggccag][tgcatctcacctcgtggttgtccggacggcccatacgtcatgtac][*ggctc gagcggtggcagcggtggctctggtggatccggt*][ctgagcggccgttccgataatcat][*gg cagtagcggtacc*][cagatcttgctgacccagagcccggtgattctgagcgtgagcccgggcg aacgtgtgagctttagctgccgcgcgagccagagcattggcaccaacattcattggtatcagca gcgcaccaacggcagcccgcgcctgctgattaaatatgcgagcgaaagcattagcggcattccg agccgctttagcggcagcggcagcggcaccgattttaccctgagcattaacagcgtggaaagcg aagatattgcggattattattgccagcagaacaacaactggccgaccacctttggcgcgggcac caaactggaactgaaacgtacggtggctgcaccatctgtcttcatcttcccgccatctgatgag cagttgaaatctggaactgcctctgttgtgtgcctgctgaataacttctatcccagagaggcca aagtacagtggaaggtggataacgcccrccaatcgggtaactcccaggagagtgtcacagagca ggacagcaaggacagcacctacagcctcagcagcaccctgacgctgagcaaagcagactacgag aaacacaaagtctacgcctgcgaagtcacccatcagggcctgagctcgcccgtcacaaagagct tcaacaggggagagtgttag]

Des-3-3954-1204-C225v6 Activatable Antibody Light Chain Amino Acid Sequence:
[Spacer (SEQ ID NO: 18)][Mask (SEQ ID NO: 24)][Linker 1 (SEQ ID
NO: 26)][1204 Substrate (SEQ ID NO: 28)][Linker 2 (SEQ ID NO:
30)][C225 (SEQ ID NO: 32)]

(SEQ ID NO: 8)
[SGQ][CISPRGCPDGPYVMY][*GSSGGSGGSGGSG*][LSGRSDNH][*GSSGT*][QILLTQSPV

ILSVSPGERVSFSCRASQSIGTNIHWYQQRTNGSPRLLIKYASESISGIPSRFSGSGSGTDFTL

SINSVESEDIADYYCQQNNNWPTTFGAGTKLELKRTVAAPSVFIFPPSDEQLKSGTASVVCLLN

NFYPREAKVQWKVDNALQSGNSQESVTEQDSKDSTYSLSSTLTLSKADYEKHKVYACEVTHQGL

SSPVTKSFNRGEC*]

Des-4-3954-1204-C225v6 Activatable Antibody Light Chain Nucleotide Sequence:
[Spacer (SEQ ID NO: 19)][Mask (SEQ ID NO: 23)][Linker 1 (SEQ ID
NO: 25)][1204 Substrate (SEQ ID NO: 27)][Linker 2 (SEQ ID NO:
29)][C225 (SEQ ID NO: 31)]

(SEQ ID NO: 9)

[ggccag][tgcatctcacctcgtggttgtccggacggcccatacgtcatgtac][*ggctcgag*

*cggtggcagcggtggctctggtggatccggt*][ctgagcggccgttccgataatcat][*ggcag*

*tagcggtacc*][cagatcttgctgacccagagcccggtgattctgagcgtgagcccgggcgaac gtgtgagctttagctgccgcgcgagccagagcattggcaccaacattcattggtatcagcagcg caccaacggcagcccgcgcctgctgattaaatatgcgagcgaaagcattagcggcattccgagc cgctttagcggcagcggcagcggcaccgattttaccctgagcattaacagcgtggaaagcgaag atattgcggattattattgccagcagaacaacaactggccgaccacctttggcgcgggcaccaa actggaactgaaacgtacggtggctgcaccatctgtcttcatcttcccgccatctgatgagcag ttgaaatctggaactgcctctgttgtgtgcctgctgaataacttctatcccagagaggccaaag tacagtggaaggtggataacgccctccaatcgggtaactcccaggagagtgtcacagagcagga cagcaaggacagcacctacagcctcagcagcaccctgacgctgagcaaagcagactacgagaaa cacaaagtctacgcctgcgaagtcacccatcagggcctgagctcgcccgtcacaaagagcttca acaggggagagtgttag]

Des-4-3954-1204-C225v6 Activatable Antibody Light Chain Amino Acid Sequence:
[Spacer (SEQ ID NO: 20)][Mask (SEQ ID NO: 24)][Linker 1 (SEQ ID
NO: 26)][1204 Substrate (SEQ ID NO: 28)][Linker 2 (SEQ ID NO:
30)][C225 (SEQ ID NO: 32)]

(SEQ ID NO: 10)

[GQ][CISPRGCPDGPYVMY][*GSSGGSGGSGGSG*][LSGRSDNH][*GSSGT*][QILLTQSPVI

LSVSPGERVSFSCRASQSIGTNIHWYQQRTNGSPRLLIKYASESISGIPSRFSGSGSGTDFTLS

INSVESEDIADYYCQQNNNWPTTFGAGTKLELKRTVAAPSVFIFPPSDEQLKSGTASVVCLLNN

FYPREAKVQWKVDNALQSGNSQESVTEQDSKDSTYSLSSTLTLSKADYEKHKVYACEVTHQGLS

SPVTKSFNRGEC*]

Des-5-3954-1204-C225v6 Activatable Antibody Light Chain Nucleotide Sequence:
[Spacer (SEQ ID NO: 21)][Mask (SEQ ID NO: 23)][Linker 1 (SEQ ID
NO: 25)][1204 Substrate (SEQ ID NO: 27)][Linker 2 (SEQ ID NO:
29)][C225 (SEQ ID NO: 31)]

(SEQ ID NO: 11)

[cag][tgcatctcacctcgtggttgtccggacggcccatacgtcatgtac][*ggctcgagcgg*

*tggcagcggtggctctggtggatccggt*][ctgagcggccgttccgataatcat][*ggcagtag*

*cggtacc*][cagatcttgctgacccagagcccggtgattctgagcgtgagcccgggcgaacgtg tgagctttagctgccgcgcgagccagagcattggcaccaacattcattggtatcagcagcgcac caacggcagcccgcgcctgctgattaaatatgcgagcgaaagcattagcggcattccgagccgc tttagcggcagcggcagcggcaccgattttaccctgagcattaacagcgtggaaagcgaagata ttgcggattattattgccagcagaacaacaactggccgaccacctttggcgcgggcaccaaact ggaactgaaacgtacggtggctgcaccatctgtcttcatcttcccgccatctgatgagcagttg aaatctggaactgcctctgttgtgtgcctgctgaataacttctatcccagagaggccaaagtac agtggaaggtggataacgccctccaatcgggtaactcccaggagagtgtcacagagcaggacag caaggacagcacctacagcctcagcagcaccctgacgctgagcaaagcagactacgagaaacac aaagtctacgcctgcgaagtcacccatcagggcctgagctcgcccgtcacaaagagcttcaaca ggggagagtgttag]

```
Des-5-3954-1204-C225v6 Activatable Antibody Light Chain Amino Acid Sequence:
[Spacer (SEQ ID NO: 22)][Mask (SEQ ID NO: 24)][Linker 1 (SEQ ID
NO: 26)][1204 Substrate (SEQ ID NO: 28)][Linker 2 (SEQ ID NO:
30)][C225 (SEQ ID NO: 32)]
                                                                    (SEQ ID NO: 12)
[Q][CISPRGCPDGPYVMY][GSSGGSGGSGGSG][LSGRSDNH][GSSGT][QILLTQSPVIL

SVSPGERVSFSCRASQSIGTNIHWYQQRTNGSPRLLIKYASESISGIPSRFSGSGSGTDFTLSI

NSVESEDIADYYCQQNNNWPTTFGAGTKLELKRTVAAPSVFIFPPSDEQLKSGTASVVCLLNNF

YPREAKVQWKVDNALQSGNSQESVTEQDSKDSTYSLSSTLTLSKADYEKHKVYACEVTHQGLSS

PVTKSFNRGEC*]
```

In some embodiments, the anti-EGFR activatable antibody and/or conjugated anti-EGFR activatable antibody includes a heavy chain selected from the group consisting of SEQ ID NO: 2, SEQ ID NO: 34 and SEQ ID NO: 36, and a light chain amino acid sequence that includes SEQ ID NO: 32 coupled to a spacer that has an amino acid sequence selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22) and is linked to a masking moiety (MM) that includes a sequence selected from the group consisting of CISPRG (SEQ ID NO: 76); CISPRGCG (SEQ ID NO: 77); CISPRGCPDGPYVMY (SEQ ID NO: 24); CISPRGCPDGPYVM (SEQ ID NO: 78); CISPRGCEPGTYVPT (SEQ ID NO: 79); CISPRGCPGQIWHPP (SEQ ID NO: 80); GSHCLIPINMGAPSC (SEQ ID NO: 81); CISPRGCGGSSASQSGQGSHCLIPINMGAPSC (SEQ ID NO: 82); CNHHYFYTCGCISPRGCPG (SEQ ID NO: 83); ADHVFWGSYGCISPRGCPG (SEQ ID NO: 84); CHHVYWGHCGCISPRGCPG (SEQ ID NO: 85); CPHFTTTSCGCISPRGCPG (SEQ ID NO: 86); CNHHYHYYCGCISPRGCPG (SEQ ID NO: 87); CPHVSFGSCGCISPRGCPG (SEQ ID NO: 88); CPYYTLSYCGCISPRGCPG (SEQ ID NO: 89); CNHVYFGTCGCISPRGCPG (SEQ ID NO: 90); CNHFTLTTCGCISPRGCPG (SEQ ID NO: 91); CHHFTLTTCGCISPRGCPG (SEQ ID NO: 92); YNPCATPMCCISPRGCPG (SEQ ID NO: 93); CNHHYFYTCGCISPRGCG (SEQ ID NO: 94); CNHHYHYYCGCISPRGCG (SEQ ID NO: 95); CNHVYFGTCGCISPRGCG (SEQ ID NO: 96); CHHVYWGHCGCISPRGCG (SEQ ID NO: 97); CPHFTTTSCGCISPRGCG (SEQ ID NO: 98); CNHFTLTTCGCISPRGCG (SEQ ID NO: 99); CHHFTLTTCGCISPRGCG (SEQ ID NO: 100); CPYYTLSYCGCISPRGCG (SEQ ID NO: 101); CPHVSFGSCGCISPRGCG (SEQ ID NO: 102); ADHVFWGSYGCISPRGCG (SEQ ID NO: 103); YNPCATPMCCISPRGCG (SEQ ID NO: 104); CHHVYWGHCGCISPRGCG (SEQ ID NO: 105); C(N/P)H(H/V/F)(Y/T)(F/W/T/L)(Y/G/T/S)(T/S/Y/H)CGCISPRGCG (SEQ ID NO: 106); CISPRGCGQPIPSVK (SEQ ID NO: 107); CISPRGCTQPYHVSR (SEQ ID NO: 108); and/or CISPRGCNAVSGLGS (SEQ ID NO: 109).

In some embodiments, the CM is a substrate for an MMP and includes the sequence ISSGLLSS (SEQ ID NO: 110); QNQALRMA (SEQ ID NO: 111); AQNLLGMV (SEQ ID NO: 112); STFPFGMF (SEQ ID NO: 113); PVGYTSSL (SEQ ID NO: 114); DWLYWPGI (SEQ ID NO: 115); MIAPVAYR (SEQ ID NO: 116); RPSPMWAY (SEQ ID NO: 117); WATPRPMR (SEQ ID NO: 118); FRLLDWQW (SEQ ID NO: 119); LKAAPRWA (SEQ ID NO: 120); GPSHLVLT (SEQ ID NO: 121); LPGGLSPW (SEQ ID NO: 122); MGLFSEAG (SEQ ID NO: 123); SPLPLRVP (SEQ ID NO: 124); RVIHILRSLG (SEQ ID NO: 125); LAAPLGLL (SEQ ID NO: 126); AVGLLAPP (SEQ ID NO: 127); LLAPSHRA (SEQ ID NO: 128); PAGLWLDP (SEQ ID NO: 129); and/or ISSGLSS (SEQ ID NO: 130).

In some embodiments, the CM includes the sequence TGRGPSWV (SEQ ID NO: 131); SARGPSRW (SEQ ID NO: 132); TARGPSFK (SEQ ID NO: 133); LSGRSDNH (SEQ ID NO: 134); GGWHTGRN (SEQ ID NO: 135); HTGRSGAL (SEQ ID NO: 136); PLTGRSGG (SEQ ID NO: 137); AARGPAIH (SEQ ID NO: 138); RGPAFNPM (SEQ ID NO: 139); SSRGPAYL (SEQ ID NO: 140); RGPATPIM (SEQ ID NO: 141); RGPA (SEQ ID NO: 142); GGQPSGMWGW (SEQ ID NO: 143); FPRPLGITGL (SEQ ID NO: 144); VHMPLGFLGP (SEQ ID NO: 145); SPLTGRSG (SEQ ID NO: 146); SAGFSLPA (SEQ ID NO: 147); LAPLGLQRR (SEQ ID NO: 148); SGGPLGVR (SEQ ID NO: 149); and/or PLGL (SEQ ID NO: 150).

In some embodiments, the activatable anti-EGFR antibodies described herein also include an agent conjugated to the activatable antibody. In some embodiments, the conjugated agent is a therapeutic agent, such as an antineoplastic agent. In such embodiments, the agent is conjugated to a carbohydrate moiety of the activatable antibody, and in some embodiments, where the carbohydrate moiety is located outside the antigen-binding region of the antibody or antigen-binding fragment in the activatable antibody. In some embodiments, the agent is conjugated to a sulfhydryl group of the antibody or antigen-binding fragment in the activatable antibody. In some embodiments, the agent is conjugated to an amino group of the antibody or antigen-binding fragment of the activatable antibody. In some embodiments the agent is conjugated to a carboxylic acid group of the antibody or antigen-binding fragment of the activatable antibody.

In some embodiments, the agent is a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, any of the cytotoxic agents listed in Table 1. In some embodiments, the cytotoxic agent is a dolastatin or a derivative thereof (e.g. auristatin E, AFP, MMAF, MMAE, DMAF, DMAE). For example, the cytotoxic agent is monomethyl auristatin E (MMAE).

In some embodiments, the conjugated activatable antibody can be modified for site-specific conjugation through modified amino acid sequences inserted or otherwise included in the activatable antibody sequence. These modified amino acid sequences are designed to allow for controlled placement and/or dosage of the conjugated agent within a conjugated activatable anti-EGFR antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Methods of preparing a conjugate of an activatable anti-EGFR antibody having one or more interchain disulfide bonds in the AB and one or more intrachain disulfide bonds in the MM, and a drug reactive with free thiols are provided. These methods generally include partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where an activatable anti-EGFR antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to an activatable anti-EGFR antibody resulting in selectivity in the placement of the agent is provided. The method generally includes partially reducing the activatable anti-EGFR antibody with a reducing agent such that any conjugation sites in the masking moiety or other non-AB portion of the activatable antibody are not reduced, and conjugating the agent to interchain thiols in the AB. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to activatable anti-EGFR antibody will vary depending on the activatable antibody. In some embodiments, the ratio of reducing agent to activatable anti-EGFR antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

In some embodiments, a method of reducing interchain disulfide bonds in the AB of an activatable anti-EGFR antibody and conjugating an agent, e.g., a thiol-containing agent such as a drug, to the resulting interchain thiols to selectively locate agent(s) on the AB is provided. The method generally includes partially reducing the AB with a reducing agent to form at least two interchain thiols without forming all possible interchain thiols in the activatable antibody; and conjugating the agent to the interchain thiols of the partially reduced AB. For example, the AB of the activatable antibody is partially reduced for about 1 hour at about 37° C. at a desired ratio of reducing agent:activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

Also provided are partially reduced activatable anti-EGFR antibodies in which at least one interchain disulfide bond in the activatable antibody has been reduced with a reducing agent without disturbing any intrachain disulfide bonds in the activatable antibody, wherein the activatable antibody includes an antibody or an antigen binding fragment thereof (AB) that specifically binds to EGFR, a masking moiety (MM) that inhibits the binding of the AB of the activatable antibody in an uncleaved state to the EGFR target, and a cleavable moiety (CM) coupled to the AB, wherein the CM is a polypeptide that functions as a substrate for a protease. In some embodiments the MM is coupled to the AB via the CM. In some embodiments, one or more intrachain disulfide bond(s) of the activatable antibody is not disturbed by the reducing agent. In some embodiments, one or more intrachain disulfide bond(s) of the MM within the activatable antibody is not disturbed by the reducing agent. In some embodiments, the activatable antibody in the uncleaved state has the structural arrangement from N-terminus to C-terminus as follows: MM-CM-AB or AB-CM-MM. In some embodiments, reducing agent is TCEP.

In an uncleaved state, e.g., non-activated state, the activatable antibodies provided herein include an AB that specifically binds to EGFR that includes a heavy chain amino acid sequence selected from the group consisting of SEQ ID NO: 2, SEQ ID NO: 34, and SEQ ID NO: 36, and a light chain amino acid sequence that includes SEQ ID NO: 32, wherein the activatable antibody in the uncleaved state has the structural arrangement from N-terminus to C-terminus as follows: Spacer Sequence-Masking Moiety (MM)-Linking Peptide 1 (LP1)-Cleavable Moiety (CM)-Linking Peptide 2 (LP2)-AB or AB-LP2-CM-LP1-MM-Spacer Sequence, wherein the MM includes the amino acid sequence CISPRGCPDGPYVMY (SEQ ID NO: 24), the CM includes the amino acid sequence LSGRSDNH (SEQ ID NO: 28), and the Spacer Sequence is selected from the group consisting of GQSGQ (SEQ ID NO: 14), QSGQ (SEQ ID NO: 16), SGQ (SEQ ID NO: 18), GQ (SEQ ID NO: 20), and Q (SEQ ID NO: 22). In some embodiments, the two linking peptides need not be identical to each other.

In some embodiments, the activatable antibodies provided herein, in an uncleaved state, include a masked light chain that includes or is derived from an amino acid sequence selected from the group consisting of SEQ ID NO: 4, SEQ ID NO: 6, SEQ ID NO: 8, SEQ ID NO: 10, and SEQ ID NO: 12. In some embodiments, the activatable antibody and/or conjugated activatable antibody in an uncleaved state includes a heavy chain amino acid sequence that is at least 90%, 91%, 92%, 93%, 94%, 95%, 96%, 97%, 98% or 99% identical to an amino acid selected from the group consisting of SEQ ID NO: 2, SEQ ID NO: 34, and SEQ ID NO: 36, and a masked light chain amino acid sequence that is at least 90%, 91%, 92%, 93%, 94%, 95%, 96%, 97%, 98% or 99% identical to an amino acid sequence selected from the group consisting of SEQ ID NO: 4, SEQ ID NO: 6, SEQ ID NO: 8, SEQ ID NO: 10, and SEQ ID NO: 12.

In some embodiments, the agent is a detectable moiety such as, for example, a label or other marker. For example, the agent is or includes a radiolabeled amino acid, one or more biotinyl moieties that can be detected by marked avidin (e.g., streptavidin containing a fluorescent marker or enzymatic activity that can be detected by optical or calorimetric methods), one or more radioisotopes or radionuclides, one or more fluorescent labels, one or more enzymatic labels, and/or one or more chemiluminescent agents. In some embodiments, detectable moieties are attached by spacer molecules.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{111}$In, $^{90}$Y, and $^{186}$Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible moieties can be coupled to the resultant antibodies of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Table 1 lists some of the exemplary pharmaceutical agents that may be employed in the herein described invention but in no way is meant to be an exhaustive list.

TABLE 1

Exemplary Pharmaceutical Agents for Conjugation

CYTOTOXIC AGENTS

Auristatins
Auristatin E
Monomethyl auristatin D (MMAD)
Monomethyl auristatin E (MMAE)
Desmethyl auristatin E (DMAE)
Auristatin F
Monomethyl auristatin F (MMAF)
Desmethyl auristatin F (DMAF)
Auristatin derivatives, e.g., amides thereof
Auristatin tyramine
Auristatin quinoline
Dolastatins
Dolastatin derivatives
Dolastatin 16 DmJ
Dolastatin 16 Dpv
Maytansinoids, e.g. DM-1; DM-4
Maytansinoid derivatives
Duocarmycin
Duocarmycin derivatives
Alpha-amanitin
Anthracyclines
Doxorubicin
Daunorubicin
Bryostatins
Camptothecin
Camptothecin derivatives
7-substituted Camptothecin
10, 11-Difluoromethylenedioxycamptothecin
Combretastatins
Debromoaplysiatoxin
Kahalalide-F
Discodermolide
Ecteinascidins

ANTIVIRALS

Acyclovir
Vira A
Symmetrel

ANTIFUNGALS

Nystatin

ADDITIONAL ANTI-NEOPLASTICS

Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine ANTI-BACTERIALS
Aminoglycosides Streptomycin
Neomycin
Kanamycin
Amikacin
Gentamicin
Tobramycin
Streptomycin B
Spectinomycin
Ampicillin
Sulfanilamide TABLE 1-continued Exemplary Pharmaceutical Agents for Conjugation Polymyxin
Chloramphenicol
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Cemadotin analogue (CemCH2-SH)
Pseudomonas toxin A (PE38) variant
Pseudomonas toxin A (ZZ-PE38) variant
ZJ-101
OSW-1
4-Nitrobenzyloxycarbonyl Derivatives of
O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes
Calicheamicins
Podophyllotoxins
Taxanes
Vinca alkaloids

CONJUGATABLE DETECTION REAGENTS

Fluorescein and derivatives thereof
Fluorescein isothiocyanate (FITC)

RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)

HEAVY METALS

Barium
Gold
Platinum

ANTI-MYCOPLASMALS

Tylosine
Spectinomycin

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030, 719, describing use of halogenated acetyl hydrazide derivative coupled to an antibody by way of an oligopeptide linker. For example, suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide] hexanoate (Pierce Chem. Co. Cat. #2165-G.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl) carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

The present invention utilizes several methods for attaching agents to ABs: (a) attachment to the carbohydrate moieties of the AB, or (b) attachment to sulfhydryl groups of the AB, or (c) attachment to amino groups of the AB, or (d) attachment to carboxylate groups of the AB. According to the invention, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present invention, suitable linkers for attachment to reduced ABs include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present invention, suitable linkers for attachment to neither oxidized nor reduced Abs include those having certain functional groups capable of reaction with the primary amino groups present in unmodified lysine residues in the Ab. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present invention, suitable linkers for attachment to neither oxidized nor reduced AB's include those having certain functional groups capable of reaction with the carboxylic acid groups present in aspartate or glutamate residues in the AB, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers: In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers: Peptide linkers that are susceptible to cleavage by enzymes of the complement system, such as but not limited to urokinase, tissue plasminogen activator, trypsin, plasmin, or another enzyme having proteolytic activity may be used in one embodiment of the present invention. According to one method of the present invention, an agent is attached via a linker susceptible to cleavage by complement. The antibody is selected from a class that can activate complement. The antibody-agent conjugate, thus, activates the complement cascade and releases the agent at the target site. According to another method of the present invention, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 1.

Non-limiting examples of cleavable linker sequences are provided in Table 2.

TABLE 2

Exemplary Linker Sequences for Conjugation

| Types of Cleavable Sequences | Amino Acid Sequence |
|---|---|
| Plasmin cleavable sequences | |
| Pro-urokinase | PRFKIIGG (SEQ ID NO: 37) |
| | PRFRIIGG (SEQ ID NO: 38) |
| TGFβ | SSRHRRALD (SEQ ID NO: 39) |
| Plasminogen | RKSSIIRMRDVVL (SEQ ID NO: 40) |
| Staphylokinase | SSSFDKGKYKKGDDA (SEQ ID NO: 41) |
| | SSSFDKGKYKRGDDA (SEQ ID NO: 42) |
| Factor Xa cleavable sequences | IEGR (SEQ ID NO: 43) |
| | IDGR (SEQ ID NO: 44) |
| | GGSIDGR (SEQ ID NO: 45) |
| MMP cleavable sequences | |
| Gelatinase A | PLGLWA (SEQ ID NO: 46) |

TABLE 2-continued

Exemplary Linker Sequences for Conjugation

| Types of Cleavable Sequences | Amino Acid Sequence |
|---|---|
| Collagenase cleavable sequences | |
| Calf skin collagen (α1(I) chain) | GPQGIAGQ (SEQ ID NO: 47) |
| Calf skin collagen (α2(I) chain) | GPQGLLGA (SEQ ID NO: 48) |
| Bovine cartilage collagen (α1(II) chain) | GIAGQ (SEQ ID NO: 49) |
| Human liver collagen (α1(III) chain) | GPLGIAGI (SEQ ID NO: 50) |
| Human α$_2$M | GPEGLRVG (SEQ ID NO: 51) |
| Human PZP | YGAGLGVV (SEQ ID NO: 52)<br>AGLGVVER (SEQ ID NO: 53)<br>AGLGISST (SEQ ID NO: 54) |
| Rat α$_1$M | EPQALAMS (SEQ ID NO: 55)<br>QALAMSAI (SEQ ID NO: 56) |
| Rat α$_2$M | AAYHLVSQ (SEQ ID NO: 57)<br>MDAFLESS (SEQ ID NO: 58) |
| Rat α$_1$I$_3$(2J) | ESLPVVAV (SEQ ID NO: 59) |
| Rat α$_1$I$_3$(27J) | SAPAVESE (SEQ ID NO: 60) |
| Human fibroblast collagenase (autolytic cleavages) | DVAQFVLT (SEQ ID NO: 61)<br>VAQFVLTE (SEQ ID NO: 62)<br>AQFVLTEG (SEQ ID NO: 63)<br>PVQPIGPQ (SEQ ID NO: 64) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements: In still another embodiment, it may be necessary to construct the linker in such a way as to optimize the spacing between the agent and the AB of the activatable antibody. This may be accomplished by use of a linker of the general structure:

wherein
W is either —NH—CH$_2$— or —CH$_2$—;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers: According to one method of the present invention, when release of an agent is desired, an AB that is an antibody of a class that can activate complement is used. The resulting conjugate retains both the ability to bind antigen and activate the complement cascade. Thus, according to this embodiment of the present invention, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodiimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 1.

Linkers for Release without Complement Activation: In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers: In other embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 3.

Non-Cleavable Linkers or Direct Attachment: In still other embodiments of the invention, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A-general formula for such an organic linker could be $$W-(CH_2)n-Q$$

wherein
W is either —NH—CH$_2$— or —CH$_2$—;
Q is an amino acid, peptide; and
n is an integer from 0 to 20.

Non-Cleavable Conjugates: Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

Definitions

Unless otherwise defined, scientific and technical terms used in connection with the present invention shall have the meanings that are commonly understood by those of ordinary skill in the art. Further, unless otherwise required by

TABLE 3

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å | context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$ M). Antibodies include, but are not limited to, polyclonal antibodies, monoclonal antibodies, chimeric antibodies, domain antibodies, single chain antibodies, Fab, and F(ab')2 fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is ≤1 µM; in some embodiments ≤100 nM, and in some embodiments ≤10 nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to EGFR, when the equilibrium binding constant ($K_d$) is 1 µM, in some embodiments ≤100 nM, in some embodiments ≤10 nM, and in some embodiments ≤100 pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the invention include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the invention comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and in some embodiments, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the invention are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present invention. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, in some embodiments, at least 90 percent sequence identity, in some embodiments, at least 95 percent sequence identity, and in some embodiments, at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present invention, providing that the variations in the amino acid sequence maintain at least 75%, in some embodiments, at least 80%, 90%, 95%, and in some embodiments, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the invention.

In some embodiments, amino acid substitutions are those that: (1) reduce susceptibility to proteolysis, (2) reduce susceptibility to oxidation, (3) alter binding affinity for forming protein complexes, (4) alter binding affinities, and (5) confer or modify other physicochemical or functional properties of such analogs. Analogs can include various muteins of a sequence other than the naturally-occurring peptide sequence. For example, single or multiple amino acid substitutions (in some embodiments, conservative amino acid substitutions) may be made in the naturally-occurring sequence (in some embodiments, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, in some embodiments, at least 14 amino acids long, in some embodiments, at least 20 amino acids long, usually at least 50 amino acids long, and in some embodiments, at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, in some embodiments, at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$ $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and in some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Antibodies

Activatable antibodies of the invention specifically bind human epidermal growth factor receptor (EGFR). Also included in the invention are activatable antibodies that bind to the same epitope as the activatable anti-EGFR antibodies described herein.

Those skilled in the art will recognize that it is possible to determine, without undue experimentation, if a monoclonal antibody (e.g., a murine monoclonal or humanized antibody) has the same specificity as a monoclonal antibody used in the methods described herein by ascertaining whether the former prevents the latter from binding to EGFR. If the monoclonal antibody being tested competes with the monoclonal antibody of the invention, as shown by a decrease in binding by the monoclonal antibody of the invention, then the two monoclonal antibodies bind to the same, or a closely related, epitope. An alternative method for determining whether a monoclonal antibody has the specificity of a monoclonal antibody of the invention is to pre-incubate the monoclonal antibody of the invention with EGFR and then add the monoclonal antibody being tested to determine if the monoclonal antibody being tested is inhibited in its ability to bind EGFR. If the monoclonal antibody being tested is inhibited then, in all likelihood, it has the same, or functionally equivalent, epitopic specificity as the monoclonal antibody of the invention.

Use of Activatable Anti-EGFR Antibodies

The invention also provides a method of manufacturing activatable antibodies that in an activated state binds Epidermal Growth Factor Receptor (EGFR) by (a) culturing a cell comprising a nucleic acid construct that encodes the activatable antibody under conditions that lead to expression of the activatable antibody, wherein the activatable antibody comprises a masking moiety (MM), a cleavable moiety (CM), and an antibody or an antigen binding fragment thereof (AB) that specifically binds EGFR, (i) wherein the CM is a polypeptide that functions as a substrate for a protease; and (ii) wherein the CM is positioned in the activatable antibody such that, in an uncleaved state, the MM interferes with specific binding of the AB to EGFR and, when the activatable antibody is in a cleaved state, the MM does not interfere or compete with specific binding of the AB to EGFR; and (b) recovering the activatable antibody.

The invention provides methods of treating, preventing and/or delaying the onset or progression of, or alleviating a symptom of an indication, e.g., disease or disorder, associated with aberrant expression and/or activity of EGFR, e.g., an EGFR-related disorder or EGFR-related disease, in a subject using a therapeutic molecule, e.g., activatable antibodies that bind EGFR and/or conjugated activatable antibodies that bind EGFR, particularly activatable antibodies and/or conjugated activatable antibodies that bind and neutralize or otherwise inhibit at least one biological activity of EGFR and/or EGFR-mediated signaling.

In some embodiments, the indication, e.g., disease or disorder, associated with aberrant expression and/or activity of EGFR is a cancer. In some embodiments, the cancer is a breast cancer, e.g., by way of non-limiting example, the breast cancer is a triple-negative breast cancer. In some embodiments, the cancer is a triple-negative breast cancer. In some embodiments, the cancer is colorectal cancer. In some embodiments, the cancer is gastric cancer. In some embodiments, the cancer is glioblastoma. In some embodiments, the cancer is a head and neck cancer, e.g., by way of non-limiting example, esophageal cancer. In some embodiments, the cancer is an esophageal cancer. In some embodiments, the cancer is a lung cancer, e.g., by way of non-limiting example, non-small cell lung cancer. In some embodiments, the cancer is a non-small cell lung cancer. In some embodiments, the cancer is ovarian/endometrial cancer. In some embodiments, the cancer is pancreatic cancer. In some embodiments, the cancer is prostate cancer. In some embodiments, the cancer is a renal cancer. In some embodiments, the cancer is a sarcoma, e.g., by way of non-limiting example, osteosarcoma. In some embodiments, the cancer is an osteosarcoma. In some embodiments, the cancer is a skin cancer, e.g., by way of non-limiting example, squamous cell cancer, basal cell carcinoma, and/or melanoma. In some embodiments, the cancer is a squamous cell cancer. In some embodiments, the cancer is a basal cell carcinoma. In some embodiments, the cancer is a melanoma.

In some embodiments, the indication, e.g., disease or disorder, associated with aberrant expression and/or activity of EGFR is an inflammatory disorder and/or an autoimmune disease. In some embodiments, the inflammatory and/or autoimmune disease is psoriasis.

The therapeutic molecule, e.g., activatable anti-EGFR antibody and/or conjugated anti-EGFR activatable antibody, can be administered at any stage of the disease. For example, a therapeutic molecule can be administered to a patient suffering cancer of any stage, from early to metastatic. For example, therapeutic molecule can be administered to a patient suffering from an inflammatory disorder and/or autoimmune disease of any stage, from early onset to an advanced stage. It is to be understood that the terms subject and patient are used interchangeably herein.

The therapeutic molecules, e.g. activatable anti-EGFR antibodies and/or conjugated activatable anti-EGFR antibodies, are also useful in other therapeutic indications and treatment regimens. For example, the therapeutic molecules of the embodiments provided herein can be used in a treatment regimen that includes neoadjuvant therapy.

In some embodiments, the therapeutic molecules, e.g. activatable anti-EGFR antibodies and/or conjugated activatable anti-EGFR antibodies, are administered during and/or after treatment in combination with one or more additional agents such as, by way of non-limiting example, a chemotherapeutic agent. In some embodiments, the therapeutic molecule and the additional agent(s) are administered simultaneously. For example, the therapeutic molecule and the additional agent(s) can be formulated in a single composition or administered as two or more separate compositions. In some embodiments, the therapeutic molecule and the additional agent(s) are administered sequentially.

The invention also provides methods of preventing, delaying the progression of, treating, alleviating a symptom of, or otherwise ameliorating an EGFR-related disorder, for example, cancer, in a subject by administering a therapeutically effective amount of an activatable anti-EGFR antibody described herein to a subject in need thereof.

The invention also provides methods of inhibiting angiogenesis in a subject by administering a therapeutically effective amount of an activatable anti-EGFR antibody described herein to a subject in need thereof.

In some embodiments, the subject is a mammal. In some embodiments, the subject is a human. In some embodiments, the subject is a non-human mammal, such as a rodent, a non-human primate, companion animal (e.g., cat, dog, horse), farm animal, work animal, or zoo animal.

The activatable anti-EGFR antibody and therapeutic formulations thereof are administered to a subject suffering from or susceptible to a disease or disorder associated with aberrant EGFR expression and/or activity. A subject suffering from or susceptible to a disease or disorder associated with aberrant EGFR expression and/or activity is identified using any of a variety of methods known in the art. For example, subjects suffering from cancer or other neoplastic condition are identified using any of a variety of clinical and/or laboratory tests such as, physical examination and blood, urine and stool analysis to evaluate health status.

Administration of an activatable anti-EGFR antibody to a patient suffering from a disease or disorder associated with aberrant EGFR expression and/or activity is considered successful if any of a variety of laboratory or clinical objectives is achieved. For example, administration of an activatable anti-EGFR antibody to a patient suffering from a disease or disorder associated with aberrant EGFR expression and/or activity is considered successful if one or more of the symptoms associated with the disease or disorder is alleviated, reduced, inhibited or does not progress to a further, i.e., worse, state. Administration of an activatable anti-EGFR antibody to a patient suffering from a disease or disorder associated with aberrant EGFR expression and/or activity is considered successful if the diabetes enters remission or does not progress to a further, i.e., worse, state.

In some embodiments, the activatable anti-EGFR antibody is administered during and/or after treatment in combination with one or more additional agents such as, for example, a chemotherapeutic agent. In some embodiments, the activatable anti-EGFR antibody and the additional agent(s) are administered simultaneously. For example, the activatable anti-EGFR antibody and the additional agent(s) can be formulated in a single composition or administered as two or more separate compositions. In some embodiments, the activatable anti-EGFR antibody and the additional agent(s) are administered sequentially.

It will be appreciated that administration of therapeutic entities in accordance with the invention will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, PA (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semisolid gels, and semi-solid mixtures containing carbowax. Any of the foregoing mixtures may be appropriate in treatments and therapies in accordance with the present invention, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

Therapeutic formulations of the invention, which include an activatable anti-EGFR antibody, are used to prevent, treat or otherwise ameliorate a disease or disorder associated with aberrant EGFR expression and/or activity. For example, therapeutic formulations of the invention, which include an activatable anti-EGFR antibody, are used to treat or otherwise ameliorate a cancer or other neoplastic condition.

Increased proteolysis is known to be a hallmark of cancer. (See e.g., Affara N I, et al. "Delineating protease functions during cancer development." Methods Mol Biol. 539 (2009): 1-32). Progression, invasion and metastasis of tumors result from several interdependent processes in which proteases are implicated.

Efficaciousness of prevention, amelioration or treatment is determined in association with any known method for diagnosing or treating the disease or disorder associated with aberrant EGFR expression and/or activity. Prolonging the survival of a subject or otherwise delaying the progression of the disease or disorder associated with aberrant EGFR expression and/or activity in a subject indicates that the activatable antibody confers a clinical benefit.

Activatable anti-EGFR antibodies can be administered in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where activatable antibody fragments are used, the smallest fragment that specifically binds to the binding domain of the target protein is used. For example, based upon the variable-region sequences of an antibody, peptide molecules can be designed that retain the ability to bind the target protein sequence. Such peptides can be synthesized chemically and/or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, such as, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods.

In some embodiments, the activatable antibody contains a detectable label. An intact antibody, or a fragment thereof (e.g., Fab, scFv, or $F(ab)_2$) is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, immunochemical staining, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N J, 1995; "Immunoassay", E. Diamandis and T. Christopoulus, Academic Press, Inc., San Diego, C A, 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Diagnostic and Prophylactic Formulations

The anti-EGFR antibodies and/or activatable anti-EGFR antibodies of the invention are used in diagnostic and prophylactic formulations. In one embodiment, an anti-EGFR antibody and/or activatable anti-EGFR antibody is administered to patients that are at risk of developing one or more of the aforementioned cancer or other disorders. A patient's or organ's predisposition to one or more of the aforementioned disorders can be determined using genotypic, serological or biochemical markers.

In another embodiment of the invention, an anti-EGFR antibody and/or activatable anti-EGFR antibody is administered to human individuals diagnosed with a clinical indication associated with one or more of the aforementioned disorders. Upon diagnosis, an anti-EGFR antibody and/or activatable anti-EGFR antibody is administered to mitigate or reverse the effects of the clinical indication.

Antibodies and/or activatable antibodies of the invention are also useful in the detection of EGFR in patient samples and accordingly are useful as diagnostics. For example, the anti-EGFR antibodies and/or activatable anti-EGFR antibodies of the invention are used in in vitro assays, e.g., ELISA, to detect EGFR levels in a patient sample.

In one embodiment, an anti-EGFR antibody and/or activatable anti-EGFR antibody of the invention is immobilized on a solid support (e.g., the well(s) of a microtiter plate). The immobilized antibody and/or activatable antibody serves as a capture antibody for any EGFR that may be present in a test sample. Prior to contacting the immobilized antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of EGFR antigen in the test sample is determined by comparison with a standard curve developed from the standard samples.

It will be appreciated that based on the results obtained using the anti-EGFR antibodies of the invention in an in vitro diagnostic assay, it is possible to stage a disease in a subject based on expression levels of the EGFR antigen. For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Anti-EGFR antibodies and/or activatable anti-EGFR antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, activatable anti-EGFR antibodies having an enzymatically cleavable CM can be used to detect the presence or absence of an enzyme that is capable of cleaving the CM. Such activatable anti-EGFR antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of activated anti-EGFR antibodies (i.e., antibodies resulting from cleavage of an activatable anti-EGFR antibody) in a given cell or tissue of a given host organism. Such accumulation of activated anti-EGFR antibodies indicates not only that the tissue expresses enzymatic activity (or an increased reduction potential depending on the nature of the CM) but also that the tissue expresses target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. The AB can be one that binds a target antigen. Using methods familiar to one skilled in the art, a detectable label (e.g., a fluorescent label or radioactive label or radiotracer) can be conjugated to an AB or other region of an anti-EGFR antibody and/or activatable anti-EGFR antibody. Suitable detectable labels are discussed in the context of the above screening methods and additional specific examples are provided below. Using an AB specific to a protein or peptide of the disease state, along with a protease whose activity is elevated in the disease tissue of interest, activatable anti-EGFR antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated anti-EGFR antibodies in the disease tissue is enhanced relative to non-disease tissues.

In another example, activatable anti-EGFR antibodies can be used to detect the presence or absence of a cleaving agent in a sample. For example, where the activatable anti-EGFR antibodies contain a CM susceptible to cleavage by an enzyme, the activatable anti-EGFR antibodies can be used to detect (either qualitatively or quantitatively) the presence of an enzyme in the sample. In another example, where the activatable anti-EGFR antibodies contain a CM susceptible to cleavage by reducing agent, the activatable anti-EGFR antibodies can be used to detect (either qualitatively or quantitatively) the presence of reducing conditions in a sample. To facilitate analysis in these methods, the activatable antibodies can be detectably labeled, and can be bound to a support (e.g., a solid support, such as a slide or bead). The detectable label can be positioned on a portion of the activatable anti-EGFR antibody that is not released following cleavage, for example, the detectable label can be a quenched fluorescent label or other label that is not detectable until cleavage has occurred. The assay can be conducted by, for example, contacting the immobilized, detectably labeled activatable anti-EGFR antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the activatable anti-EGFR antibodies prior to contacting with the sample e.g., the presence of and/or an increase in detectable signal due to cleavage of the activatable antibody by the cleaving agent in the sample.

Such detection methods can be adapted to also provide for detection of the presence or absence of a target that is capable of binding the AB of the activatable anti-EGFR antibodies when cleaved. Thus, the assays can be adapted to assess the presence or absence of a cleaving agent and the presence or absence of a target of interest (EGFR). The presence or absence of the cleaving agent can be detected by the presence of and/or an increase in detectable label of the activatable anti-EGFR antibodies as described above, and the presence or absence of the target can be detected by detection of a target-AB complex e.g., by use of a detectably labeled anti-target antibody.

Activatable anti-EGFR antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable anti-EGFR antibody is labeled with a detectable label. The detectable label may be a fluorescent dye, (e.g. a fluorescein derivative, e.g., Fluorescein Isothiocyanate (FITC), Rhodamine Isothiocyanate (TRITC), a near infrared (NTR) dye (e.g., Qdot® nanocrystals), a colloidal metal, a hapten, a radioactive marker, biotin and an amplification reagent such as streptavidin, or an enzyme (e.g., horseradish peroxidase or alkaline phosphatase).

Detection of the label in a sample that has been incubated with the labeled, activatable anti-EGFR antibody indicates that the sample contains the target, i.e., EGFR, and contains a protease that is specific for the CM of the activatable anti-EGFR antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable anti-EGFR antibody. In some embodiments, the presence of the target can be confirmed using an agent that is specific for the target, e.g., another anti-EGFR antibody, or the detectable label can be competed with unlabeled EGFR. In some embodiments, unlabeled activatable anti-EGFR antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target, i.e., EGFR, and contains a protease that is specific for the CM of the activatable anti-EGFR antibody.

These techniques are also useful in kits and/or as reagents for the detection, identification or characterization of protease activity in a variety of cells, tissues, and organisms based on the protease-specific CM in the activatable anti-EGFR antibody.

In some embodiments, in situ imaging and/or in vivo imaging are useful in methods to identify which patients to treat. For example, in in situ imaging, the activatable anti-EGFR antibodies are used to screen patient samples to identify those patients having the appropriate protease(s) and target(s) at the appropriate location, e.g., at a tumor site.

In some embodiments in situ imaging is used to identify or otherwise refine a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested (e.g., accumulate activated antibodies at the disease site) are identified as suitable candidates for treatment with such an anti-EGFR activatable antibody comprising such a CM. Likewise, patients that test negative for either or both of the target (e.g., EGFR) and the protease that cleaves the substrate in the CM in the activatable antibody being tested using these methods might be identified as suitable candidates for another form of therapy (i.e., not suitable for treatment with the anti-EGFR activatable antibody being tested). In some embodiments, such patients that test negative with respect to a first anti-EGFR activatable antibody can be tested with other anti-EGFR activatable antibodies comprising different CMs until a suitable anti-EGFR activatable antibody for treatment is identified (e.g., an anti-EGFR activatable antibody comprising a CM that is cleaved by the patient at the site of disease).

In some embodiments in vivo imaging is used to identify or otherwise refine a patient population suitable for treatment with an anti-EGFR activatable antibody of the disclosure. For example, patients that test positive for both the target (e.g., EGFR) and a protease that cleaves the substrate in the cleavable moiety (CM) of the anti-EGFR activatable antibody being tested (e.g., accumulate activated antibodies at the disease site) are identified as suitable candidates for treatment with such an anti-EGFR activatable antibody comprising such a CM. Likewise, patients that test negative might be identified as suitable candidates for another form of therapy (i.e., not suitable for treatment with the anti-EGFR activatable antibody being tested). In some embodiments, such patients that test negative with respect to a first anti-EGFR activatable antibody can be tested with other anti-EGFR activatable antibodies comprising different CMs until a suitable anti-EGFR activatable antibody for treatment is identified (e.g., an anti-EGFR activatable antibody comprising a CM that is cleaved by the patient at the site of disease).

Pharmaceutical Compositions

The activatable anti-EGFR antibodies of the invention (also referred to herein as "active compounds"), and derivatives, fragments, analogs and homologs thereof, can be incorporated into pharmaceutical compositions suitable for administration. Such compositions typically comprise the activatable antibody and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The invention will be further described in the following examples, which do not limit the scope of the invention described in the claims.

EXAMPLES

Example 1. Materials and Methods

Activatable anti-EGFR antibody expression and purification. The cDNA coding for the heavy chain and the light chain of each of the activatable anti-EGFR antibodies were separately cloned into a modified pcDNA3.1 mammalian expression vector (Life Technologies). Expi293™ cells (Life Technologies) were transiently transfected with the plasmids for each activatable anti-EGFR antibody for 5-7 days using ExpiFectamine™ transfection reagent (Life Technologies) following the manufacturer's instructions. The activatable anti-EGFR antibodies were purified using a HiTrap™ Mab Select SuRe™ protein A column (GE Healthcare) coupled to an AKTA purifier (GE Healthcare). The purity and the homogeneity of purified activatable anti-EGFR antibodies were analyzed by SDS-PAGE in reducing and non-reducing conditions and size exclusion chromatography using a Superdex™ 200, 10/300 GL column (GE Healthcare), respectively.

Example 2. In Vitro Activity of Activatable Anti-EGFR Antibodies

This Example describes the ability of a masking moiety of an activatable antibody of the disclosure to reduce the ability of such an anti-EGFR activatable antibody to bind to EGFR compared to EGFR binding by EGFR antibody cetuximab.

The abilities of the following anti-EGFR antibody and activatable antibodies to bind to human EGFR in an in vitro binding assay were evaluated: cetuximab; a control anti-EGFR activatable antibody having the masked light chain amino acid sequence shown below in SEQ ID NO: 74 and the heavy chain sequence of SEQ ID NO: 2; and the following C225v5 activatable antibodies: the Des-1-3954-1204-c225v5 activatable antibody (heavy chain sequence of SEQ ID NO: 2 and masked light chain sequence of SEQ ID NO: 4); the Des-2-3954-1204-c225v5 activatable antibody (SEQ ID NO: 2 and SEQ ID NO: 6); the Des-3-3954-1204-c225v5 activatable antibody (SEQ ID NO: 2 and SEQ ID NO: 8); the Des-4-3954-1204-c225v5 activatable antibody (SEQ ID NO: 2 and SEQ ID NO: 10); and the Des-5-3954-1204-c225v5 activatable antibody (SEQ ID NO: 2 and SEQ ID NO: 12).

```
Control anti-EGFR activatable antibody:
[Spacer (SEQ ID NO: 75)][Mask (SEQ ID NO: 24)]
[Linker 1 (SEQ ID NO: 26)][1204 Substrate (SEQ ID
NO: 28)][Linker 2 (SEQ ID NO: 30)][C225 (SEQ ID
NO: 32)]
                                    (SEQ ID NO: 74)
[QGQSGQ][CISPRGCPDGPYVMY][GSSGGSGGSGGSG][LSGRSDNH]

[GSSGT][QILLTQSPVILSVSPGERVSFSCRASQSIGTNIHWYQQRTNG
```

-continued

SPRLLIKYASESISGIPSRFSGSGSGTDFTLSINSVESEDIADYYCQQNN

NWPTTFGAGTKLELKRTVAAPSVFIFPPSDEQLKSGTASVVCLLNNFYPR

EAKVQWKVDNALQSGNSQESVTEQDSKDSTYSLSSTLTLSKADYEKHKVY

ACEVTHQGLSSPVTKSFNRGEC*]

Briefly, 96-well plates were coated with 1 microgram per milliliter (ug/mL) EGFR overnight at 4° C. After blocking and washing, different concentrations of C225 antibody or of each of the activatable antibodies were added to the coated plates and incubated at room temperature for 1 h. The amounts of bound cetuximab or activatable antibody were detected by anti-human IgG (Fab)$_2$-HRP. The $K_d$ for each antibody or activatable antibody was calculated using Prism 6 program.

The binding of the control anti-EGFR activatable antibody (heavy chain sequence of SEQ ID NO: 2 and masked light chain sequence of SEQ ID NO: 74) and each of the other C225v5 activatable antibodies to EGFR was reduced by more than 50-fold relative to cetuximab. The apparent $K_d$ of cetuximab was approximately 0.12 nM as compared to a range of approximately 6.5 to 8.89 nM for the tested anti-EGFR activatable antibodies.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following.

What is claimed is:

1. A method of detecting presence or absence of a cleaving agent and Epidermal Growth Factor Receptor (EGFR) in a subject or a sample, the method comprising:
   (a) contacting a subject or a sample with an anti-EGFR activatable antibody comprising
      an antibody or an antigen-binding fragment thereof (AB) that specifically binds to EGFR, wherein the AB comprises
      (I) a heavy chain comprising:
         (i) heavy chain complementarity determining regions (HCDRs), wherein the HCDRs of the AB are the HCDRs of the heavy chain amino acid sequence of SEQ ID NO: 2, and
         (ii) at least one of the following amino acid sequence features: (1) the heavy chain of the AB has a glutamine residue at the position corresponding to position 88 of SEQ ID NO: 2, (2) the heavy chain of the AB has an alanine residue at the position corresponding to position 299 of SEQ ID NO: 2, and (3) the heavy chain of the AB has a lysine residue at the position corresponding to position 216 of SEQ ID NO: 2;
      (II) a light chain comprising:
         (i) light chain complementarity determining regions (LCDRs), wherein the LCDRs are the LCDRs of the light chain amino acid sequence of SEQ ID NO: 32; and
         (ii) a spacer sequence comprising an amino acid sequence selected from the group consisting of: SEQ ID NOs: 14, 16, 18, 20, and 22,
      wherein the light chain amino acid sequence is coupled to a masking moiety (MM) via a cleavable moiety (CM) to produce a masked light chain,
      wherein the MM comprises the amino acid sequence of SEQ ID NO: 76, wherein the MM inhibits the binding of the AB of the anti-EGFR activatable antibody in an uncleaved state to EGFR,
      wherein the CM is a polypeptide that functions as a substrate for a protease, and
      wherein the anti-EGFR activatable antibody in the uncleaved state has a structural arrangement from N-terminus to C-terminus as follows: Spacer Sequence-MM-Linking Peptide 1 (LP1)-CM-Linking Peptide 2 (LP2)-AB or AB LP2 CM LP1 MM Spacer Sequence; and
   (b) measuring a level of activated anti-EGFR activatable antibody in the subject or sample,
   wherein a detectable level of activated anti-EGFR activatable antibody in the subject or sample indicates that the cleaving agent and EGFR are present in the subject or sample, and wherein no detectable level of activated anti-EGFR activatable antibody in the subject or sample indicates that the cleaving agent, EGFR or both the cleaving agent and EGFR are absent in the subject or sample.

2. The method of claim 1, wherein the anti-EGFR activatable antibody comprises a detectable label.

3. The method of claim 2, wherein the detectable label comprises an imaging agent, a radioisotope, a contrasting agent, an enzyme, a fluorescent label, a chromophore, a dye, one or more metal ions, or a ligand-based label.

4. The method of claim 1, wherein the method is an in vivo method, an in situ method, an ex vivo method, or in vitro method.

5. The method of claim 1, wherein the subject has an EGFR-related disorder, or wherein the sample is from the subject having the EGFR-related disorder, wherein the EGFR-related disorder is a cancer.

6. The method of claim 5, wherein the cancer is breast cancer, colorectal cancer, gastric cancer, glioblastoma, head and neck cancer, lung cancer, ovarian cancer, endometrial cancer, pancreatic cancer, prostate cancer, renal cancer, sarcoma, or skin cancer.

7. The method of claim 1, wherein the subject has an EGFR-related disorder, or wherein the sample is from the subject having the EGFR-related disorder, wherein the EGFR-related disorder is psoriasis.

8. The method of claim 1, wherein the AB is conjugated to an agent.

9. The method of claim 8, wherein the agent is a toxin or fragment thereof.

10. The method of claim 9, wherein the agent is selected from the group consisting of a dolastatin, an auristatin or derivative thereof, a maytansinoid or a derivative thereof, a duocarmycin or derivative thereof, and a calicheamicin or derivative thereof.

11. The method of claim 1, wherein the antigen-binding fragment thereof is selected from the group consisting of a Fab fragment, a F(ab')2 fragment, a scFv, and a scAb.

12. The method of claim 1, wherein the anti-EGFR activatable antibody in an uncleaved state comprises a combination of a heavy chain and a masked light chain selected from the group consisting of:
   (a) a heavy chain comprising amino acid sequence of SEQ ID NO: 2 and a masked light chain comprising the amino acid sequence of SEQ ID NO: 4;
   (b) a heavy chain comprising amino acid sequence of SEQ ID NO: 2 and a masked light chain comprising the amino acid sequence of SEQ ID NO: 6;
   (c) a heavy chain comprising amino acid sequence of SEQ ID NO: 2 and a masked light chain comprising the amino acid sequence of SEQ ID NO: 8;
   (d) a heavy chain comprising amino acid sequence of SEQ ID NO: 2 and a masked light chain comprising the amino acid sequence of SEQ ID NO: 10;
   (e) a heavy chain comprising amino acid sequence of SEQ ID NO: 2 and a masked light chain comprising the amino acid sequence of SEQ ID NO: 12;
   (f) a heavy chain comprising amino acid sequence of SEQ ID NO: 34 and a masked light chain comprising the amino acid sequence of SEQ ID NO: 4;
   (g) a heavy chain comprising amino acid sequence of SEQ ID NO: 34 and a masked light chain comprising the amino acid sequence of SEQ ID NO: 6;
   (h) a heavy chain comprising amino acid sequence of SEQ ID NO: 34 and a masked light chain comprising the amino acid sequence of SEQ ID NO: 8;
   (i) a heavy chain comprising amino acid sequence of SEQ ID NO: 34 and a masked light chain comprising the amino acid sequence of SEQ ID NO: 10;
   (j) a heavy chain comprising amino acid sequence of SEQ ID NO: 34 and a masked light chain comprising the amino acid sequence of SEQ ID NO: 12;
   (k) a heavy chain comprising amino acid sequence of SEQ ID NO: 36 and a masked light chain comprising the amino acid sequence of SEQ ID NO: 4;
   (l) a heavy chain comprising amino acid sequence of SEQ ID NO: 36 and a masked light chain comprising the amino acid sequence of SEQ ID NO: 6;
   (m) a heavy chain comprising amino acid sequence of SEQ ID NO: 36 and a masked light chain comprising the amino acid sequence of SEQ ID NO: 8;

(n) a heavy chain comprising amino acid sequence of SEQ ID NO: 36 and a masked light chain comprising the amino acid sequence of SEQ ID NO: 10; and (o) a heavy chain comprising amino acid sequence of SEQ ID NO: 36 and a masked light chain comprising the amino acid sequence of SEQ ID NO: 12.

13. The method of claim 1, wherein the AB has an equilibrium dissociation constant of between 1 pM and 100 nM for binding to EGFR.

14. The method of claim 1, wherein the MM has an equilibrium dissociation constant for binding to the AB that is greater than the equilibrium dissociation constant of the AB to EGFR.

15. The method of claim 1, wherein the protease is co-localized with EGFR in a tissue, and wherein the protease cleaves the CM in the anti-EGFR activatable antibody when the anti-EGFR activatable antibody is exposed to the protease.

16. The method of claim 8, wherein the agent is auristatin E or a derivative thereof.

17. The method of claim 8, wherein the agent is monomethyl auristatin E (MMAE).

18. The method of claim 8, wherein the agent is monomethyl auristatin D (MMAD).

19. The method of claim 8, wherein the agent is DM1 or DM4.

20. The method of claim 8, wherein the agent is conjugated to the AB via a linker.

21. The method of claim 20, wherein the linker is a cleavable linker.

22. The method of claim 20, wherein the linker is a non-cleavable linker.

23. The method of claim 1, wherein the anti-EGFR activatable antibody comprises a detectable moiety.

24. The method of claim 23, wherein the detectable moiety is a diagnostic agent.

25. The method of claim 1, wherein the MM comprises an amino acid sequence selected from the group consisting of: SEQ ID NOs: 24, 77-80, and 82-109.

* * * * *

SEQUENCE LISTING

```
<160> NUMBER OF SEQ ID NOS: 150

<210> SEQ ID NO 1
<211> LENGTH: 1350
<212> TYPE: DNA
<213> ORGANISM: Artificial Sequence
<220> FEATURE:
<223> OTHER INFORMATION: C225v5 Activatable Antibody Heavy Chain

<400> SEQUENCE: 1
caggtgcagc tgaaacagag cggcccgggc ctggtgcagc cgagccagag cctgagcatt        60
acctgcaccg tgagcggctt tagcctgacc aactatggcg tgcattgggt gcgccagagc       120
ccgggcaaag gcctggaatg gctgggcgtg atttggagcg gcggcaacac cgattataac       180
accccgttta ccagccgcct gagcattaac aaagataaca gcaaaagcca ggtgtttttt       240
aaaatgaaca gcctgcaaag ccaggatacc gcgatttatt attgcgcgcg cgcgctgacc       300
tattatgatt atgaatttgc gtattggggc cagggcaccc tggtgaccgt gagcgcggct       360
agcaccaagg gcccatcggt cttccccctg gcacctcct ccaagagcac ctctgggggc       420
acagcggccc tgggctgcct ggtcaaggac tacttccccg aaccggtgac ggtgtcgtgg       480
aactcaggcg ccctgaccag cggcgtgcac accttcccgg ctgtcctaca gtcctcagga       540
ctctactccc tcagcagcgt ggtgaccgtg ccctccagca gcttgggcac ccagacctac       600
atctgcaacg tgaatcacaa gcccagcaac accaaggtgg acaagaaagt tgagcccaaa       660
tcttgtgaca aaactcacac atgcccaccg tgcccagcac ctgaactcct ggggggaccg       720
tcagtcttcc tcttccccccc aaaacccaag gacaccctca tgatctcccg gaccccctgag      780 gtcacatgcg tggtggtgga cgtgagccac gaagaccctg aggtcaagtt caactggtac       840
gtggacggcg tggaggtgca taatgccaag acaaagccgc gggaggagca gtacaacagc       900
acgtaccgtg tggtcagcgt cctcaccgtc ctgcaccagg actggctgaa tggcaaggag       960
tacaagtgca aggtctccaa caaagccctc ccagccccca tcgagaaaac catctccaaa      1020
gccaaagggc agccccgaga accacaggtg tacaccctgc ccccatcccg ggatgaactg      1080
accaagaacc aggtcagcct gacctgcctg gtcaaaggct tctatcccag cgacatcgcc      1140
gtggagtggg agagcaatgg gcagccggag aacaactaca agaccacgcc tcccgtgctg      1200
gactccgacg gctccttctt cctctacagc aagctcaccg tggacaagag caggtggcag      1260
caggggaacg tcttctcatg ctccgtgatg catgaggctc tgcacaacca ctacacgcag      1320
aagagcctct ccctgtctcc gggtaaatga                                       1350
```

```
<210> SEQ ID NO 2
<211> LENGTH: 449
<212> TYPE: PRT
<213> ORGANISM: Artificial Sequence
<220> FEATURE:
<223> OTHER INFORMATION: C225v5 Activatable Antibody Heavy Chain

<400> SEQUENCE: 2

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365
```

```
Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 3
<211> LENGTH: 783
<212> TYPE: DNA
<213> ORGANISM: Artificial Sequence
<220> FEATURE:
<223> OTHER INFORMATION: Des-1-3954-1204-C225 Activatable Antibody Light
      Chain

<400> SEQUENCE: 3
ggccagtctg gccagtgcat ctcacctcgt ggttgtccgg acggcccata cgtcatgtac      60
ggctcgagcg gtggcagcgg tggctctggt ggatccggtc tgagcggccg ttccgataat     120
catggcagta gcggtaccca gatcttgctg acccagagcc cggtgattct gagcgtgagc     180
ccgggcgaac gtgtgagctt tagctgccgc gcgagccaga gcattggcac caacattcat     240
tggtatcagc agcgcaccaa cggcagcccg cgcctgctga ttaaatatgc gagcgaaagc     300
attagcggca ttccgagccg ctttagcggc agcggcagcg gcaccgattt taccctgagc     360
attaacagcg tggaaagcga agatattgcg gattattatt gccagcagaa caacaactgg     420
ccgaccacct ttggcgcggg caccaaactg gaactgaaac gtacggtggc tgcaccatct     480
gtcttcatct tcccgccatc tgatgagcag ttgaaatctg gaactgcctc tgttgtgtgc     540
ctgctgaata acttctatcc cagagaggcc aaagtacagt ggaaggtgga taacgccctc     600
caatcgggta actcccagga gagtgtcaca gagcaggaca gcaaggacag cacctacagc     660
ctcagcagca ccctgacgct gagcaaagca gactacgaga aacacaaagt ctacgcctgc     720
gaagtcaccc atcagggcct gagctcgccc gtcacaaaga gcttcaacag gggagagtgt     780
tag                                                                  783

<210> SEQ ID NO 4
<211> LENGTH: 260
<212> TYPE: PRT
<213> ORGANISM: Artificial Sequence
<220> FEATURE:
<223> OTHER INFORMATION: Des-1-3954-1204-C225 Activatable Antibody Light
      Chain

<400> SEQUENCE: 4

Gly Gln Ser Gly Gln Cys Ile Ser Pro Arg Gly Cys Pro Asp Gly Pro
1               5                   10                  15

Tyr Val Met Tyr Gly Ser Ser Gly Gly Ser Gly Gly Ser Gly Gly Ser
            20                  25                  30

Gly Leu Ser Gly Arg Ser Asp Asn His Gly Ser Ser Gly Thr Gln Ile
        35                  40                  45

Leu Leu Thr Gln Ser Pro Val Ile Leu Ser Val Ser Pro Gly Glu Arg
    50                  55                  60
```

Val Ser Phe Ser Cys Arg Ala Ser Gln Ser Ile Gly Thr Asn Ile His
65                  70                  75                  80

Trp Tyr Gln Gln Arg Thr Asn Gly Ser Pro Arg Leu Leu Ile Lys Tyr
                85                  90                  95

Ala Ser Glu Ser Ile Ser Gly Ile Pro Ser Arg Phe Ser Gly Ser Gly
            100                 105                 110

Ser Gly Thr Asp Phe Thr Leu Ser Ile Asn Ser Val Glu Ser Glu Asp
        115                 120                 125

Ile Ala Asp Tyr Tyr Cys Gln Gln Asn Asn Asn Trp Pro Thr Thr Phe
    130                 135                 140

Gly Ala Gly Thr Lys Leu Glu Leu Lys Arg Thr Val Ala Ala Pro Ser
145                 150                 155                 160

Val Phe Ile Phe Pro Pro Ser Asp Glu Gln Leu Lys Ser Gly Thr Ala
                165                 170                 175

Ser Val Val Cys Leu Leu Asn Asn Phe Tyr Pro Arg Glu Ala Lys Val
            180                 185                 190

Gln Trp Lys Val Asp Asn Ala Leu Gln Ser Gly Asn Ser Gln Glu Ser
        195                 200                 205

Val Thr Glu Gln Asp Ser Lys Asp Ser Thr Tyr Ser Leu Ser Ser Thr
    210                 215                 220

Leu Thr Leu Ser Lys Ala Asp Tyr Glu Lys His Lys Val Tyr Ala Cys
225                 230                 235                 240

Glu Val Thr His Gln Gly Leu Ser Ser Pro Val Thr Lys Ser Phe Asn
                245                 250                 255

Arg Gly Glu Cys
            260

<210> SEQ ID NO 5
<211> LENGTH: 780
<212> TYPE: DNA
<213> ORGANISM: Artificial Sequence
<220> FEATURE:
<223> OTHER INFORMATION: Des-2-3954-1204-C225 Activatable Antibody Light
      Chain

<400> SEQUENCE: 5
cagtctggcc agtgcatctc acctcgtggt tgtccggacg gcccatacgt catgtacggc    60
tcgagcggtg cagcggtgg ctctggtgga tccggtctga gcggccgttc cgataatcat    120
ggcagtagcg gtacccagat cttgctgacc cagagcccgg tgattctgag cgtgagcccg    180
ggcgaacgtg tgagctttag ctgccgcgcg agccagagca ttggcaccaa cattcattgg    240
tatcagcagc gcaccaacgg cagcccgcgc ctgctgatta aatatgcgag cgaaagcatt    300
agcggcattc cgagccgctt tagcggcagc ggcagcggca ccgatttac cctgagcatt    360 aacagcgtgg aaagcgaaga tattgcggat tattattgcc agcagaacaa caactggccg    420
accacctttg gcgcgggcac caaactggaa ctgaaacgta cggtggctgc accatctgtc    480
ttcatcttcc cgccatctga tgagcagttg aaatctggaa ctgcctctgt tgtgtgcctg    540
ctgaataact tctatcccag agaggccaaa gtacagtgga aggtggataa cgccctccaa    600
tcgggtaact cccaggagag tgtcacagag caggacagca aggacagcac ctacagcctc    660
agcagcaccc tgacgctgag caaagcagac tacgagaaac acaaagtcta cgcctgcgaa    720
gtcacccatc agggcctgag ctcgcccgtc acaaagagct tcaacagggg agagtgttag    780

<210> SEQ ID NO 6

```
<211> LENGTH: 259
<212> TYPE: PRT
<213> ORGANISM: Artificial Sequence
<220> FEATURE:
<223> OTHER INFORMATION: Des-2-3954-1204-C225 Activatable Antibody Light
      Chain

<400> SEQUENCE: 6

Gln Ser Gly Gln Cys Ile Ser Pro Arg Gly Cys Pro Asp Gly Pro Tyr
1               5                   10                  15

Val Met Tyr Gly Ser Ser Gly Gly Ser Gly Gly Ser Gly
            20                  25                  30

Leu Ser Gly Arg Ser Asp Asn His Gly Ser Ser Gly Thr Gln Ile Leu
                35                  40                  45

Leu Thr Gln Ser Pro Val Ile Leu Ser Val Ser Pro Gly Glu Arg Val
50                  55                  60

Ser Phe Ser Cys Arg Ala Ser Gln Ser Ile Gly Thr Asn Ile His Trp
65                  70                  75                  80

Tyr Gln Gln Arg Thr Asn Gly Ser Pro Arg Leu Leu Ile Lys Tyr Ala
                85                  90                  95

Ser Glu Ser Ile Ser Gly Ile Pro Ser Arg Phe Ser Gly Ser Gly Ser
                100                 105                 110

Gly Thr Asp Phe Thr Leu Ser Ile Asn Ser Val Glu Ser Glu Asp Ile
            115                 120                 125

Ala Asp Tyr Tyr Cys Gln Gln Asn Asn Asn Trp Pro Thr Thr Phe Gly
130                 135                 140

Ala Gly Thr Lys Leu Glu Leu Lys Arg Thr Val Ala Ala Pro Ser Val
145                 150                 155                 160

Phe Ile Phe Pro Pro Ser Asp Glu Gln Leu Lys Ser Gly Thr Ala Ser
                165                 170                 175

Val Val Cys Leu Leu Asn Asn Phe Tyr Pro Arg Glu Ala Lys Val Gln
                180                 185                 190

Trp Lys Val Asp Asn Ala Leu Gln Ser Gly Asn Ser Gln Glu Ser Val
            195                 200                 205

Thr Glu Gln Asp Ser Lys Asp Ser Thr Tyr Ser Leu Ser Ser Thr Leu
210                 215                 220

Thr Leu Ser Lys Ala Asp Tyr Glu Lys His Lys Val Tyr Ala Cys Glu
225                 230                 235                 240

Val Thr His Gln Gly Leu Ser Ser Pro Val Thr Lys Ser Phe Asn Arg
                245                 250                 255

Gly Glu Cys

<210> SEQ ID NO 7
<211> LENGTH: 777
<212> TYPE: DNA
<213> ORGANISM: Artificial Sequence
<220> FEATURE:
<223> OTHER INFORMATION: Des-3-3954-1204-C225 Activatable Antibody Light
      Chain

<400> SEQUENCE: 7
tctggccagt gcatctcacc tcgtggttgt ccggacggcc catacgtcat gtacggctcg      60
agcggtggca gcggtggctc tggtggatcc ggtctgagcg gccgttccga taatcatggc     120
agtagcggta cccagatctt gctgacccag agcccggtga ttctgagcgt gagcccgggc     180
gaacgtgtga gctttagctg ccgcgcgagc cagagcattg gcaccaacat tcattggtat     240
cagcagcgca ccaacggcag cccgcgcctg ctgattaaat atgcgagcga aagcattagc     300
```

```
ggcattccga gccgctttag cggcagcggc agcggcaccg attttacccct gagcattaac    360 agcgtggaaa gcgaagatat tgcggattat tattgccagc agaacaacaa ctggccgacc    420
acctttggcg cgggcaccaa actggaactg aaacgtacgg tggctgcacc atctgtcttc    480
atcttcccgc catctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag gacagcaagg acagcaccta cagcctcagc    660
agcaccctga cgctgagcaa agcagactac gagaaacaca agtctacgc ctgcgaagtc    720 acccatcagg gcctgagctc gcccgtcaca aagagcttca acaggggaga gtgttag      777
```

<210> SEQ ID NO 8
<211> LENGTH: 258
<212> TYPE: PRT
<213> ORGANISM: Artificial Sequence
<220> FEATURE:
<223> OTHER INFORMATION: Des-3-3954-1204-C225 Activatable Antibody Light Chain

<400> SEQUENCE: 8

```
Ser Gly Gln Cys Ile Ser Pro Arg Gly Cys Pro Asp Gly Pro Tyr Val
1               5                   10                  15

Met Tyr Gly Ser Ser Gly Gly Ser Gly Gly Ser Gly Gly Ser Gly Leu
            20                  25                  30

Ser Gly Arg Ser Asp Asn His Gly Ser Ser Gly Thr Gln Ile Leu Leu
        35                  40                  45

Thr Gln Ser Pro Val Ile Leu Ser Val Ser Pro Gly Glu Arg Val Ser
    50                  55                  60

Phe Ser Cys Arg Ala Ser Gln Ser Ile Gly Thr Asn Ile His Trp Tyr
65                  70                  75                  80

Gln Gln Arg Thr Asn Gly Ser Pro Arg Leu Leu Ile Lys Tyr Ala Ser
                85                  90                  95

Glu Ser Ile Ser Gly Ile Pro Ser Arg Phe Ser Gly Ser Gly Ser Gly
            100                 105                 110

Thr Asp Phe Thr Leu Ser Ile Asn Ser Val Glu Ser Glu Asp Ile Ala
        115                 120                 125

Asp Tyr Tyr Cys Gln Gln Asn Asn Asn Trp Pro Thr Thr Phe Gly Ala
    130                 135                 140

Gly Thr Lys Leu Glu Leu Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Ser Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys
```

<210> SEQ ID NO 9
<211> LENGTH: 774
<212> TYPE: DNA
<213> ORGANISM: Artificial Sequence
<220> FEATURE:
<223> OTHER INFORMATION: Des-4-3954-1204-C225 Activatable Antibody Light Chain

<400> SEQUENCE: 9

```
ggccagtgca tctcacctcg tggttgtccg gacggcccat acgtcatgta cggctcgagc      60
ggtggcagcg gtggctctgg tggatccggt ctgagcggcc gttccgataa tcatggcagt     120
agcggtaccc agatcttgct gacccagagc ccggtgattc tgagcgtgag cccgggcgaa     180
cgtgtgagct ttagctgccg cgcgagccag agcattggca ccaacattca ttggtatcag     240
cagcgcacca acggcagccc gcgcctgctg attaaatatg cgagcgaaag cattagcggc     300
attccgagcc gctttagcgg cagcggcagc ggcaccgatt ttaccctgag cattaacagc     360
gtggaaagcg aagatattgc ggattattat tgccagcaga caacaactg gccgaccacc     420
tttggcgcgg gcaccaaact ggaactgaaa cgtacggtgg ctgcaccatc tgtcttcatc     480
ttcccgccat ctgatgagca gttgaaatct ggaactgcct ctgttgtgtg cctgctgaat     540
aacttctatc ccagagaggc caaagtacag tggaaggtgg ataacgccct ccaatcgggt     600
aactcccagg agagtgtcac agagcaggac agcaaggaca gcacctacag cctcagcagc     660
accctgacgc tgagcaaagc agactacgag aaacacaaag tctacgcctg cgaagtcacc     720
catcagggcc tgagctcgcc cgtcacaaag agcttcaaca ggggagagtg ttag            774
```

<210> SEQ ID NO 10
<211> LENGTH: 257
<212> TYPE: PRT
<213> ORGANISM: Artificial Sequence
<220> FEATURE:
<223> OTHER INFORMATION: Des-4-3954-1204-C225 Activatable Antibody Light Chain

<400> SEQUENCE: 10

```
Gly Gln Cys Ile Ser Pro Arg Gly Cys Pro Asp Gly Pro Tyr Val Met
1               5                   10                  15

Tyr Gly Ser Ser Gly Gly Ser Gly Gly Ser Gly Gly Ser Gly Leu Ser
            20                  25                  30

Gly Arg Ser Asp Asn His Gly Ser Ser Gly Thr Gln Ile Leu Leu Thr
        35                  40                  45

Gln Ser Pro Val Ile Leu Ser Val Ser Pro Gly Glu Arg Val Ser Phe
    50                  55                  60

Ser Cys Arg Ala Ser Gln Ser Ile Gly Thr Asn Ile His Trp Tyr Gln
65                  70                  75                  80

Gln Arg Thr Asn Gly Ser Pro Arg Leu Leu Ile Lys Tyr Ala Ser Glu
                85                  90                  95

Ser Ile Ser Gly Ile Pro Ser Arg Phe Ser Gly Ser Gly Ser Gly Thr
            100                 105                 110

Asp Phe Thr Leu Ser Ile Asn Ser Val Glu Ser Glu Asp Ile Ala Asp
        115                 120                 125

Tyr Tyr Cys Gln Gln Asn Asn Asn Trp Pro Thr Thr Phe Gly Ala Gly
    130                 135                 140

Thr Lys Leu Glu Leu Lys Arg Thr Val Ala Ala Pro Ser Val Phe Ile
145                 150                 155                 160

Phe Pro Pro Ser Asp Glu Gln Leu Lys Ser Gly Thr Ala Ser Val Val
                165                 170                 175
```

```
Cys Leu Leu Asn Asn Phe Tyr Pro Arg Glu Ala Lys Val Gln Trp Lys
            180                 185                 190

Val Asp Asn Ala Leu Gln Ser Gly Asn Ser Gln Glu Ser Val Thr Glu
        195                 200                 205

Gln Asp Ser Lys Asp Ser Thr Tyr Ser Leu Ser Ser Thr Leu Thr Leu
    210                 215                 220

Ser Lys Ala Asp Tyr Glu Lys His Lys Val Tyr Ala Cys Glu Val Thr
225                 230                 235                 240

His Gln Gly Leu Ser Ser Pro Val Thr Lys Ser Phe Asn Arg Gly Glu
                245                 250                 255

Cys

<210> SEQ ID NO 11
<211> LENGTH: 771
<212> TYPE: DNA
<213> ORGANISM: Artificial Sequence
<220> FEATURE:
<223> OTHER INFORMATION: Des-5-3954-1204-C225 Activatable Antibody Light
      Chain

<400> SEQUENCE: 11
cagtgcatct cacctcgtgg ttgtccggac ggcccatacg tcatgtacgg ctcgagcggt      60
ggcagcggtg gctctggtgg atccggtctg agcggccgtt ccgataatca tggcagtagc     120
ggtacccaga tcttgctgac ccagagcccg gtgattctga gcgtgagccc gggcgaacgt     180
gtgagcttta gctgccgcgc gagccagagc attggcacca acattcattg gtatcagcag     240
cgcaccaacg gcagcccgcg cctgctgatt aaatatgcga gcgaaagcat tagcggcatt     300
ccgagccgct ttagcggcag cggcagcggc accgatttta ccctgagcat taacagcgtg     360
gaaagcgaag atattgcgga ttattattgc cagcagaaca caactggcc gaccaccttt     420 ggcgcgggca ccaaactgga actgaaacgt acggtggctg caccatctgt cttcatcttc     480
ccgccatctg atgagcagtt gaaatctgga actgcctctg ttgtgtgcct gctgaataac     540
ttctatccca gagaggccaa agtacagtgg aaggtggata acgccctcca atcgggtaac     600
tcccaggaga gtgtcacaga gcaggacagc aaggacagca cctacagcct cagcagcacc     660
ctgacgctga gcaaagcaga ctacgagaaa cacaaagtct acgcctgcga agtcacccat     720
cagggcctga gctcgcccgt cacaaagagc ttcaacaggg gagagtgtta g              771

<210> SEQ ID NO 12
<211> LENGTH: 256
<212> TYPE: PRT
<213> ORGANISM: Artificial Sequence
<220> FEATURE:
<223> OTHER INFORMATION: Des-5-3954-1204-C225 Activatable Antibody Light
      Chain

<400> SEQUENCE: 12

Gln Cys Ile Ser Pro Arg Gly Cys Pro Asp Gly Pro Tyr Val Met Tyr
1               5                   10                  15

Gly Ser Ser Gly Gly Ser Gly Gly Ser Gly Gly Ser Gly Leu Ser Gly
            20                  25                  30

Arg Ser Asp Asn His Gly Ser Ser Gly Thr Gln Ile Leu Leu Thr Gln
        35                  40                  45

Ser Pro Val Ile Leu Ser Val Ser Pro Gly Glu Arg Val Ser Phe Ser
    50                  55                  60
```

Cys Arg Ala Ser Gln Ser Ile Gly Thr Asn Ile His Trp Tyr Gln Gln
 65                  70                  75                  80

Arg Thr Asn Gly Ser Pro Arg Leu Leu Ile Lys Tyr Ala Ser Glu Ser
                 85                  90                  95

Ile Ser Gly Ile Pro Ser Arg Phe Ser Gly Ser Gly Ser Gly Thr Asp
            100                 105                 110

Phe Thr Leu Ser Ile Asn Ser Val Glu Ser Glu Asp Ile Ala Asp Tyr
        115                 120                 125

Tyr Cys Gln Gln Asn Asn Asn Trp Pro Thr Thr Phe Gly Ala Gly Thr
    130                 135                 140

Lys Leu Glu Leu Lys Arg Thr Val Ala Ala Pro Ser Val Phe Ile Phe
145                 150                 155                 160

Pro Pro Ser Asp Glu Gln Leu Lys Ser Gly Thr Ala Ser Val Val Cys
                165                 170                 175

Leu Leu Asn Asn Phe Tyr Pro Arg Glu Ala Lys Val Gln Trp Lys Val
            180                 185                 190

Asp Asn Ala Leu Gln Ser Gly Asn Ser Gln Glu Ser Val Thr Glu Gln
        195                 200                 205

Asp Ser Lys Asp Ser Thr Tyr Ser Leu Ser Ser Thr Leu Thr Leu Ser
    210                 215                 220

Lys Ala Asp Tyr Glu Lys His Lys Val Tyr Ala Cys Glu Val Thr His
225                 230                 235                 240

Gln Gly Leu Ser Ser Pro Val Thr Lys Ser Phe Asn Arg Gly Glu Cys
                245                 250                 255

<210> SEQ ID NO 13
<211> LENGTH: 15
<212> TYPE: DNA
<213> ORGANISM: Artificial Sequence
<220> FEATURE:
<223> OTHER INFORMATION: spacer sequence

<400> SEQUENCE: 13
ggccagtctg gccag                                                                15

<210> SEQ ID NO 14
<211> LENGTH: 5
<212> TYPE: PRT
<213> ORGANISM: Artificial Sequence
<220> FEATURE:
<223> OTHER INFORMATION: spacer peptide

<400> SEQUENCE: 14

Gly Gln Ser Gly Gln
1               5

<210> SEQ ID NO 15
<211> LENGTH: 12
<212> TYPE: DNA
<213> ORGANISM: Artificial Sequence
<220> FEATURE:
<223> OTHER INFORMATION: spacer sequence

<400> SEQUENCE: 15
cagtctggcc ag                                                                   12

<210> SEQ ID NO 16
<211> LENGTH: 4
<212> TYPE: PRT
<213> ORGANISM: Artificial Sequence

```
<220> FEATURE:
<223> OTHER INFORMATION: spacer peptide

<400> SEQUENCE: 16

Gln Ser Gly Gln
1

<210> SEQ ID NO 17
<211> LENGTH: 9
<212> TYPE: DNA
<213> ORGANISM: Artificial Sequence
<220> FEATURE:
<223> OTHER INFORMATION: spacer sequence

<400> SEQUENCE: 17 tctggccag                                                                  9

<210> SEQ ID NO 18
<211> LENGTH: 3
<212> TYPE: PRT
<213> ORGANISM: Artificial Sequence
<220> FEATURE:
<223> OTHER INFORMATION: spacer peptide

<400> SEQUENCE: 18

Ser Gly Gln
1

<210> SEQ ID NO 19
<211> LENGTH: 6
<212> TYPE: DNA
<213> ORGANISM: Artificial Sequence
<220> FEATURE:
<223> OTHER INFORMATION: spacer sequence

<400> SEQUENCE: 19 ggccag                                                                     6

<210> SEQ ID NO 20
<211> LENGTH: 2
<212> TYPE: PRT
<213> ORGANISM: Artificial Sequence
<220> FEATURE:
<223> OTHER INFORMATION: spacer peptide

<400> SEQUENCE: 20

Gly Gln
1

<210> SEQ ID NO 21
<211> LENGTH: 3
<212> TYPE: DNA
<213> ORGANISM: Artificial Sequence
<220> FEATURE:
<223> OTHER INFORMATION: spacer sequence

<400> SEQUENCE: 21 cag                                                                        3

<210> SEQ ID NO 22
<211> LENGTH: 1
<212> TYPE: PRT
<213> ORGANISM: Artificial Sequence
<220> FEATURE:
<223> OTHER INFORMATION: spacer peptide
```

<400> SEQUENCE: 22

Gln
1

<210> SEQ ID NO 23
<211> LENGTH: 45
<212> TYPE: DNA
<213> ORGANISM: Artificial Sequence
<220> FEATURE:
<223> OTHER INFORMATION: masking sequence

<400> SEQUENCE: 23
tgcatctcac ctcgtggttg tccggacggc ccatacgtca tgtac                45

<210> SEQ ID NO 24
<211> LENGTH: 15
<212> TYPE: PRT
<213> ORGANISM: Artificial Sequence
<220> FEATURE:
<223> OTHER INFORMATION: masking moiety peptide

<400> SEQUENCE: 24

Cys Ile Ser Pro Arg Gly Cys Pro Asp Gly Pro Tyr Val Met Tyr
1               5                   10                  15

<210> SEQ ID NO 25
<211> LENGTH: 39
<212> TYPE: DNA
<213> ORGANISM: Artificial Sequence
<220> FEATURE:
<223> OTHER INFORMATION: linker sequence

<400> SEQUENCE: 25
ggctcgagcg gtggcagcgg tggctctggt ggatccggt                       39

<210> SEQ ID NO 26
<211> LENGTH: 13
<212> TYPE: PRT
<213> ORGANISM: Artificial Sequence
<220> FEATURE:
<223> OTHER INFORMATION: linker peptide sequence

<400> SEQUENCE: 26

Gly Ser Ser Gly Gly Ser Gly Gly Ser Gly Gly Ser Gly
1               5                   10

<210> SEQ ID NO 27
<211> LENGTH: 24
<212> TYPE: DNA
<213> ORGANISM: Artificial Sequence
<220> FEATURE:
<223> OTHER INFORMATION: 1204 cleavable substrate sequence

<400> SEQUENCE: 27
ctgagcggcc gttccgataa tcat                                       24

<210> SEQ ID NO 28
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 28

Leu Ser Gly Arg Ser Asp Asn His
1               5

<210> SEQ ID NO 29
<211> LENGTH: 15
<212> TYPE: DNA
<213> ORGANISM: Artificial Sequence
<220> FEATURE:
<223> OTHER INFORMATION: linker sequence

<400> SEQUENCE: 29
ggcagtagcg gtacc                                                          15

<210> SEQ ID NO 30
<211> LENGTH: 5
<212> TYPE: PRT
<213> ORGANISM: Artificial Sequence
<220> FEATURE:
<223> OTHER INFORMATION: linker peptide sequence

<400> SEQUENCE: 30

Gly Ser Ser Gly Thr
1               5

<210> SEQ ID NO 31
<211> LENGTH: 645
<212> TYPE: DNA
<213> ORGANISM: Artificial Sequence
<220> FEATURE:
<223> OTHER INFORMATION: C225 sequence

<400> SEQUENCE: 31
cagatcttgc tgacccagag cccggtgatt ctgagcgtga gcccgggcga acgtgtgagc         60
tttagctgcc gcgcgagcca gagcattggc accaacattc attggtatca gcagcgcacc        120
aacggcagcc cgcgcctgct gattaaatat gcgagcgaaa gcattagcgg cattccgagc        180
cgctttagcg gcagcggcag cggcaccgat tttaccctga gcattaacag cgtggaaagc        240
gaagatattg cggattatta ttgccagcag aacaacaact ggccgaccac ctttggcgcg        300
ggcaccaaac tggaactgaa acgtacggtg gctgcaccat ctgtcttcat cttcccgcca        360
tctgatgagc agttgaaatc tggaactgcc tctgttgtgt gcctgctgaa taacttctat        420
cccagagagg ccaaagtaca gtggaaggtg gataacgccc tccaatcggg taactcccag        480
gagagtgtca cagagcagga cagcaaggac agcacctaca gcctcagcag caccctgacg        540
ctgagcaaag cagactacga gaaacacaaa gtctacgcct gcgaagtcac ccatcagggc        600
ctgagctcgc ccgtcacaaa gagcttcaac aggggagagt gttag                        645

<210> SEQ ID NO 32
<211> LENGTH: 214
<212> TYPE: PRT
<213> ORGANISM: Artificial Sequence
<220> FEATURE:
<223> OTHER INFORMATION: C225 sequence

<400> SEQUENCE: 32

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

```
Ile His Trp Tyr Gln Gln Arg Thr Asn Gly Ser Pro Arg Leu Leu Ile
         35                  40                  45
Lys Tyr Ala Ser Glu Ser Ile Ser Gly Ile Pro Ser Arg Phe Ser Gly
 50                  55                  60
Ser Gly Ser Gly Thr Asp Phe Thr Leu Ser Ile Asn Ser Val Glu Ser
 65                  70                  75                  80
Glu Asp Ile Ala Asp Tyr Tyr Cys Gln Gln Asn Asn Asn Trp Pro Thr
                 85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
            115                 120                 125
Thr Ala Ser Val Val Cys Leu Leu Asn Asn Phe Tyr Pro Arg Glu Ala
            130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 33
<211> LENGTH: 1350
<212> TYPE: DNA
<213> ORGANISM: Artificial Sequence
<220> FEATURE:
<223> OTHER INFORMATION: C225v4 Activatable Antibody Heavy Chain

<400> SEQUENCE: 33
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag gcctggaatg gctgggcgtg atttggagcg gcggcaacac cgattataac     180
accccgttta ccagccgcct gagcattaac aaagataaca gcaaaagcca ggtgtttttt     240
aaaatgaaca gcctgcaaag caacgatacc gcgatttatt attgcgcgcg cgcgctgacc     300
tattatgatt atgaatttgc gtattggggc cagggcaccc tggtgaccgt gagcgcggct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttccccg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
```

```
gccaaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 34
<211> LENGTH: 449
<212> TYPE: PRT
<213> ORGANISM: Artificial Sequence
<220> FEATURE:
<223> OTHER INFORMATION: C225v4 Activatable Antibody Heavy Chain

<400> SEQUENCE: 34

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 35
<211> LENGTH: 1350
<212> TYPE: DNA
<213> ORGANISM: Artificial Sequence
<220> FEATURE:
<223> OTHER INFORMATION: C225v6 Activatable Antibody Heavy Chain

<400> SEQUENCE: 35
caggtgcagc tgaaacagag cggcccgggc ctggtgcagc cgagccagag cctgagcatt     60
acctgcaccg tgagcggctt tagcctgacc aactatggcg tgcattgggt gcgccagagc    120
ccgggcaaag cctggaatg gctgggcgtg atttggagcg gcggcaacac cgattataac    180
accccgttta ccagccgcct gagcattaac aaagataaca gcaaaagcca ggtgtttttt    240
aaaatgaaca gcctgcaaag ccaggatacc gcgatttatt attgcgcgcg cgcgctgacc    300
tattatgatt atgaatttgc gtattggggc cagggcaccc tggtgaccgt gagcgcggct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacgccagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgaactg   1080
accaagaacc aggtcagcct gacctgcctg gtcaaaggct tctatccag cgacatcgcc   1140 gtggagtggg agagcaatgg gcagccggag aacaactaca agaccacgcc tcccgtgctg   1200

-continued

```
gactccgacg gctccttctt cctctacagc aagctcaccg tggacaagag caggtggcag    1260 cagggggaacg tcttctcatg ctccgtgatg catgaggctc tgcacaacca ctacacgcag    1320
aagagcctct ccctgtctcc gggtaaatga                                      1350
```

<210> SEQ ID NO 36
<211> LENGTH: 449
<212> TYPE: PRT
<213> ORGANISM: Artificial Sequence
<220> FEATURE:
<223> OTHER INFORMATION: C225v6 Activatable Antibody Heavy Chain

<400> SEQUENCE: 36

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

```
Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
            355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 37
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 37

Pro Arg Phe Lys Ile Ile Gly Gly
1               5

<210> SEQ ID NO 38
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 38

Pro Arg Phe Arg Ile Ile Gly Gly
1               5

<210> SEQ ID NO 39
<211> LENGTH: 9
<212> TYPE: PRT
<213> ORGANISM: Artificial Sequence
<220> FEATURE:
<223> OTHER INFORMATION: cleavable linker peptide sequence

<400> SEQUENCE: 39

Ser Ser Arg His Arg Arg Ala Leu Asp
1               5

<210> SEQ ID NO 40
<211> LENGTH: 14
<212> TYPE: PRT
<213> ORGANISM: Artificial Sequence
<220> FEATURE:
<223> OTHER INFORMATION: cleavable linker peptide sequence

<400> SEQUENCE: 40

Arg Lys Ser Ser Ile Ile Ile Arg Met Arg Asp Val Val Leu
1               5                   10

<210> SEQ ID NO 41
<211> LENGTH: 15
```

```
<212> TYPE: PRT
<213> ORGANISM: Artificial Sequence
<220> FEATURE:
<223> OTHER INFORMATION: cleavable linker peptide sequence

<400> SEQUENCE: 41

Ser Ser Ser Phe Asp Lys Gly Lys Tyr Lys Lys Gly Asp Asp Ala
1               5                   10                  15

<210> SEQ ID NO 42
<211> LENGTH: 15
<212> TYPE: PRT
<213> ORGANISM: Artificial Sequence
<220> FEATURE:
<223> OTHER INFORMATION: cleavable linker peptide sequence

<400> SEQUENCE: 42

Ser Ser Ser Phe Asp Lys Gly Lys Tyr Lys Arg Gly Asp Asp Ala
1               5                   10                  15

<210> SEQ ID NO 43
<211> LENGTH: 4
<212> TYPE: PRT
<213> ORGANISM: Artificial Sequence
<220> FEATURE:
<223> OTHER INFORMATION: cleavable linker peptide sequence

<400> SEQUENCE: 43

Ile Glu Gly Arg
1

<210> SEQ ID NO 44
<211> LENGTH: 4
<212> TYPE: PRT
<213> ORGANISM: Artificial Sequence
<220> FEATURE:
<223> OTHER INFORMATION: cleavable linker peptide sequence

<400> SEQUENCE: 44

Ile Asp Gly Arg
1

<210> SEQ ID NO 45
<211> LENGTH: 7
<212> TYPE: PRT
<213> ORGANISM: Artificial Sequence
<220> FEATURE:
<223> OTHER INFORMATION: cleavable linker peptide sequence

<400> SEQUENCE: 45

Gly Gly Ser Ile Asp Gly Arg
1               5

<210> SEQ ID NO 46
<211> LENGTH: 6
<212> TYPE: PRT
<213> ORGANISM: Artificial Sequence
<220> FEATURE:
<223> OTHER INFORMATION: cleavable linker peptide sequence

<400> SEQUENCE: 46

Pro Leu Gly Leu Trp Ala
1               5

<210> SEQ ID NO 47
<211> LENGTH: 8
<212> TYPE: PRT
```

```
<213> ORGANISM: Artificial Sequence
<220> FEATURE:
<223> OTHER INFORMATION: cleavable linker peptide sequence

<400> SEQUENCE: 47

Gly Pro Gln Gly Ile Ala Gly Gln
1               5

<210> SEQ ID NO 48
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 48

Gly Pro Gln Gly Leu Leu Gly Ala
1               5

<210> SEQ ID NO 49
<211> LENGTH: 5
<212> TYPE: PRT
<213> ORGANISM: Artificial Sequence
<220> FEATURE:
<223> OTHER INFORMATION: cleavable linker peptide sequence

<400> SEQUENCE: 49

Gly Ile Ala Gly Gln
1               5

<210> SEQ ID NO 50
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 50

Gly Pro Leu Gly Ile Ala Gly Ile
1               5

<210> SEQ ID NO 51
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 51

Gly Pro Glu Gly Leu Arg Val Gly
1               5

<210> SEQ ID NO 52
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 52

Tyr Gly Ala Gly Leu Gly Val Val
1               5

<210> SEQ ID NO 53
<211> LENGTH: 8
<212> TYPE: PRT
<213> ORGANISM: Artificial Sequence
```

```
<220> FEATURE:
<223> OTHER INFORMATION: cleavable linker peptide sequence

<400> SEQUENCE: 53

Ala Gly Leu Gly Val Val Glu Arg
1               5

<210> SEQ ID NO 54
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 54

Ala Gly Leu Gly Ile Ser Ser Thr
1               5

<210> SEQ ID NO 55
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 55

Glu Pro Gln Ala Leu Ala Met Ser
1               5

<210> SEQ ID NO 56
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 56

Gln Ala Leu Ala Met Ser Ala Ile
1               5

<210> SEQ ID NO 57
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 57

Ala Ala Tyr His Leu Val Ser Gln
1               5

<210> SEQ ID NO 58
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 58

Met Asp Ala Phe Leu Glu Ser Ser
1               5

<210> SEQ ID NO 59
<211> LENGTH: 8
<212> TYPE: PRT
<213> ORGANISM: Artificial Sequence
<220> FEATURE:
```

```
<223> OTHER INFORMATION: cleavable linker peptide sequence

<400> SEQUENCE: 59

Glu Ser Leu Pro Val Val Ala Val
1               5

<210> SEQ ID NO 60
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 60

Ser Ala Pro Ala Val Glu Ser Glu
1               5

<210> SEQ ID NO 61
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 61

Asp Val Ala Gln Phe Val Leu Thr
1               5

<210> SEQ ID NO 62
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 62

Val Ala Gln Phe Val Leu Thr Glu
1               5

<210> SEQ ID NO 63
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 63

Ala Gln Phe Val Leu Thr Glu Gly
1               5

<210> SEQ ID NO 64
<211> LENGTH: 8
<212> TYPE: PRT
<213> ORGANISM: Artificial Sequence
<220> FEATURE:
<223> OTHER INFORMATION: cleavable linker peptide sequence

<400> SEQUENCE: 64

Pro Val Gln Pro Ile Gly Pro Gln
1               5

<210> SEQ ID NO 65
<211> LENGTH: 4
<212> TYPE: PRT
<213> ORGANISM: Artificial Sequence
<220> FEATURE:
<223> OTHER INFORMATION: linker peptide sequence
```

```
<400> SEQUENCE: 65

Gly Ser Ser Gly
1

<210> SEQ ID NO 66
<211> LENGTH: 5
<212> TYPE: PRT
<213> ORGANISM: Artificial Sequence
<220> FEATURE:
<223> OTHER INFORMATION: linker peptide sequence
<220> FEATURE:
<221> NAME/KEY: REPEAT
<222> LOCATION: (1)..(5)
<223> OTHER INFORMATION: May be repeated

<400> SEQUENCE: 66

Gly Ser Gly Gly Ser
1               5

<210> SEQ ID NO 67
<211> LENGTH: 4
<212> TYPE: PRT
<213> ORGANISM: Artificial Sequence
<220> FEATURE:
<223> OTHER INFORMATION: linker peptide sequence
<220> FEATURE:
<221> NAME/KEY: REPEAT
<222> LOCATION: (1)..(4)
<223> OTHER INFORMATION: May be repeated

<400> SEQUENCE: 67

Gly Gly Gly Ser
1

<210> SEQ ID NO 68
<211> LENGTH: 4
<212> TYPE: PRT
<213> ORGANISM: Artificial Sequence
<220> FEATURE:
<223> OTHER INFORMATION: linker peptide sequence

<400> SEQUENCE: 68

Gly Gly Ser Gly
1

<210> SEQ ID NO 69
<211> LENGTH: 5
<212> TYPE: PRT
<213> ORGANISM: Artificial Sequence
<220> FEATURE:
<223> OTHER INFORMATION: linker peptide sequence

<400> SEQUENCE: 69

Gly Gly Ser Gly Gly
1               5

<210> SEQ ID NO 70
<211> LENGTH: 5
<212> TYPE: PRT
<213> ORGANISM: Artificial Sequence
<220> FEATURE:
<223> OTHER INFORMATION: linker peptide sequence

<400> SEQUENCE: 70

Gly Ser Gly Ser Gly
1               5
```

<210> SEQ ID NO 71
<211> LENGTH: 5
<212> TYPE: PRT
<213> ORGANISM: Artificial Sequence
<220> FEATURE:
<223> OTHER INFORMATION: linker peptide sequence

<400> SEQUENCE: 71

Gly Ser Gly Gly Gly
1               5

<210> SEQ ID NO 72
<211> LENGTH: 5
<212> TYPE: PRT
<213> ORGANISM: Artificial Sequence
<220> FEATURE:
<223> OTHER INFORMATION: linker peptide sequence

<400> SEQUENCE: 72

Gly Gly Gly Ser Gly
1               5

<210> SEQ ID NO 73
<211> LENGTH: 5
<212> TYPE: PRT
<213> ORGANISM: Artificial Sequence
<220> FEATURE:
<223> OTHER INFORMATION: linker peptide sequence

<400> SEQUENCE: 73

Gly Ser Ser Ser Gly
1               5

<210> SEQ ID NO 74
<211> LENGTH: 261
<212> TYPE: PRT
<213> ORGANISM: Artificial Sequence
<220> FEATURE:
<223> OTHER INFORMATION: Control anti-EGFR activatable antibody

<400> SEQUENCE: 74

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
                20                  25                  30

Ser Gly Leu Ser Gly Arg Ser Asp Asn His Gly Ser Ser Gly Thr Gln
            35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
                100                 105                 110

Gly Ser Gly Thr Asp Phe Thr Leu Ser Ile Asn Ser Val Glu Ser Glu
            115                 120                 125

Asp Ile Ala Asp Tyr Tyr Cys Gln Gln Asn Asn Asn Trp Pro Thr Thr
        130                 135                 140

Phe Gly Ala Gly Thr Lys Leu Glu Leu Lys Arg Thr Val Ala Ala Pro
145                 150                 155                 160

```
Ser Val Phe Ile Phe Pro Pro Ser Asp Glu Gln Leu Lys Ser Gly Thr
                165             170                 175
Ala Ser Val Val Cys Leu Leu Asn Asn Phe Tyr Pro Arg Glu Ala Lys
            180                 185                 190
Val Gln Trp Lys Val Asp Asn Ala Leu Gln Ser Gly Asn Ser Gln Glu
        195                 200                 205
Ser Val Thr Glu Gln Asp Ser Lys Asp Ser Thr Tyr Ser Leu Ser Ser
    210                 215                 220
Thr Leu Thr Leu Ser Lys Ala Asp Tyr Glu Lys His Lys Val Tyr Ala
225                 230                 235                 240
Cys Glu Val Thr His Gln Gly Leu Ser Ser Pro Val Thr Lys Ser Phe
                245                 250                 255
Asn Arg Gly Glu Cys
            260

<210> SEQ ID NO 75
<211> LENGTH: 6
<212> TYPE: PRT
<213> ORGANISM: Artificial Sequence
<220> FEATURE:
<223> OTHER INFORMATION: spacer peptide sequence

<400> SEQUENCE: 75

Gln Gly Gln Ser Gly Gln
1               5

<210> SEQ ID NO 76
<211> LENGTH: 6
<212> TYPE: PRT
<213> ORGANISM: Artificial Sequence
<220> FEATURE:
<223> OTHER INFORMATION: masking moiety peptide

<400> SEQUENCE: 76

Cys Ile Ser Pro Arg Gly
1               5

<210> SEQ ID NO 77
<211> LENGTH: 8
<212> TYPE: PRT
<213> ORGANISM: Artificial Sequence
<220> FEATURE:
<223> OTHER INFORMATION: masking moiety peptide

<400> SEQUENCE: 77

Cys Ile Ser Pro Arg Gly Cys Gly
1               5

<210> SEQ ID NO 78
<211> LENGTH: 14
<212> TYPE: PRT
<213> ORGANISM: Artificial Sequence
<220> FEATURE:
<223> OTHER INFORMATION: masking moiety peptide

<400> SEQUENCE: 78

Cys Ile Ser Pro Arg Gly Cys Pro Asp Gly Pro Tyr Val Met
1               5                   10

<210> SEQ ID NO 79
<211> LENGTH: 15
<212> TYPE: PRT
<213> ORGANISM: Artificial Sequence
<220> FEATURE:
```

<223> OTHER INFORMATION: masking moiety peptide

<400> SEQUENCE: 79

Cys Ile Ser Pro Arg Gly Cys Glu Pro Gly Thr Tyr Val Pro Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: masking moiety peptide

<400> SEQUENCE: 80

Cys Ile Ser Pro Arg Gly Cys Pro Gly Gln Ile Trp His Pro Pro
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: masking moiety peptide

<400> SEQUENCE: 81

Gly Ser His Cys Leu Ile Pro Ile Asn Met Gly Ala Pro Ser Cys
1               5                   10                  15

<210> SEQ ID NO 82
<211> LENGTH: 32
<212> TYPE: PRT
<213> ORGANISM: Artificial Sequence
<220> FEATURE:
<223> OTHER INFORMATION: masking moiety peptide

<400> SEQUENCE: 82

Cys Ile Ser Pro Arg Gly Cys Gly Gly Ser Ser Ala Ser Gln Ser Gly
1               5                   10                  15

Gln Gly Ser His Cys Leu Ile Pro Ile Asn Met Gly Ala Pro Ser Cys
            20                  25                  30

<210> SEQ ID NO 83
<211> LENGTH: 19
<212> TYPE: PRT
<213> ORGANISM: Artificial Sequence
<220> FEATURE:
<223> OTHER INFORMATION: masking moiety peptide

<400> SEQUENCE: 83

Cys Asn His His Tyr Phe Tyr Thr Cys Gly Cys Ile Ser Pro Arg Gly
1               5                   10                  15

Cys Pro Gly

<210> SEQ ID NO 84
<211> LENGTH: 19
<212> TYPE: PRT
<213> ORGANISM: Artificial Sequence
<220> FEATURE:
<223> OTHER INFORMATION: masking moiety peptide

<400> SEQUENCE: 84

Ala Asp His Val Phe Trp Gly Ser Tyr Gly Cys Ile Ser Pro Arg Gly
1               5                   10                  15

Cys Pro Gly

<210> SEQ ID NO 85
<211> LENGTH: 19
<212> TYPE: PRT
<213> ORGANISM: Artificial Sequence
<220> FEATURE:
<223> OTHER INFORMATION: masking moiety peptide

<400> SEQUENCE: 85

Cys His His Val Tyr Trp Gly His Cys Gly Cys Ile Ser Pro Arg Gly
1               5                   10                  15

Cys Pro Gly

<210> SEQ ID NO 86
<211> LENGTH: 19
<212> TYPE: PRT
<213> ORGANISM: Artificial Sequence
<220> FEATURE:
<223> OTHER INFORMATION: masking moiety peptide

<400> SEQUENCE: 86

Cys Pro His Phe Thr Thr Thr Ser Cys Gly Cys Ile Ser Pro Arg Gly
1               5                   10                  15

Cys Pro Gly

<210> SEQ ID NO 87
<211> LENGTH: 19
<212> TYPE: PRT
<213> ORGANISM: Artificial Sequence
<220> FEATURE:
<223> OTHER INFORMATION: masking moiety peptide

<400> SEQUENCE: 87

Cys Asn His His Tyr His Tyr Tyr Cys Gly Cys Ile Ser Pro Arg Gly
1               5                   10                  15

Cys Pro Gly

<210> SEQ ID NO 88
<211> LENGTH: 19
<212> TYPE: PRT
<213> ORGANISM: Artificial Sequence
<220> FEATURE:
<223> OTHER INFORMATION: masking moiety peptide

<400> SEQUENCE: 88

Cys Pro His Val Ser Phe Gly Ser Cys Gly Cys Ile Ser Pro Arg Gly
1               5                   10                  15

Cys Pro Gly

<210> SEQ ID NO 89
<211> LENGTH: 19
<212> TYPE: PRT
<213> ORGANISM: Artificial Sequence
<220> FEATURE:
<223> OTHER INFORMATION: masking moiety peptide

<400> SEQUENCE: 89

Cys Pro Tyr Tyr Thr Leu Ser Tyr Cys Gly Cys Ile Ser Pro Arg Gly
1               5                   10                  15

Cys Pro Gly

<210> SEQ ID NO 90
<211> LENGTH: 19
<212> TYPE: PRT

```
<213> ORGANISM: Artificial Sequence
<220> FEATURE:
<223> OTHER INFORMATION: masking moiety peptide

<400> SEQUENCE: 90

Cys Asn His Val Tyr Phe Gly Thr Cys Gly Cys Ile Ser Pro Arg Gly
1               5                   10                  15

Cys Pro Gly

<210> SEQ ID NO 91
<211> LENGTH: 19
<212> TYPE: PRT
<213> ORGANISM: Artificial Sequence
<220> FEATURE:
<223> OTHER INFORMATION: masking moiety peptide

<400> SEQUENCE: 91

Cys Asn His Phe Thr Leu Thr Thr Cys Gly Cys Ile Ser Pro Arg Gly
1               5                   10                  15

Cys Pro Gly

<210> SEQ ID NO 92
<211> LENGTH: 19
<212> TYPE: PRT
<213> ORGANISM: Artificial Sequence
<220> FEATURE:
<223> OTHER INFORMATION: masking moiety peptide

<400> SEQUENCE: 92

Cys His His Phe Thr Leu Thr Thr Cys Gly Cys Ile Ser Pro Arg Gly
1               5                   10                  15

Cys Pro Gly

<210> SEQ ID NO 93
<211> LENGTH: 18
<212> TYPE: PRT
<213> ORGANISM: Artificial Sequence
<220> FEATURE:
<223> OTHER INFORMATION: masking moiety peptide

<400> SEQUENCE: 93

Tyr Asn Pro Cys Ala Thr Pro Met Cys Cys Ile Ser Pro Arg Gly Cys
1               5                   10                  15

Pro Gly

<210> SEQ ID NO 94
<211> LENGTH: 18
<212> TYPE: PRT
<213> ORGANISM: Artificial Sequence
<220> FEATURE:
<223> OTHER INFORMATION: masking moiety peptide

<400> SEQUENCE: 94

Cys Asn His His Tyr Phe Tyr Thr Cys Gly Cys Ile Ser Pro Arg Gly
1               5                   10                  15

Cys Gly

<210> SEQ ID NO 95
<211> LENGTH: 18
<212> TYPE: PRT
<213> ORGANISM: Artificial Sequence
<220> FEATURE:
<223> OTHER INFORMATION: masking moiety peptide
```

```
<400> SEQUENCE: 95

Cys Asn His His Tyr His Tyr Tyr Cys Gly Cys Ile Ser Pro Arg Gly
1               5                   10                  15

Cys Gly

<210> SEQ ID NO 96
<211> LENGTH: 18
<212> TYPE: PRT
<213> ORGANISM: Artificial Sequence
<220> FEATURE:
<223> OTHER INFORMATION: masking moiety peptide

<400> SEQUENCE: 96

Cys Asn His Val Tyr Phe Gly Thr Cys Gly Cys Ile Ser Pro Arg Gly
1               5                   10                  15

Cys Gly

<210> SEQ ID NO 97
<211> LENGTH: 18
<212> TYPE: PRT
<213> ORGANISM: Artificial Sequence
<220> FEATURE:
<223> OTHER INFORMATION: masking moiety peptide

<400> SEQUENCE: 97

Cys His His Val Tyr Trp Gly His Cys Gly Cys Ile Ser Pro Arg Gly
1               5                   10                  15

Cys Gly

<210> SEQ ID NO 98
<211> LENGTH: 18
<212> TYPE: PRT
<213> ORGANISM: Artificial Sequence
<220> FEATURE:
<223> OTHER INFORMATION: masking moiety peptide

<400> SEQUENCE: 98

Cys Pro His Phe Thr Thr Thr Ser Cys Gly Cys Ile Ser Pro Arg Gly
1               5                   10                  15

Cys Gly

<210> SEQ ID NO 99
<211> LENGTH: 18
<212> TYPE: PRT
<213> ORGANISM: Artificial Sequence
<220> FEATURE:
<223> OTHER INFORMATION: masking moiety peptide

<400> SEQUENCE: 99

Cys Asn His Phe Thr Leu Thr Thr Cys Gly Cys Ile Ser Pro Arg Gly
1               5                   10                  15

Cys Gly

<210> SEQ ID NO 100
<211> LENGTH: 18
<212> TYPE: PRT
<213> ORGANISM: Artificial Sequence
<220> FEATURE:
<223> OTHER INFORMATION: masking moiety peptide
```

<400> SEQUENCE: 100

Cys His His Phe Thr Leu Thr Thr Cys Gly Cys Ile Ser Pro Arg Gly
1               5                   10                  15

Cys Gly

<210> SEQ ID NO 101
<211> LENGTH: 18
<212> TYPE: PRT
<213> ORGANISM: Artificial Sequence
<220> FEATURE:
<223> OTHER INFORMATION: masking moiety peptide

<400> SEQUENCE: 101

Cys Pro Tyr Tyr Thr Leu Ser Tyr Cys Gly Cys Ile Ser Pro Arg Gly
1               5                   10                  15

Cys Gly

<210> SEQ ID NO 102
<211> LENGTH: 18
<212> TYPE: PRT
<213> ORGANISM: Artificial Sequence
<220> FEATURE:
<223> OTHER INFORMATION: masking moiety peptide

<400> SEQUENCE: 102

Cys Pro His Val Ser Phe Gly Ser Cys Gly Cys Ile Ser Pro Arg Gly
1               5                   10                  15

Cys Gly

<210> SEQ ID NO 103
<211> LENGTH: 18
<212> TYPE: PRT
<213> ORGANISM: Artificial Sequence
<220> FEATURE:
<223> OTHER INFORMATION: masking moiety peptide

<400> SEQUENCE: 103

Ala Asp His Val Phe Trp Gly Ser Tyr Gly Cys Ile Ser Pro Arg Gly
1               5                   10                  15

Cys Gly

<210> SEQ ID NO 104
<211> LENGTH: 17
<212> TYPE: PRT
<213> ORGANISM: Artificial Sequence
<220> FEATURE:
<223> OTHER INFORMATION: masking moiety peptide

<400> SEQUENCE: 104

Tyr Asn Pro Cys Ala Thr Pro Met Cys Cys Ile Ser Pro Arg Gly Cys
1               5                   10                  15

Gly

<210> SEQ ID NO 105
<211> LENGTH: 18
<212> TYPE: PRT
<213> ORGANISM: Artificial Sequence
<220> FEATURE:
<223> OTHER INFORMATION: masking moiety peptide

```
<400> SEQUENCE: 105

Cys His His Val Tyr Trp Gly His Cys Gly Cys Ile Ser Pro Arg Gly
1               5                   10                  15

Cys Gly

<210> SEQ ID NO 106
<211> LENGTH: 18
<212> TYPE: PRT
<213> ORGANISM: Artificial Sequence
<220> FEATURE:
<223> OTHER INFORMATION: masking moiety peptide
<220> FEATURE:
<221> NAME/KEY: MISC_FEATURE
<222> LOCATION: (2)..(2)
<223> OTHER INFORMATION: Xaa may be Asn or Pro
<220> FEATURE:
<221> NAME/KEY: MISC_FEATURE
<222> LOCATION: (4)..(4)
<223> OTHER INFORMATION: Xaa may be His, Val or Phe
<220> FEATURE:
<221> NAME/KEY: MISC_FEATURE
<222> LOCATION: (5)..(5)
<223> OTHER INFORMATION: Xaa may be Tyr or Thr
<220> FEATURE:
<221> NAME/KEY: MISC_FEATURE
<222> LOCATION: (6)..(6)
<223> OTHER INFORMATION: Xaa may be Phe, Trp, Thr or Leu
<220> FEATURE:
<221> NAME/KEY: MISC_FEATURE
<222> LOCATION: (7)..(7)
<223> OTHER INFORMATION: Xaa may be Tyr, Gly, Thr or Ser
<220> FEATURE:
<221> NAME/KEY: MISC_FEATURE
<222> LOCATION: (8)..(8)
<223> OTHER INFORMATION: Xaa may be Thr, Ser, Tyr or His

<400> SEQUENCE: 106

Cys Xaa His Xaa Xaa Xaa Xaa Xaa Cys Gly Cys Ile Ser Pro Arg Gly
1               5                   10                  15

Cys Gly

<210> SEQ ID NO 107
<211> LENGTH: 15
<212> TYPE: PRT
<213> ORGANISM: Artificial Sequence
<220> FEATURE:
<223> OTHER INFORMATION: masking moiety peptide

<400> SEQUENCE: 107

Cys Ile Ser Pro Arg Gly Cys Gly Gln Pro Ile Pro Ser Val Lys
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: masking moiety peptide

<400> SEQUENCE: 108

Cys Ile Ser Pro Arg Gly Cys Thr Gln Pro Tyr His Val Ser Arg
1               5                   10                  15

<210> SEQ ID NO 109
<211> LENGTH: 15
<212> TYPE: PRT
<213> ORGANISM: Artificial Sequence
<220> FEATURE:
```

```
<223> OTHER INFORMATION: masking moiety peptide

<400> SEQUENCE: 109

Cys Ile Ser Pro Arg Gly Cys Asn Ala Val Ser Gly Leu Gly Ser
1               5                   10                  15

<210> SEQ ID NO 110
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 110

Ile Ser Ser Gly Leu Leu Ser Ser
1               5

<210> SEQ ID NO 111
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 111

Gln Asn Gln Ala Leu Arg Met Ala
1               5

<210> SEQ ID NO 112
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 112

Ala Gln Asn Leu Leu Gly Met Val
1               5

<210> SEQ ID NO 113
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 113

Ser Thr Phe Pro Phe Gly Met Phe
1               5

<210> SEQ ID NO 114
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 114

Pro Val Gly Tyr Thr Ser Ser Leu
1               5

<210> SEQ ID NO 115
<211> LENGTH: 8
<212> TYPE: PRT
<213> ORGANISM: Artificial Sequence
<220> FEATURE:
<223> OTHER INFORMATION: cleavable moiety peptide
```

<400> SEQUENCE: 115

Asp Trp Leu Tyr Trp Pro Gly Ile
1               5

<210> SEQ ID NO 116
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 116

Met Ile Ala Pro Val Ala Tyr Arg
1               5

<210> SEQ ID NO 117
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 117

Arg Pro Ser Pro Met Trp Ala Tyr
1               5

<210> SEQ ID NO 118
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 118

Trp Ala Thr Pro Arg Pro Met Arg
1               5

<210> SEQ ID NO 119
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 119

Phe Arg Leu Leu Asp Trp Gln Trp
1               5

<210> SEQ ID NO 120
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 120

Leu Lys Ala Ala Pro Arg Trp Ala
1               5

<210> SEQ ID NO 121
<211> LENGTH: 8
<212> TYPE: PRT
<213> ORGANISM: Artificial Sequence
<220> FEATURE:
<223> OTHER INFORMATION: cleavable moiety peptide

```
<400> SEQUENCE: 121

Gly Pro Ser His Leu Val Leu Thr
1               5

<210> SEQ ID NO 122
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 122

Leu Pro Gly Gly Leu Ser Pro Trp
1               5

<210> SEQ ID NO 123
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 123

Met Gly Leu Phe Ser Glu Ala Gly
1               5

<210> SEQ ID NO 124
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 124

Ser Pro Leu Pro Leu Arg Val Pro
1               5

<210> SEQ ID NO 125
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 125

Arg Met His Leu Arg Ser Leu Gly
1               5

<210> SEQ ID NO 126
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 126

Leu Ala Ala Pro Leu Gly Leu Leu
1               5

<210> SEQ ID NO 127
<211> LENGTH: 8
<212> TYPE: PRT
<213> ORGANISM: Artificial Sequence
<220> FEATURE:
<223> OTHER INFORMATION: cleavable moiety peptide
```

```
<400> SEQUENCE: 127

Ala Val Gly Leu Leu Ala Pro Pro
1               5

<210> SEQ ID NO 128
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 128

Leu Leu Ala Pro Ser His Arg Ala
1               5

<210> SEQ ID NO 129
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 129

Pro Ala Gly Leu Trp Leu Asp Pro
1               5

<210> SEQ ID NO 130
<211> LENGTH: 7
<212> TYPE: PRT
<213> ORGANISM: Artificial Sequence
<220> FEATURE:
<223> OTHER INFORMATION: cleavable moiety peptide

<400> SEQUENCE: 130

Ile Ser Ser Gly Leu Ser Ser
1               5

<210> SEQ ID NO 131
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 131

Thr Gly Arg Gly Pro Ser Trp Val
1               5

<210> SEQ ID NO 132
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 132

Ser Ala Arg Gly Pro Ser Arg Trp
1               5

<210> SEQ ID NO 133
<211> LENGTH: 8
<212> TYPE: PRT
<213> ORGANISM: Artificial Sequence
<220> FEATURE:
<223> OTHER INFORMATION: cleavable moiety peptide
```

```
<400> SEQUENCE: 133

Thr Ala Arg Gly Pro Ser Phe Lys
1               5

<210> SEQ ID NO 134
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 134

Leu Ser Gly Arg Ser Asp Asn His
1               5

<210> SEQ ID NO 135
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 135

Gly Gly Trp His Thr Gly Arg Asn
1               5

<210> SEQ ID NO 136
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 136

His Thr Gly Arg Ser Gly Ala Leu
1               5

<210> SEQ ID NO 137
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 137

Pro Leu Thr Gly Arg Ser Gly Gly
1               5

<210> SEQ ID NO 138
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 138

Ala Ala Arg Gly Pro Ala Ile His
1               5

<210> SEQ ID NO 139
<211> LENGTH: 8
<212> TYPE: PRT
<213> ORGANISM: Artificial Sequence
<220> FEATURE:
<223> OTHER INFORMATION: cleavable moiety peptide
```

<400> SEQUENCE: 139

Arg Gly Pro Ala Phe Asn Pro Met
1               5

<210> SEQ ID NO 140
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 140

Ser Ser Arg Gly Pro Ala Tyr Leu
1               5

<210> SEQ ID NO 141
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 141

Arg Gly Pro Ala Thr Pro Ile Met
1               5

<210> SEQ ID NO 142
<211> LENGTH: 4
<212> TYPE: PRT
<213> ORGANISM: Artificial Sequence
<220> FEATURE:
<223> OTHER INFORMATION: cleavable moiety peptide

<400> SEQUENCE: 142

Arg Gly Pro Ala
1

<210> SEQ ID NO 143
<211> LENGTH: 10
<212> TYPE: PRT
<213> ORGANISM: Artificial Sequence
<220> FEATURE:
<223> OTHER INFORMATION: cleavable moiety peptide

<400> SEQUENCE: 143

Gly Gly Gln Pro Ser Gly Met Trp Gly Trp
1               5                   10

<210> SEQ ID NO 144
<211> LENGTH: 10
<212> TYPE: PRT
<213> ORGANISM: Artificial Sequence
<220> FEATURE:
<223> OTHER INFORMATION: cleavable moiety peptide

<400> SEQUENCE: 144

Phe Pro Arg Pro Leu Gly Ile Thr Gly Leu
1               5                   10

<210> SEQ ID NO 145
<211> LENGTH: 10
<212> TYPE: PRT
<213> ORGANISM: Artificial Sequence
<220> FEATURE:
<223> OTHER INFORMATION: cleavable moiety peptide

```
<400> SEQUENCE: 145

Val His Met Pro Leu Gly Phe Leu Gly Pro
1               5                   10

<210> SEQ ID NO 146
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 146

Ser Pro Leu Thr Gly Arg Ser Gly
1               5

<210> SEQ ID NO 147
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 147

Ser Ala Gly Phe Ser Leu Pro Ala
1               5

<210> SEQ ID NO 148
<211> LENGTH: 9
<212> TYPE: PRT
<213> ORGANISM: Artificial Sequence
<220> FEATURE:
<223> OTHER INFORMATION: cleavable moiety peptide

<400> SEQUENCE: 148

Leu Ala Pro Leu Gly Leu Gln Arg Arg
1               5

<210> SEQ ID NO 149
<211> LENGTH: 8
<212> TYPE: PRT
<213> ORGANISM: Artificial Sequence
<220> FEATURE:
<223> OTHER INFORMATION: cleavable moiety peptide

<400> SEQUENCE: 149

Ser Gly Gly Pro Leu Gly Val Arg
1               5

<210> SEQ ID NO 150
<211> LENGTH: 4
<212> TYPE: PRT
<213> ORGANISM: Artificial Sequence
<220> FEATURE:
<223> OTHER INFORMATION: cleavable moiety peptide

<400> SEQUENCE: 150

Pro Leu Gly Leu
1
```